(12) United States Patent
Baradwan et al.

(10) Patent No.: US 12,404,246 B1
(45) Date of Patent: Sep. 2, 2025

(54) 2-AMINOMETHYLIMIDAZOLE MIMICS OF NS4A AND THEIR EFFECT THEREOF ON HEPATITIS C VIRUS NS3 PROTEASE

(71) Applicants: Mohammed A. Baradwan, Jeddah (SA); Abdelsattar M. Omar, Jeddah (SA); Mahmoud A. Elfaky, Jeddah (SA); Moustafa E. El-Araby, Cairo Governorate (EG); Sameh H. Soror, Cairo Governorate (EG)

(72) Inventors: Mohammed A. Baradwan, Jeddah (SA); Abdelsattar M. Omar, Jeddah (SA); Mahmoud A. Elfaky, Jeddah (SA); Moustafa E. El-Araby, Cairo Governorate (EG); Sameh H. Soror, Cairo Governorate (EG)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 18/903,487

(22) Filed: Oct. 1, 2024

(51) Int. Cl.
| | |
|---|---|
| *C07D 233/90* | (2006.01) |
| *A61K 31/4164* | (2006.01) |
| *A61K 31/4439* | (2006.01) |
| *A61K 45/06* | (2006.01) |
| *C07D 401/12* | (2006.01) |

(52) U.S. Cl.
CPC ........ *C07D 233/90* (2013.01); *A61K 31/4164* (2013.01); *A61K 31/4439* (2013.01); *A61K 45/06* (2013.01); *C07D 401/12* (2013.01)

(58) Field of Classification Search
CPC .......... C07D 233/90; C07D 401/12; A61K 31/4164; A61K 31/4439; A61K 45/06
See application file for complete search history.

(56) References Cited

U.S. PATENT DOCUMENTS

| | | | | |
|---|---|---|---|---|
| 7,973,061 | B2* | 7/2011 | Leahy | A61P 9/10 548/255 |
| 10,821,096 | B1 | 11/2020 | El-Araby et al. | |
| 10,959,987 | B2 | 3/2021 | El-Araby et al. | |
| 2006/0229293 | A1* | 10/2006 | Lotsof | A61K 31/55 514/23 |

OTHER PUBLICATIONS

El-Araby et al: "Synthetic bulky NS4A peptide variants bind to and inhibit HCV NS3 protease", Journal of Advanced Research, vol. 24, p. 251-259, 2020.
Khayat et al: "Reexamining Povarov Reaction's Scope and Limitation in the Generation of HCV-NS4A Peptidomimetics", Hindawi, Heteroatom Chemistry, vol. 2022, Feb. 10, 2022.
Omar et al: "1H-Imidazole-2,5-Dicarboxamides as NS4A Peptidomimetics: Identification of a New Approach to Inhibit HCV-NS3 Protease", Biomolecules, vol. 10, No. 479, Mar. 21, 2020.

* cited by examiner

*Primary Examiner* — Kamal A Saeed
*Assistant Examiner* — Quincy McKoy
(74) *Attorney, Agent, or Firm* — WCF IP

(57) ABSTRACT

Chronic hepatitis C is a global health problem affecting large number of people and leads to mortalities and morbidities. In this invention, new compounds belonging to 2-substituted-1H-imidazole-4-carboxamide derivatives (Formula I) intended for use in the treatment of hepatitis C are disclosed. The compounds interfere with the important viral peptide NS4A co-enzyme function. The described art includes chemical synthesis, spectral confirmation and binding assays with NS3 protein.

10 Claims, 72 Drawing Sheets
Specification includes a Sequence Listing.

Molecular Weight: 212.2

Comp 3

Molecular Weight: 295.4

Comp 6

Molecular Weight: 323.4

Comp 7

Molecular Weight: 295.4

Comp 10

Molecular Weight: 357.5

Comp 12

Molecular Weight: 343.5

|         | EXP 1 $T_{agg}$ (°C) | EXP 2 $T_{agg}$ (°C) | EXP 3 $T_{agg}$ (°C) | AVERAGE $T_{agg}$ (°C) | ST.DEV. | $\Delta T_{agg}$ (°C) |
|---------|-------|-------|-------|---------|---------|-------|
| NS3     | 43.20 | 43.27 | 43.19 | 43.22   | 0.00    |       |
| NS3+4A  | 44.32 | 44.32 | 44.57 | 44.40   | 0.15    | 1.19  |
| COMP 1  | 43.38 | 43.38 | 43.39 | 43.38   | 0.00    | 0.17  |
| COMP 2  | 43.09 | 43.28 | 43.26 | 43.21   | 0.10    | -0.01 |
| COMP 3  | 43.71 | 43.79 | 43.56 | 43.68   | 0.12    | 0.47  |
| COMP 4  | 43.04 | 43.01 | 43.51 | 43.19   | 0.28    | -0.03 |
| COMP 5  | 43.22 | 43.21 | 43.26 | 43.23   | 0.03    | 0.01  |
| COMP 6  | 43.60 | 43.50 | 43.42 | 43.51   | 0.09    | 0.29  |
| COMP 7  | 43.36 | 43.59 | 43.54 | 43.50   | 0.12    | 0.28  |
| COMP 8  | 43.72 | 43.75 | 43.60 | 43.69   | 0.08    | 0.48  |
| COMP 9  | 44.03 | 44.29 | 44.07 | 44.13   | 0.14    | 0.91  |
| COMP 10 | 43.24 | 43.50 | 44.20 | 43.65   | 0.50    | 0.43  |
| COMP 11 | 43.45 | 43.37 | 43.36 | 43.39   | 0.05    | 0.18  |
| COMP 12 | 44.00 | 43.53 | 43.83 | 43.79   | 0.23    | 0.57  |
| COMP 13 | 44.69 | 44.50 | 44.51 | 44.57   | 0.11    | 1.35  |

Fig. 31

SEQUENCE LISTING

```
Sequence total quantity: 2
SEQ ID NO: 1            moltype = AA  length = 193
FEATURE                 Location/Qualifiers
source                  1..193
                        mol_type = protein
                        organism = Hepatitis C
SEQUENCE: 1
GSVVIVGRVN LSGDTAYAQQ TRGEESTQET SQTGRDTNEN CGEVQVLSTA TQSFLGTAVN    60
GVMWTVYHGA GSKTISGPKG PVNQMYTNVD QDLVGWPSPP GVKSLTPCTC GASDLYLVTR   120
HADVVPVRRR GDTRGALLSP RPISTLKGSS GGPLLCPMGH AAGLFRAAVS TRGVAKAVDF   180
VPVESLETTM RSP                                                      193

SEQ ID NO: 2            moltype = AA  length = 200
FEATURE                 Location/Qualifiers
source                  1..200
                        mol_type = protein
                        organism = synthetic construct
SEQUENCE: 2
MASMTGGQQM GAPITAYAQQ TRGLFSTIVT SLTGRDTNEN CGEVQVLSTA TQSFLGTAVN    60
GVMWTVYHGA GSKTISGPKG PVNQMYTNVD QDLVGWPSPP GVKSLTPCTC GASDLYLVTR   120
HADVVPVRRR GDTRGALLSP RPISTLKGSS GGPLLCPMGH AAGLFRAAVC TRGVAKAVDF   180
VPVESLETTM RSGSHHHHHH                                               200
```

2-AMINOMETHYLIMIDAZOLE MIMICS OF NS4A AND THEIR EFFECT THEREOF ON HEPATITIS C VIRUS NS3 PROTEASE

SEQUENCE LISTING

This application includes as the Sequence Listing the complete contents of the accompanying text file "sequence listing", created Sep. 24, 2024, containing 3007 bytes, hereby incorporated by reference.

FIELD OF INVENTION

This invention relates to compounds having a formula of 2,4-disubstituted-1H-imidazole core. The substituents are one a carboxamide functional groups and a non-amidic group. The compositions of this formula were designed to mimic hepatitis C virus NS4A and were able to bind to the NS3 protein leading to loss of its function as a vital protease. The disclosed compositions may be used to treat chronic hepatitis by inhibiting the HCV growth and replication.

BACKGROUND

Hepatitis C is a significant global health concern, with approximately 58 million people worldwide living with chronic hepatitis C infection while it causes the death of 290,000 thousand people (Stroffolini and Stroffolini 2024). The highest prevalence of hepatitis C is found in the Eastern Mediterranean Region (4.6%) and South-East Asia (3.9%). Countries with the highest number of infected individuals include China, India, Pakistan, Egypt and Nigeria (Cui, Blach et al. 2023). In the United States, there is 2.2 million patients (Lewis, Barker et al. 2023) and the pattern of new infections is increasingly concerning (Yang, Qi et al. 2023).

The early symptoms of hepatitis C, including fever, fatigue, nausea, and liver tenderness, are often mild and may go unnoticed by many patients. However, if left untreated, the virus can silently progress over several years, leading to severe complications. The progression typically starts with viral activation and replication, liver scarring and fibrosis that worsen into cirrhosis, liver failure and carcinoma (Lauer and Walker 2001, Manns, Buti et al. 2017).

Hepatitis C is primarily transmitted upon blood-to-blood contact (MacDonald, Crofts et al. 1996) typically due to the sharing of needles or syringes contaminated with infected blood (Haber, Young et al. 2007). Other significant transmission routes include receiving blood transfusions or organ transplants from an infected donor (Pereira, Milford et al. 1991) and the use of contaminated invasive medical devises and dental care tools in healthcare settings (Younai 2010). High-risk activities may lead to HCV transmissions such as tattooing, piercing or sharing personal care items (razors, toothbrushes, or nail clippers) have been implicated in HCV transmission. Additionally, engaging in unprotected sex with an infected partner (Rooney and Gilson 1998) is one of the common transmission mechanisms of the virus. During childbirth, an infected mother may pass the virus to her baby (approximately 5-6% chance) (Indolfi and Resti 2009). Over the past three decades, intensive efforts by healthcare authorities and awareness campaigns have led to a significant decline in newly diagnosed cases (Hill, Nath et al. 2017). These efforts, coupled with the introduction of a robust arsenal of direct antiviral agents (DAAs), have renewed optimism that the World Health Organization's plan to eradicate hepatitis C globally by 2030 might be successful (Hill, Nath et al. 2017).

Historically, the treatment of chronic hepatitis C was limited to alpha-interferon (IFNα) and ribavirin, which were associated with low efficacy and high resistance rates (Poynard, Leroy et al. 1996, Hill, Nath et al. 2017). However, the advent of DAAs has revolutionized the treatment of chronic hepatitis C, leading to complete recovery in many cases (Nguyen, Huang et al. 2023). The approval of new drug combinations, either DAAs alone or in conjunction with IFNα/ribavirin, has dramatically increased the rate of complete and sustained viral recovery (SVR), achieving a 95% success rate in non-cirrhotic patients and an 80-90% success rate in cirrhotic patients (Lynch and Russo 2023).

Hepatitis C is an RNA virus and does not integrate into the host cell genome. Therefore, complete eradication is possible with proper treatment. The HCV genome is a positive-sense, single-stranded RNA virus belonging to Flaviviridae (Gould and Solomon 2008). The hepatitis C virus (HCV) genome consists of approximately 9,400 positive sense nucleotides, featuring highly conserved regions at both the 5' and 3' terminals. The genome's organization features a non-coding region preceding the open reading frame encoding to a single, long sequence encoding a polyprotein of 3010-3303 amino acids. This polyprotein is subsequently processed into structural protein that are involved in virus particle formation and non-structural (NS) proteins that are crucial for virus maturation and replication, including NS3, NS4A, NS4B, NS5A and NS5B. These NS proteins play essential roles in the virus life cycle, enabling HCV to replicate and survive within host cells. The NS proteins are targeted by DAAs and many of them are used alone or in combination for the treatment of chronic hepatitis C. For instance, the NS3 protease is inhibited by substrate site inhibitors including boceprevir, telaprevir, simeprevir, asunaprevir, paritarevir and grazoprevir. NS5A is targeted by daclatasvir, ledipasvir, ombitasvir, elbasvir, and velpatasvir while NS5B inhibitors are also commonly used as DAAs such as soforbuvir, and dasabuvir.

Regardless the fact that the DAAs has transformed the chronic hepatitis C from a deadly infection into curable illness, the emergence of resistance-associated substitutions (RASs) has raised concerns about the long-term efficacy of DAAs (Dietz, Müllhaupt et al. 2023). As HCV is a highly mutable virus, it can develop resistance to DAAs through various mechanisms, including genetic mutations and selection pressure (Mushtaq, Hashmi et al. 2022). Recent studies have identified RAS in the NS3, NS5A, and NS5B regions of the HCV genome, which can compromise the effectiveness of DAAs such as protease inhibitors, NS5A inhibitors, and nucleotide polymerase inhibitors. The emergence of resistance highlights the need for continued monitoring of treatment outcomes, development of next-generation DAAs with improved resistance profiles, and optimization of treatment strategies to minimize the risk of resistance and ensure sustained virologic response (Izhari 2023). In this regard, new approaches, rather than new compounds, are needed. Characterizing new viral targets other than NS3 (substrate site), NS5A and NS5B, is a pressing need to overcome the increasing resistance. In addition, the realization of the eradication goal depends on access to the treatment in economically-challenged areas must be increased (Chhatwal, Chen et al. 2018). Another important issue is the efficacy in broader sectors of HCV patients, such as elder and impaired kidney or liver patients, must be increased (Hellard, Chou et al. 2017).

NS4A is a relatively short, multi-functional protein consisting of 54 amino acids that plays an essential role in HCV growth and maturation. Foremost, it is critical for the activation of NS3 protease/helicase activities. The N-terminal region of NS4A adopts a 3-sheet structure and binds in an antiparallel fashion between the A0 and A1 helices. This binding induces the correct positioning of the catalytic triad (Asp81, His57, and Ser139) in NS3, enabling proteolytic activity (Kim, Morgenstern et al. 1996). In addition, NS4A hooks to the endoplasmic reticulum, an important event for the integration of NS3 to the host cell endoplasmic reticulum (Ci and Shi 2021). Among its functions, it has roles in RNA replication, late stage viral assembly and induction of the viral resistance to IFNα (Roder, Vazquez et al. 2019).

SUMMARY OF THE INVENTION

One objective of the invention is to provide therapeutic di-substituted imidazole-based compounds and a process of synthesizing these compounds.

A further objective of the invention is to provide a pharmaceutical composition comprising disubstituted imidazole monoamide-based compounds and a method of treating or preventing HCV infection.

NS4A inhibitors are a promising strategy to develop newer HCV therapeutics. An aspect of the invention introduces a new class of compounds that interfere with NS4A in its binding with NS3 protease and deactivate the enzyme.

The present invention relates to a compound of formula (I)

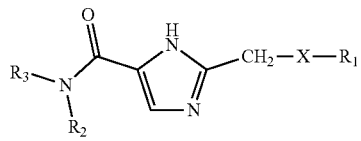

or a salt thereof, a solvate thereof, a tautomer thereof, a stereoisomer thereof, or a mixture thereof, wherein (i) $R_1$ is selected from the group consisting of an optionally substituted H, alkyl, an optionally substituted cycloalkyl, an optionally substituted arylalkyl, and an optionally substituted aryl, (ii) X is a heteroatom bridge consisting of one atom of examples NH, O or S, and (iii) R2 & R3 are the same or different and are independently H, alkyl, aralkyl, heteroaralkyl, or hetero-substituted alkyl (with N, O or S) of maximum size of 10 atoms (excluding valence filling hydrogens) with linear, branched or cyclic arrangements.

In one embodiment, $R_1$ is optionally $C_4$-$C_8$ alkyl substituted with at least one substituent selected from the group consisting of an alkyloxy, a cycloalkyloxy, an aryloxy, an amine, and an amide.

In one embodiment, $R_2$ is heteroatom-containing alkyl, aralkyl, heteroarylalkyl, heterocyclic, or benzylic.

In one embodiment, the compounds are preferably Formula (II)

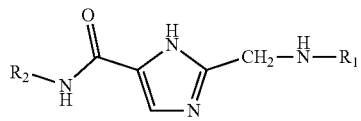

or a salt thereof, a solvate thereof, a tautomer thereof, a stereoisomer thereof, or a mixture thereof, wherein (i) $R_1$ is selected from the group consisting of an optionally substituted H, alkyl, an optionally substituted cycloalkyl, an optionally substituted arylalkyl, and an optionally substituted aryl, (ii) $R_2$ is alkyl, aralkyl, or hetero-substituted alkyl (with N, O or S) of maximum size of 10 atoms (excluding valence filling hydrogens) with linear, branched or cyclic arrangements.

In one embodiment NH has basic properties and may form salts with a pharmaceutically compatible counterions.

In one embodiment, $R_1$ is a $C_4$-$C_8$ alkyl optionally substituted with at least one substituent selected from the group consisting of an alkyloxy, a cycloalkyloxy, an aryloxy, an amine, and an amide.

In one embodiment, $R_1$ is a linear or branched $C_{4-8}$ alkyl.

In one embodiment, $R_1$ is at least one selected from the group consisting of n-butyl, n-pentyl, n-hexyl, n-heptyl, 2-(cyclohexyloxy)ethyl, 3-(cyclohexyloxy)propyl, 2-phenoxyethyl, 3-phenoxypropyl, 4-isopropoxybutyl, 6-methylheptyl, 3-methylpentyl and 2-(acetamido)ethyl.

In one embodiment, $R_1$ is optionally $C_2$-$C_8$ alkyl substituted with at least one substituent selected from the group consisting of an alkyloxy, a cycloalkyloxy, an aryloxy, an amine, and an amide.

In one embodiment, $R_2$ is an H, alkyl, substituted alkyl, heteroatom-containing alkyl, aralkyl, heteroarylalkyl, heterocyclic, or benzylic.

In one embodiment, $R_2$ is selected from the group consisting of an unsubstituted amide (—C(O)NH$_2$), N-methylamide (—C(O)NHCH$_3$), —NH—CH$_2$—CO—NHCH$_3$, a benzyl, a pyridylmethyl, and a furylmethyl.

In a preferred embodiment, the compound of Formula (I) is

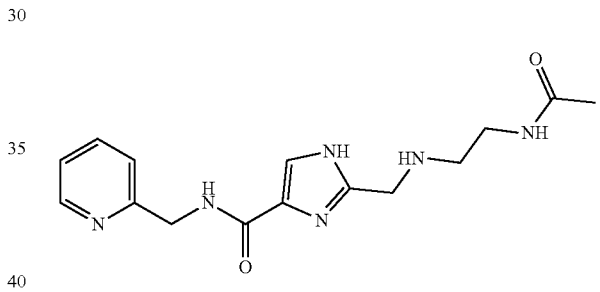

Exemplary Compounds

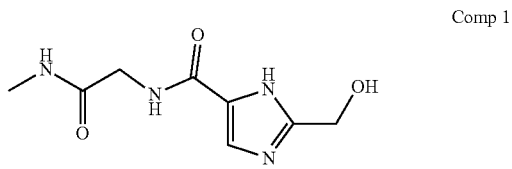
Comp 1

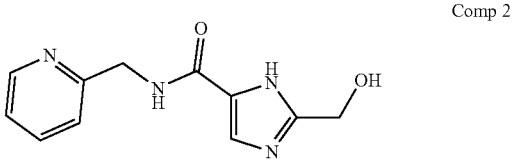
Comp 2

Comp 3

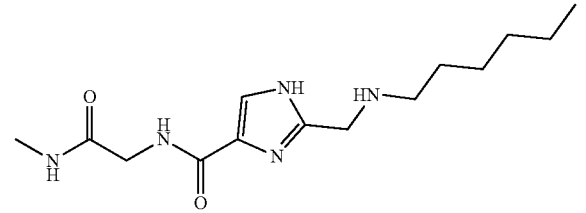

The compounds of the present disclosure may be prepared by methods known to those of ordinary skills in the art. The following methods set forth below are provided for illustrative purposes and are not intended to limit the scope of the disclosure. It will be recognized that it may be preferred or necessary to prepare such a compound in which a functional group is protected using a conventional protecting group then to remove the protecting group to provide a compound of the present disclosure.

The compounds of formulae (I) and (II) may, for example, be synthesized according to a process illustrated in FIG. 1.

BRIEF DESCRIPTION OF THE DRAWINGS

FIG. 31. Table of aggregation temperature shifts ($\Delta T_{agg}$) of NS3 when mixed with Comp 1 to Comp 2 (non-colored bars, $R_2$=OH), Comp 3- to Comp 8 (striped bars, $R_2$=CH2-CO—NHMe), Comp 9-13 (solid colored bars, $R_2$=pyridine-2-ylmethyl) and native peptide NS4A (dotted bar).

DETAILED DESCRIPTION OF THE EMBODIMENTS

Figure 1:
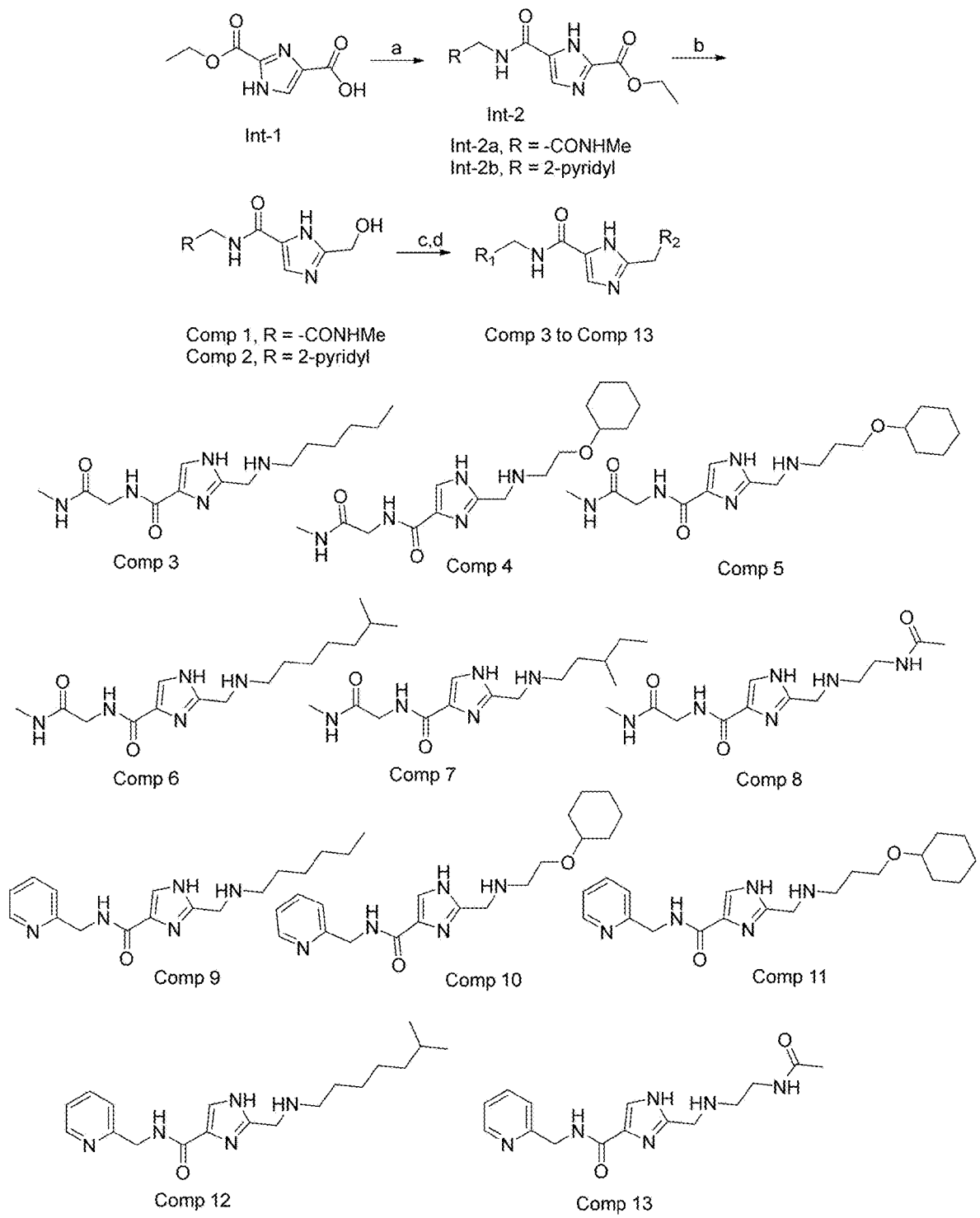
FIG. 1. Scheme of synthesis of compounds in the disclosure: (a) EDCI, HOBt, DIPEA, Iry Amine, THF, rt, 1h then 60° C. (b) LAH, THF, 0° C. (c) $MnO_2$, 80° C. (d) Amine, $NaBH(OAc)_3$, EtOH, AcOH.
Figure 2A:
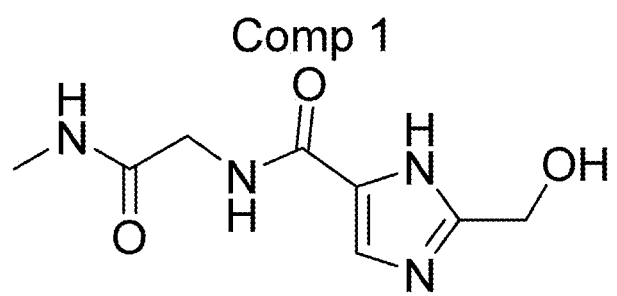
FIG. 2A. chemical structure of Comp. 1.
Figure 2B:
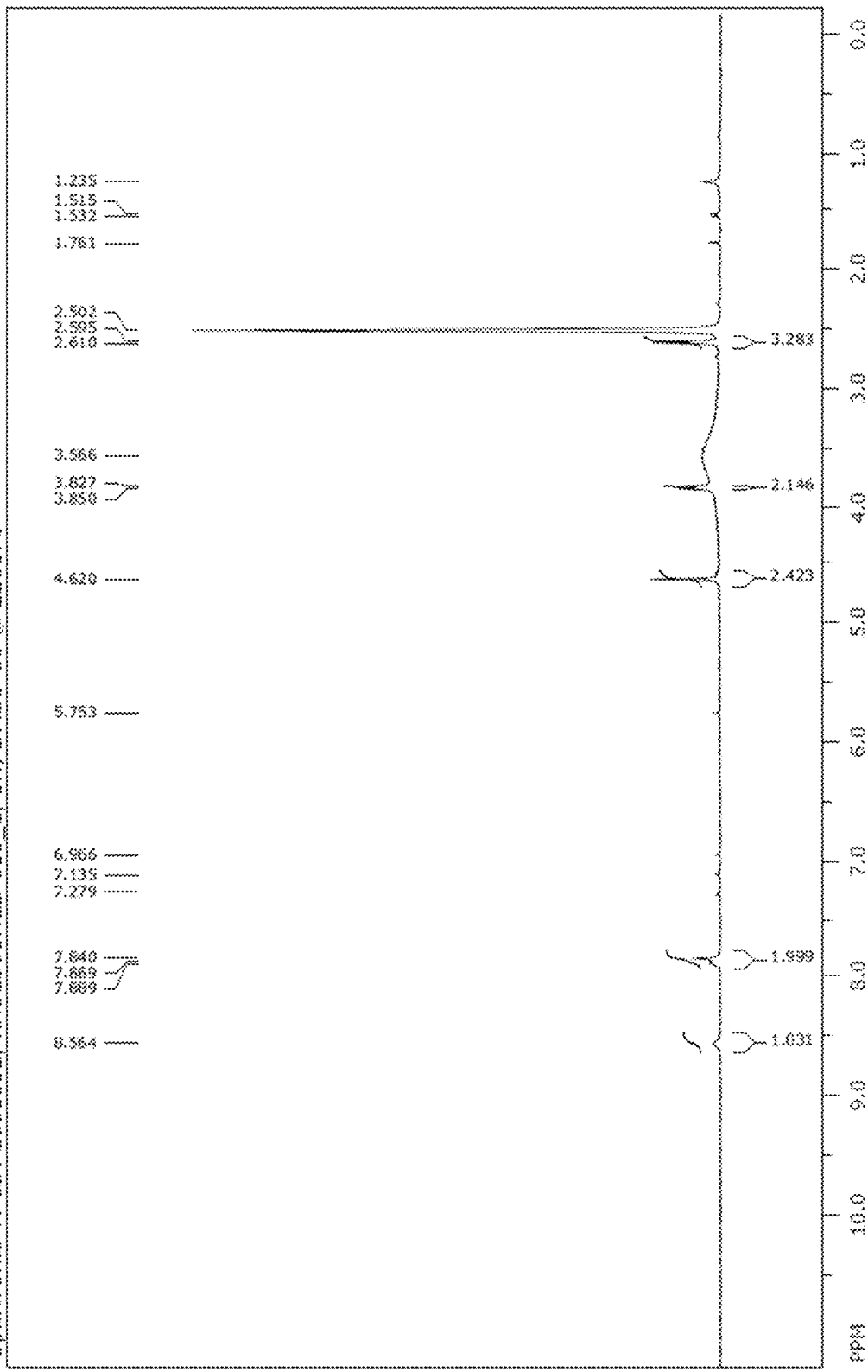
FIG. 2B, FIG. 2C, and FIG. 2D. $^1$H NMR, $^{13}$C NMR, and LC-MS Spectra of Comp 1.
Figure 2C:
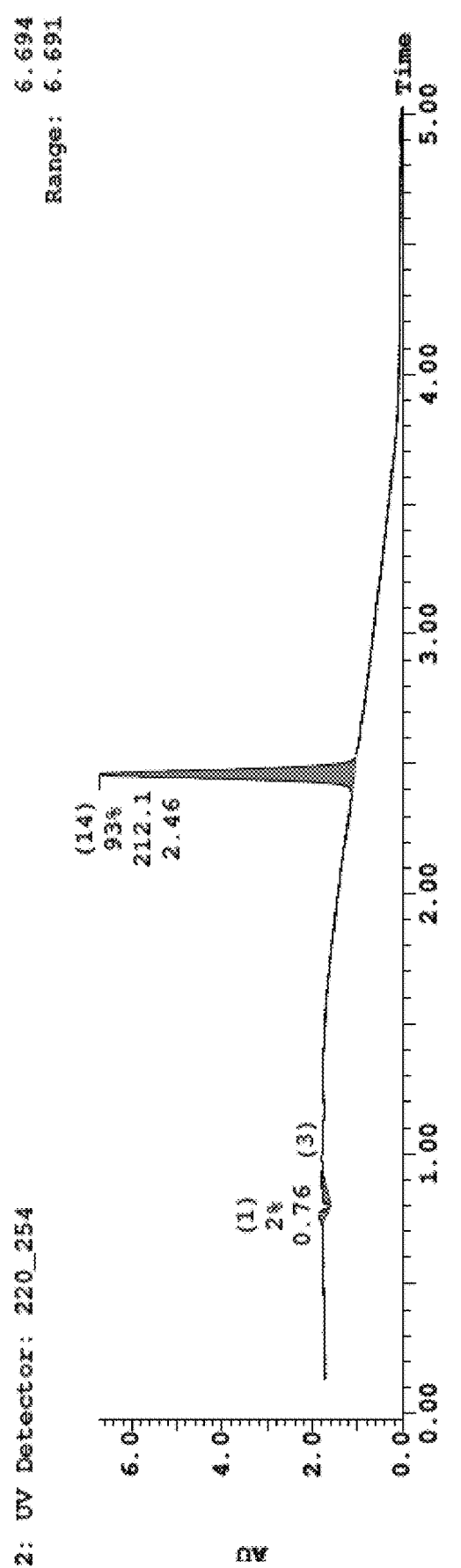
Figure 2D:
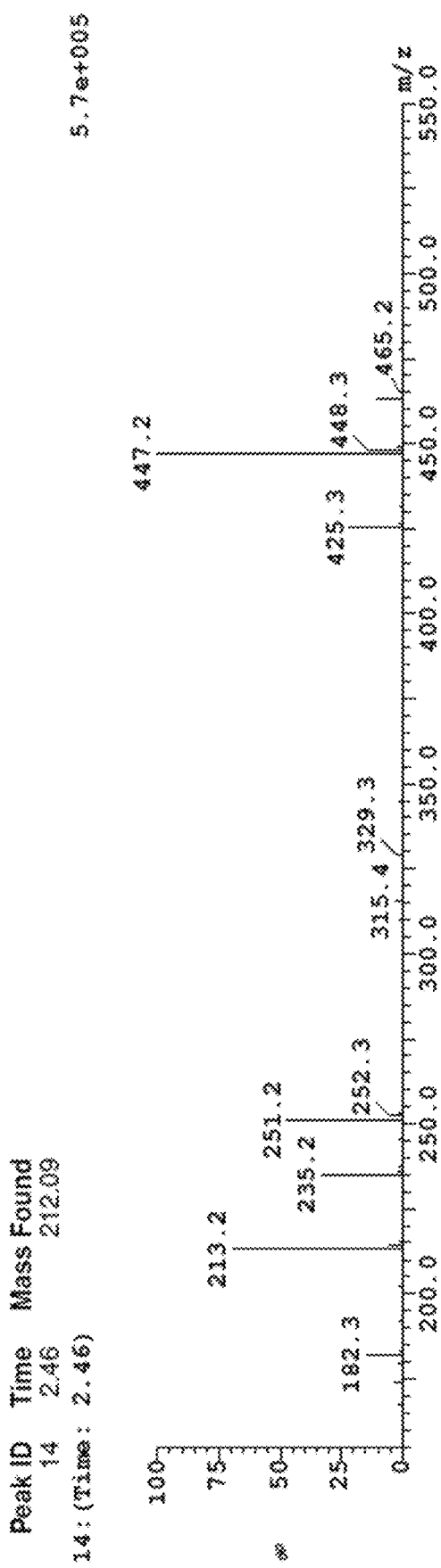
Figure 3A:
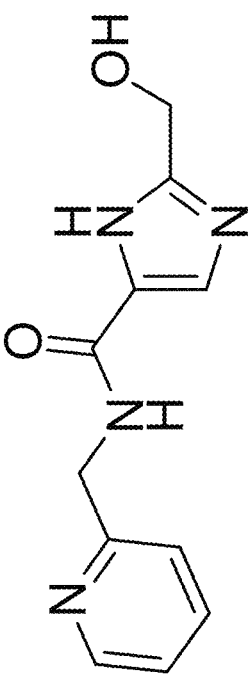
FIG. 3A. chemical structure of Comp. 2.
Figure 3B:
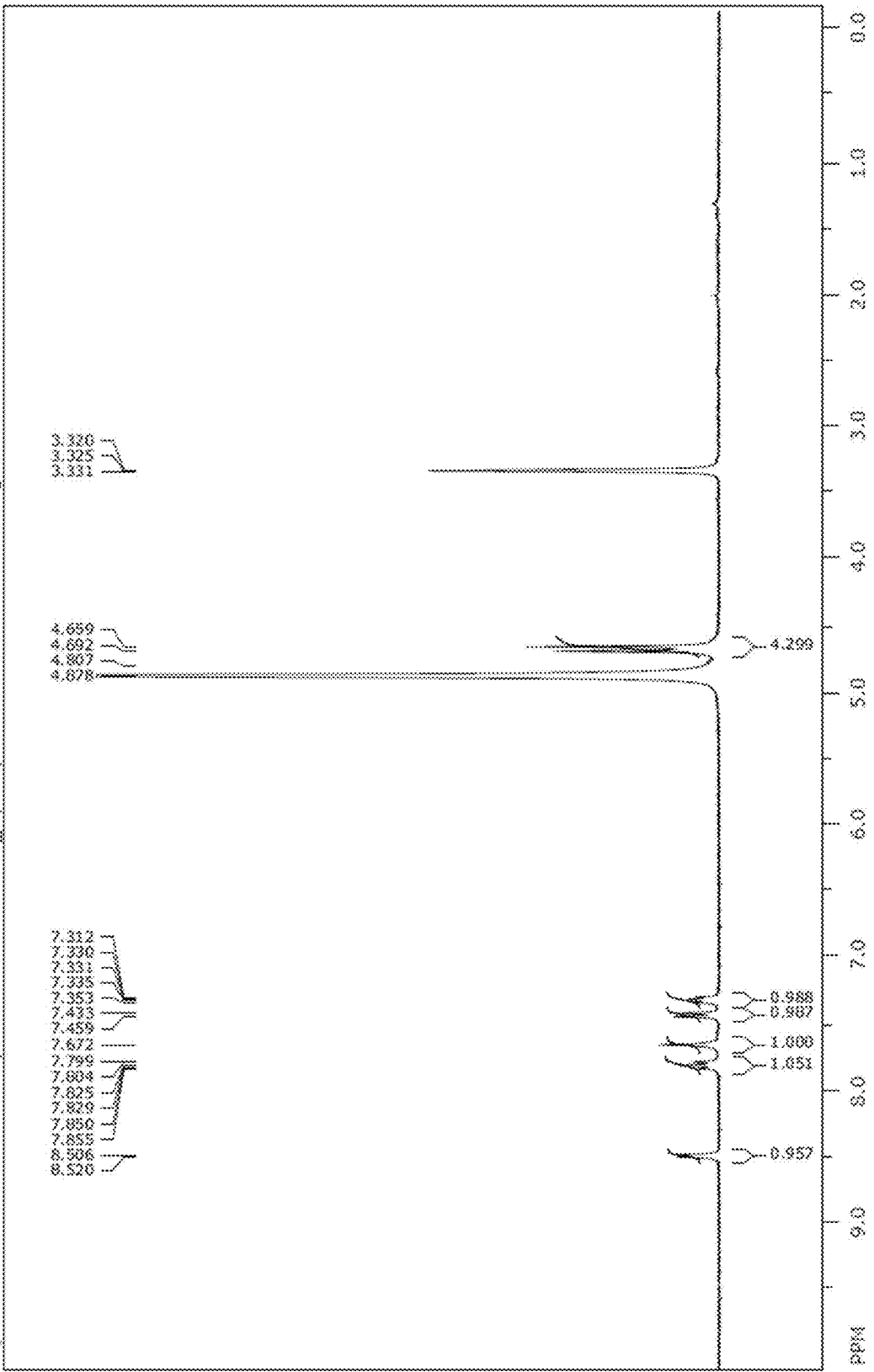
FIG. 3B, FIG. 3C, and FIG. 3D. $^1$H NMR, $^{13}$C NMR, and LC-MS Spectra of Comp 2.
Figure 3C:
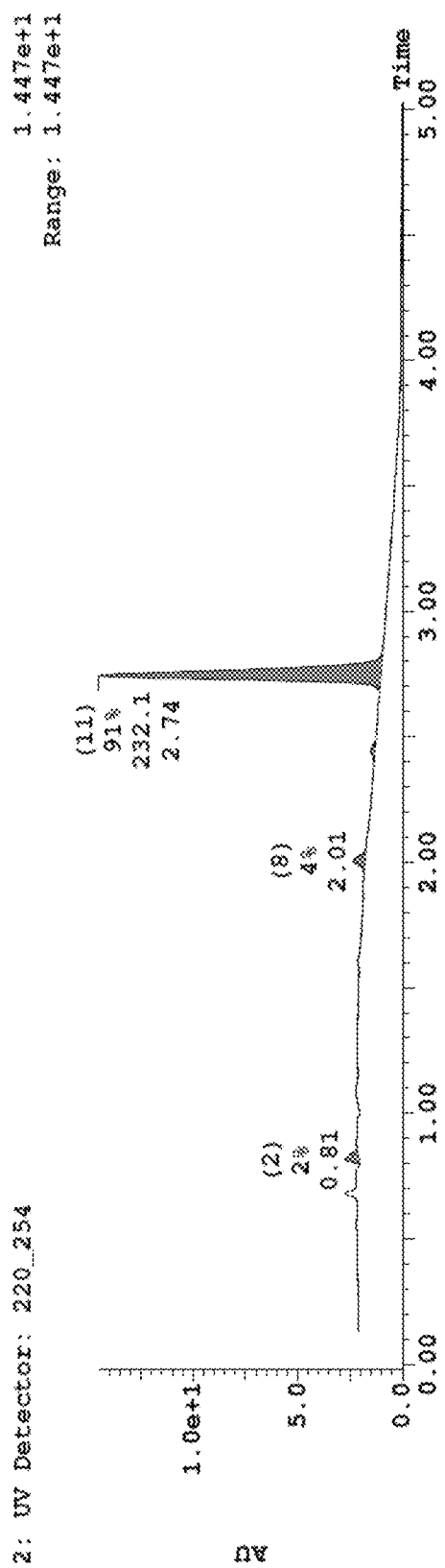
Figure 3D:
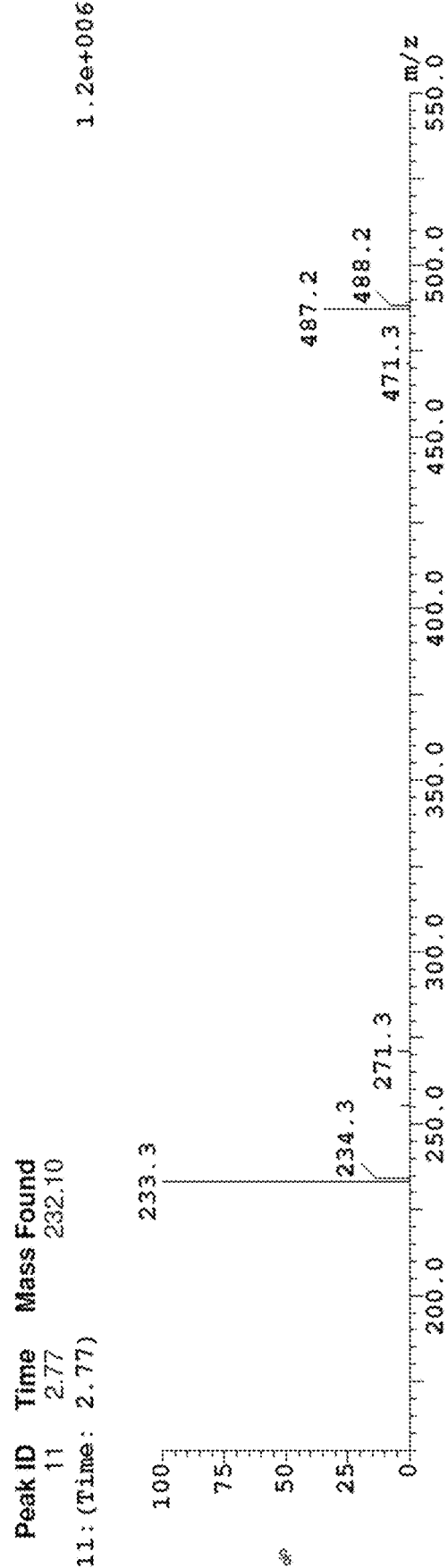
Figure 4A:
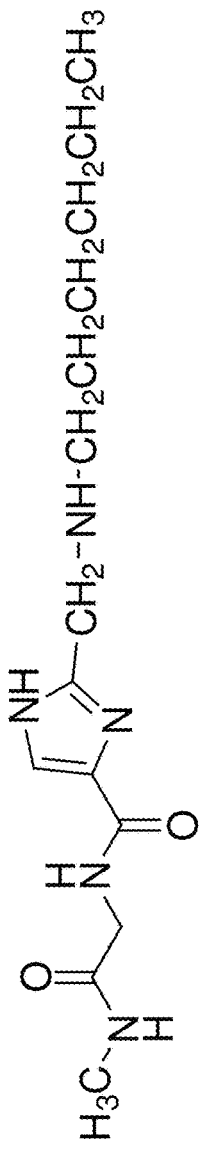
FIG. 4A. chemical structure of Comp. 3.
Figure 4B:
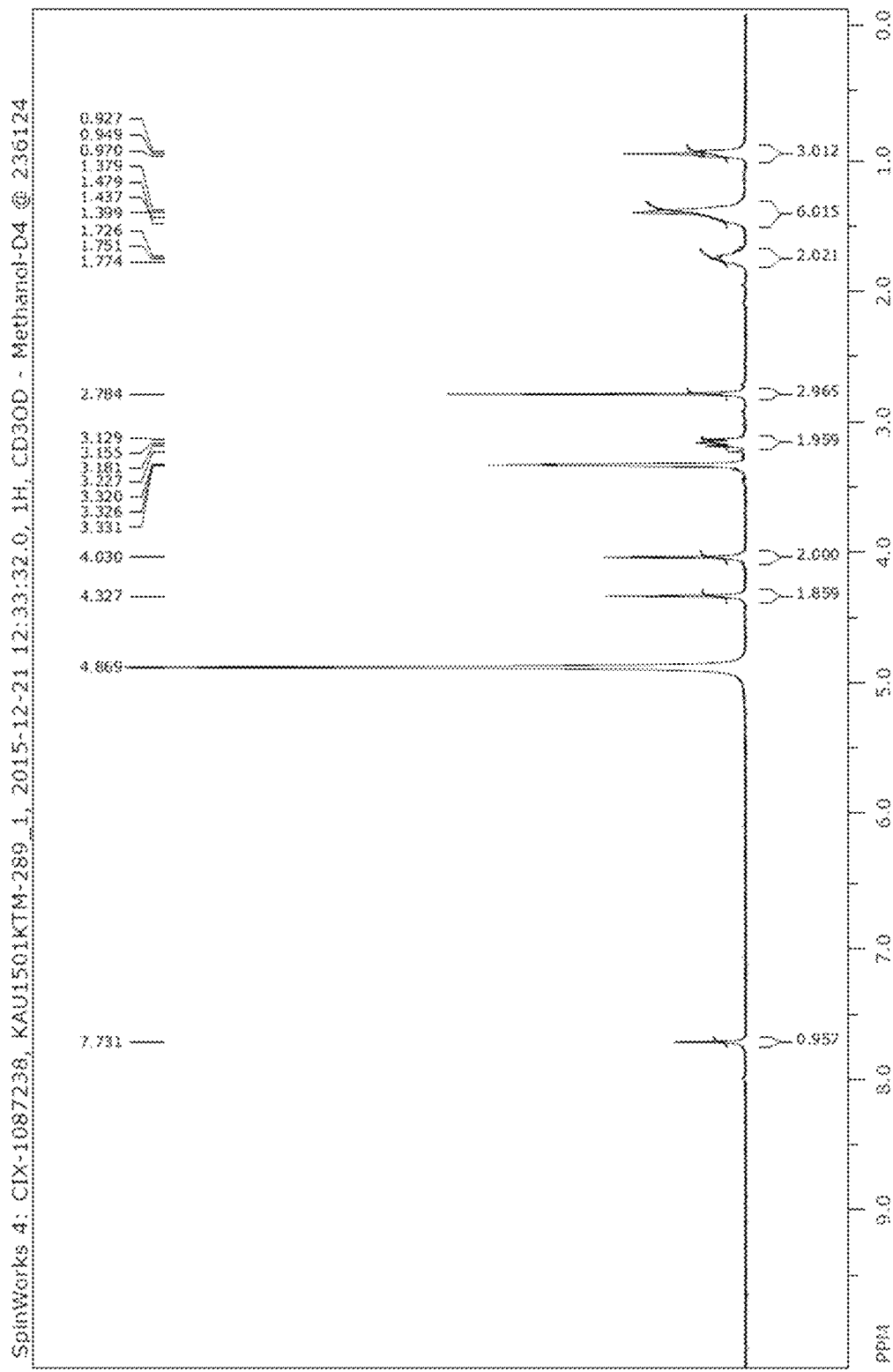
FIG. 4B, FIG. 4C, FIG. 4D, and FIG. 4E. $^1$H NMR, $^{13}$C NMR and LC-MS Spectra of Comp 3.
Figure 4C:
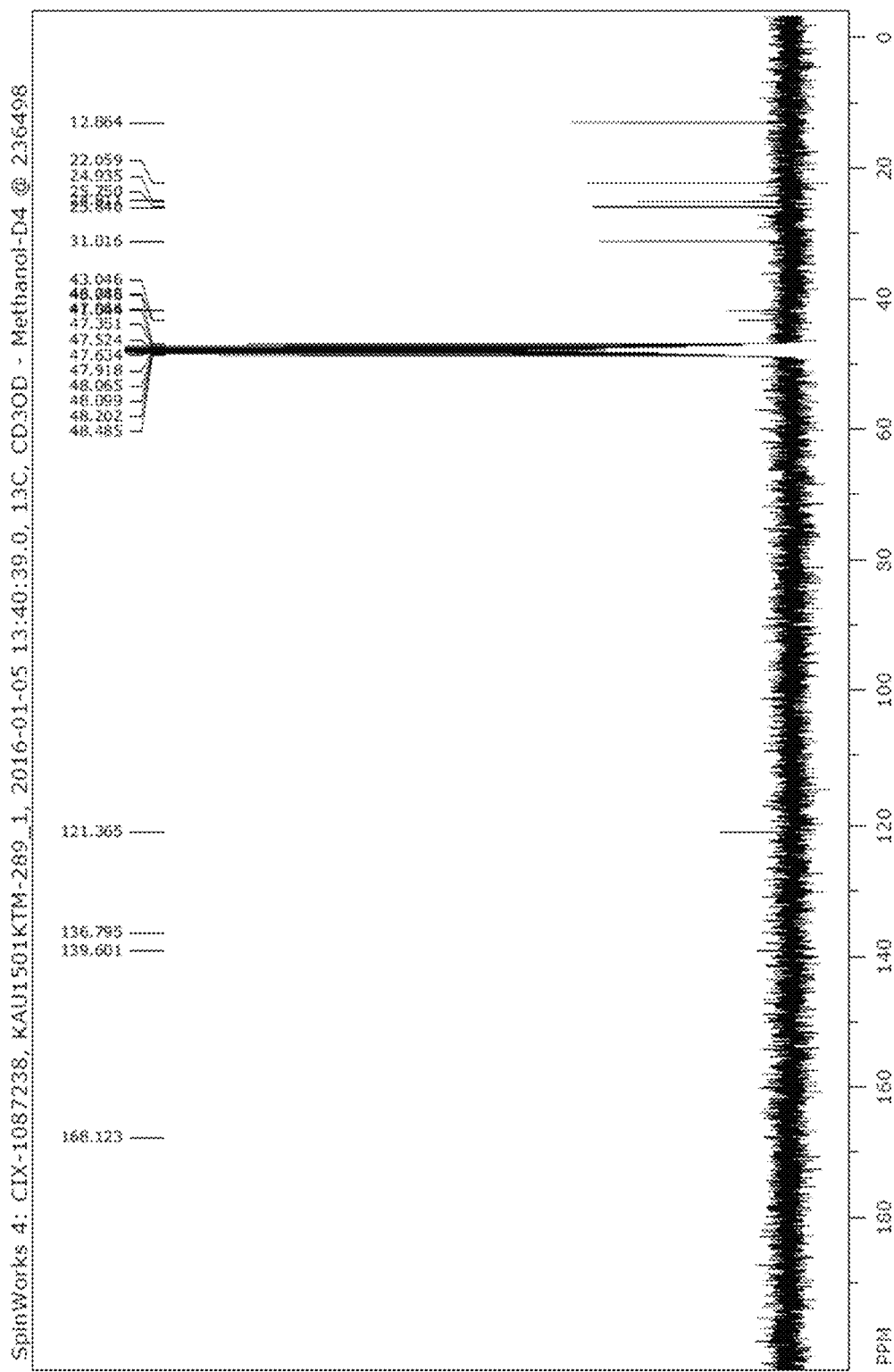
Figure 4D:
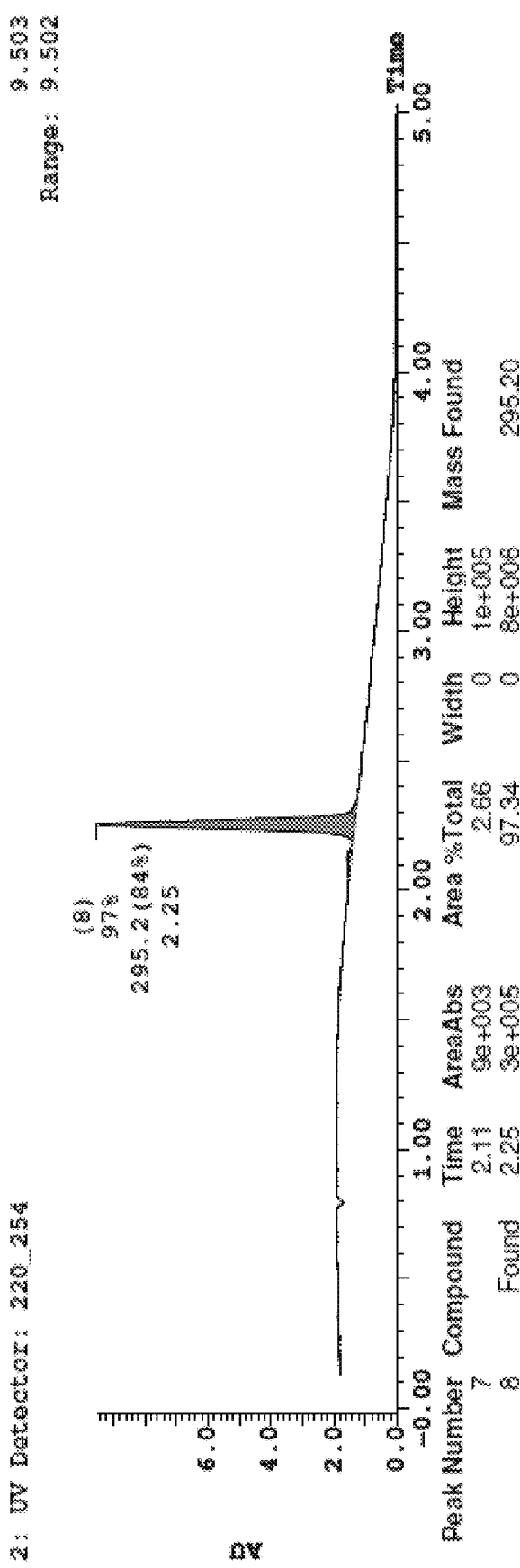
Figure 4E:
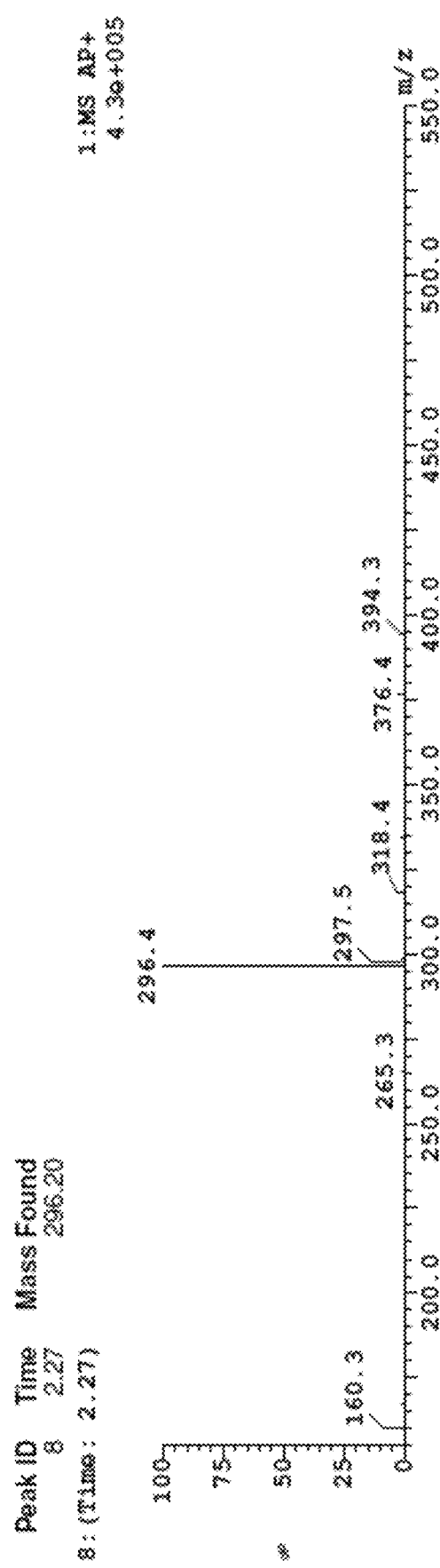
Figure 5A:
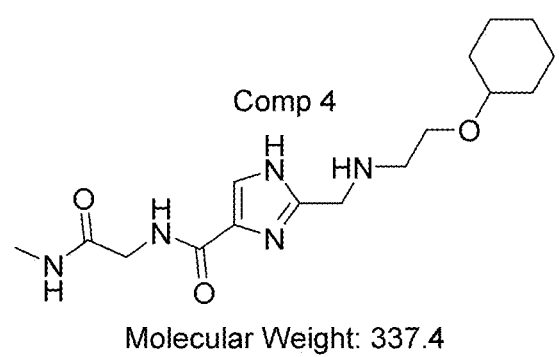
FIG. 5A. chemical structure of Comp. 4.
Figure 5B:
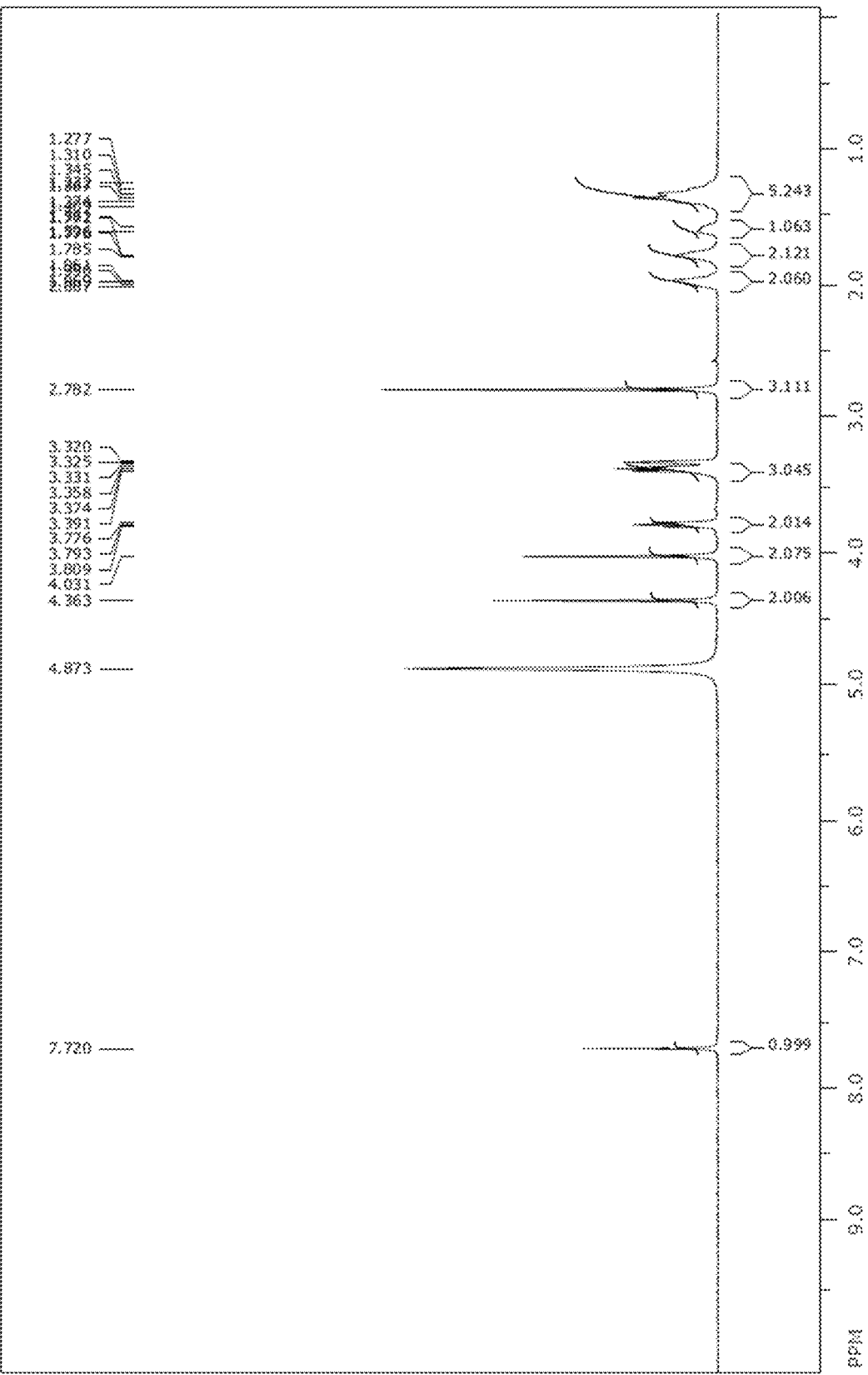
FIG. 5B, FIG. 5C, FIG. 5D, and FIG. 5E. $^1$H NMR, $^{13}$C NMR and LC-MS Spectra of Comp 4.
Figure 5C:
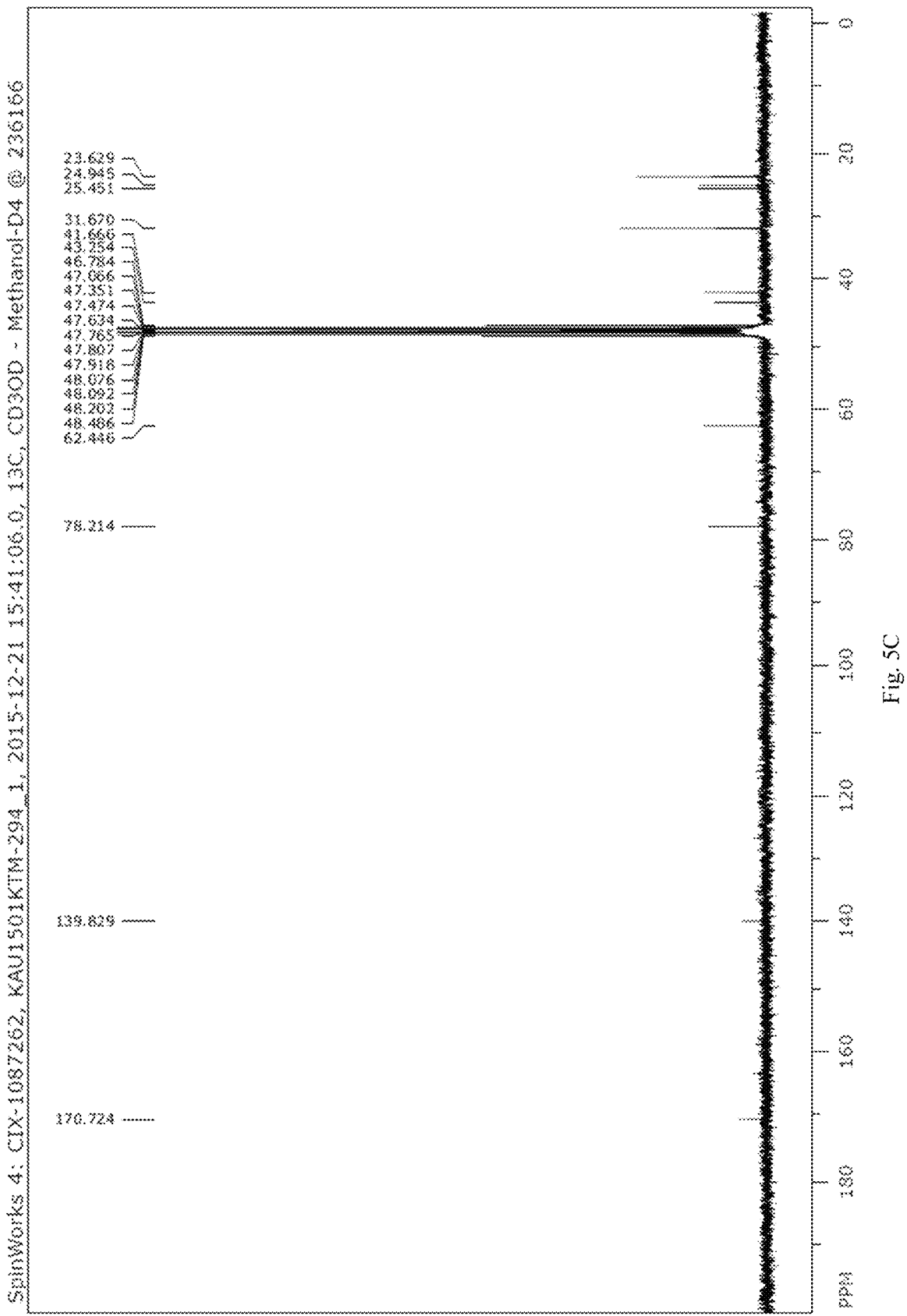
Figure 5D:
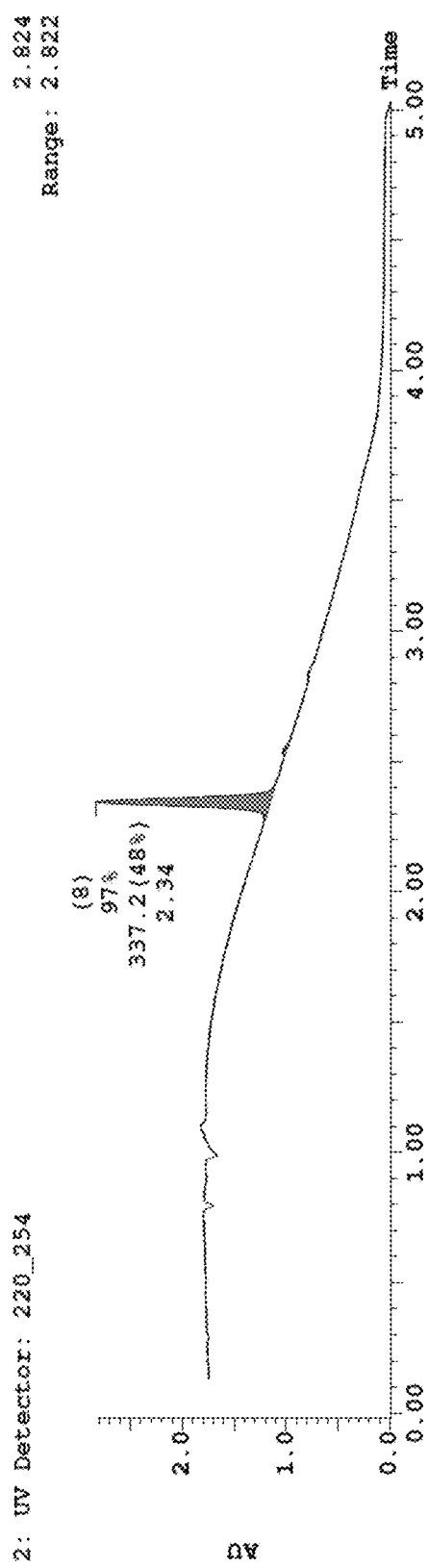
Figure 5E:
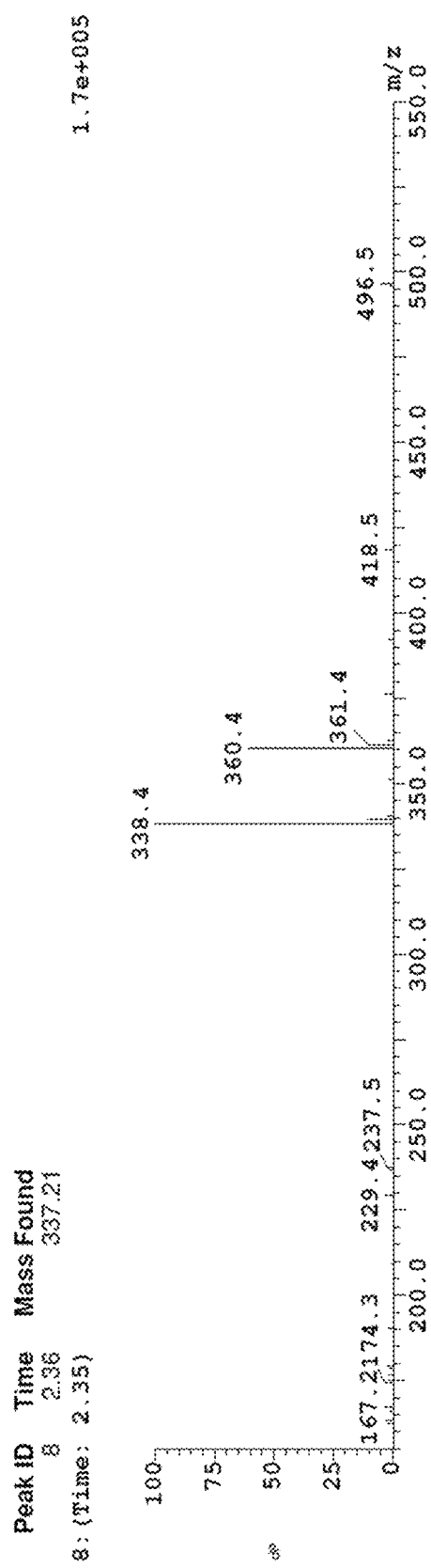
Figure 6A:
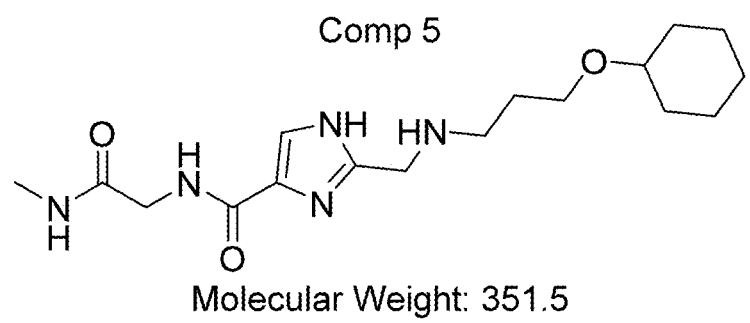
FIG. 6A. chemical structure of Comp. 5.
Figure 6B:
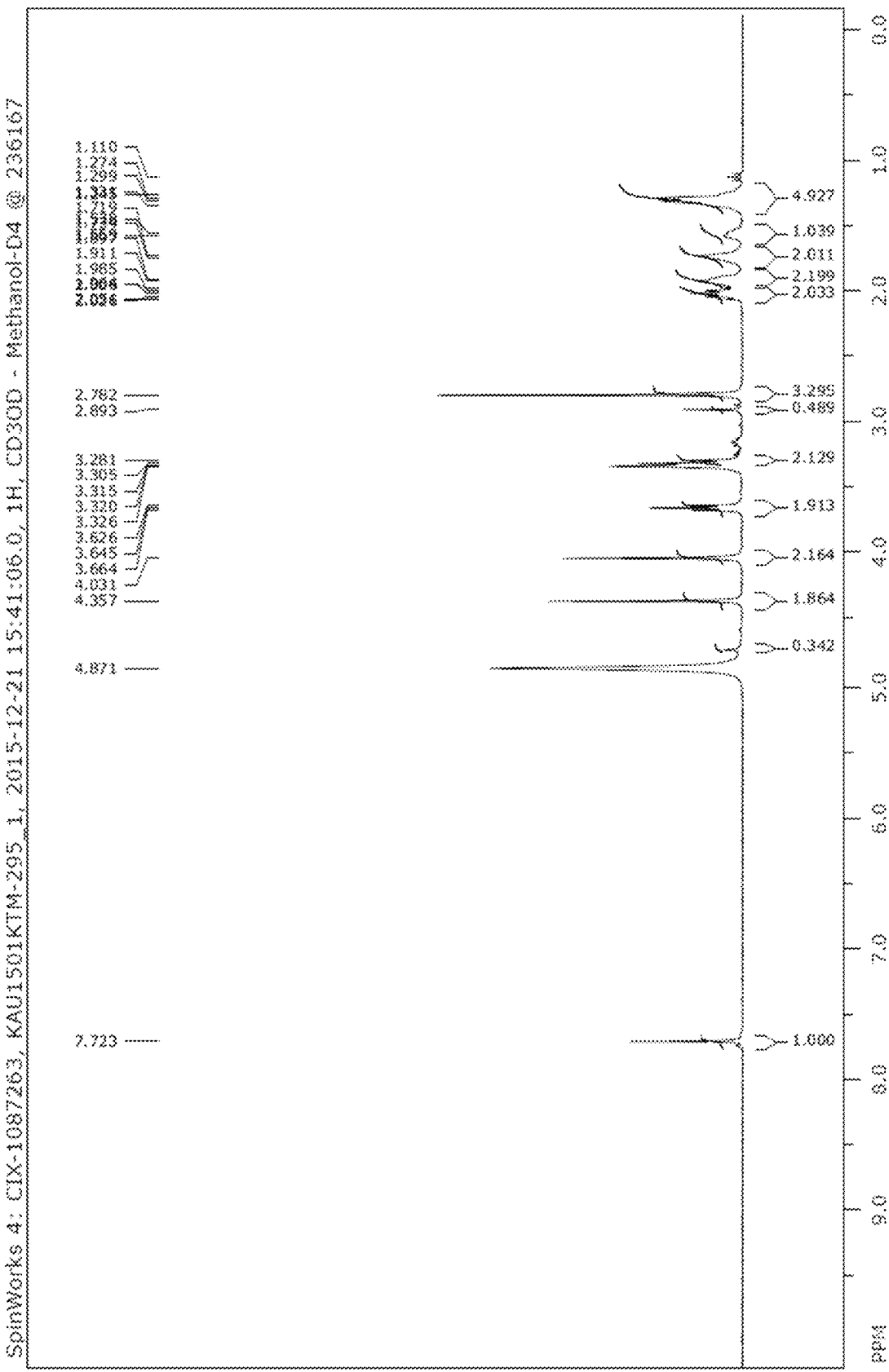
FIG. 6B, FIG. 6C, FIG. 6D, and FIG. 6E. $^1$H NMR, $^{13}$C NMR and LC-MS Spectra of Comp 5.
Figure 6C:
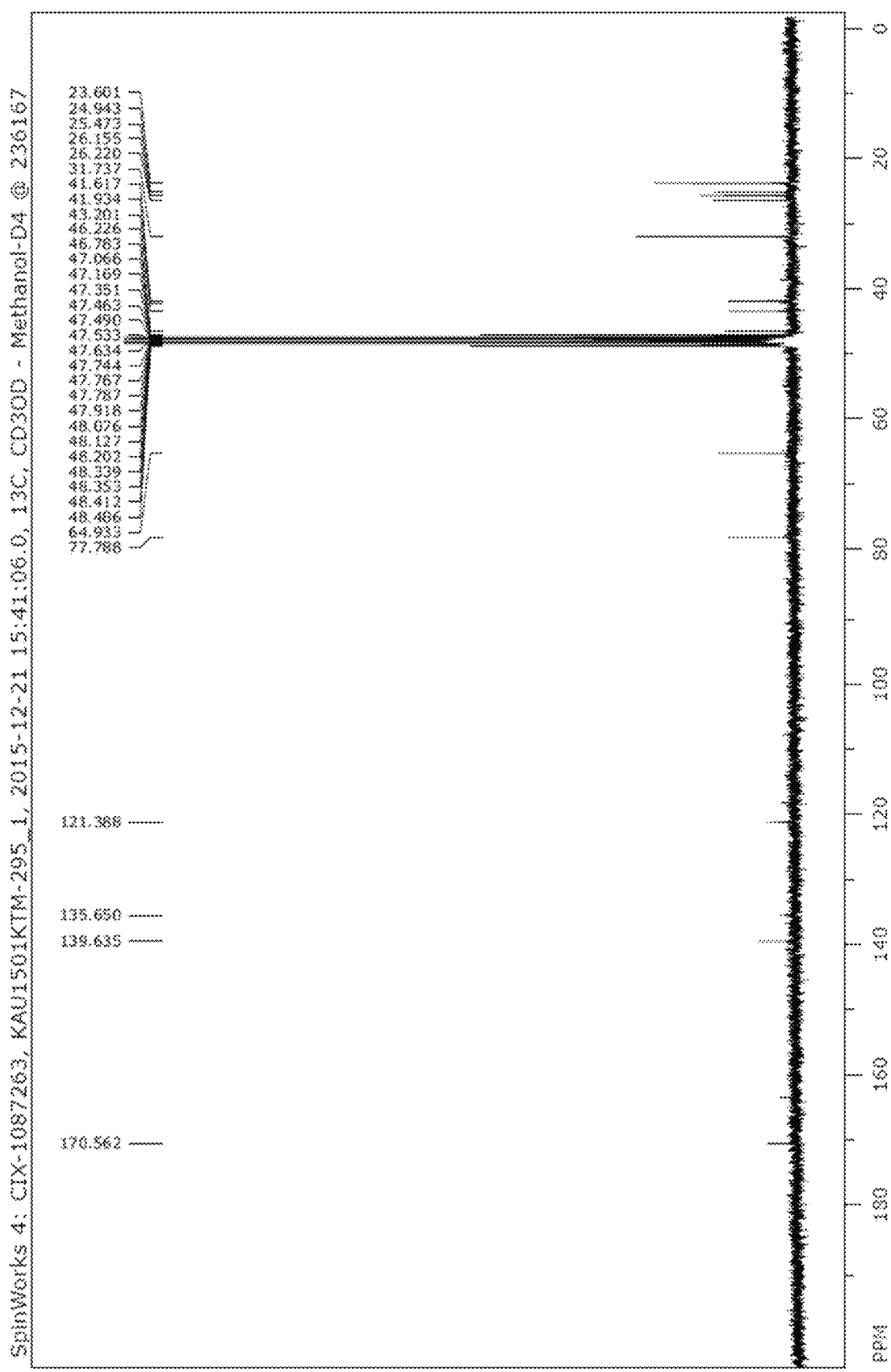
Figure 6D:
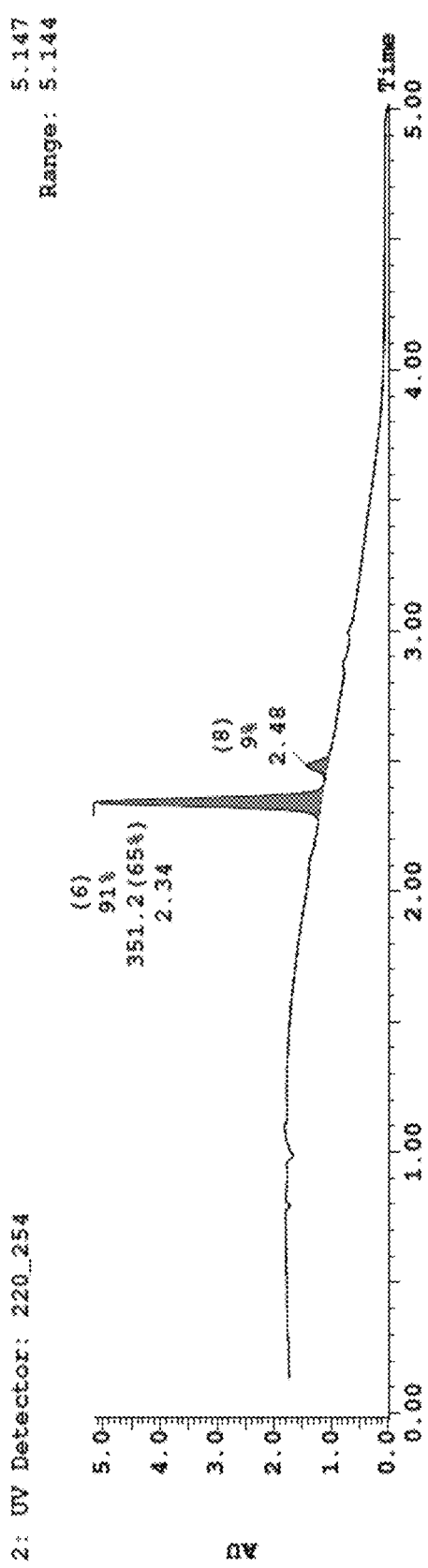
Figure 6E:
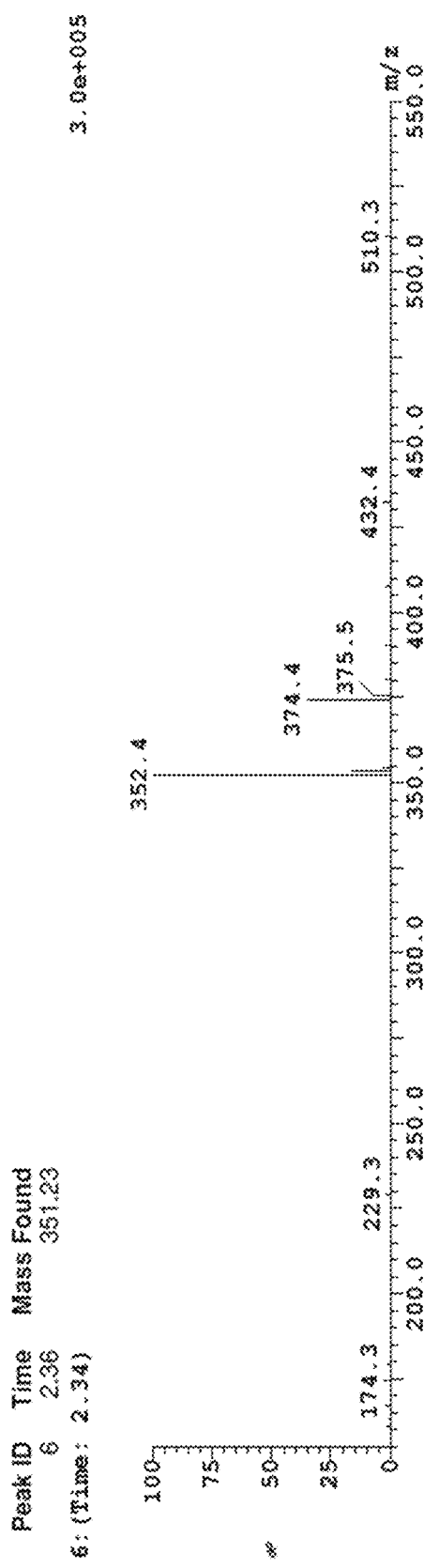
Figure 7A:
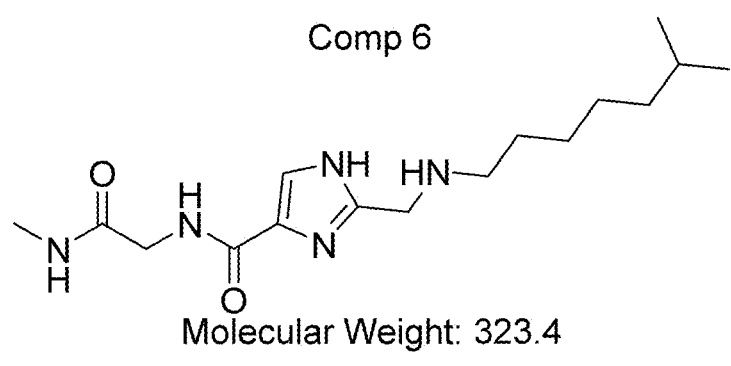
FIG. 7A. chemical structure of Comp. 6.
Figure 7B:
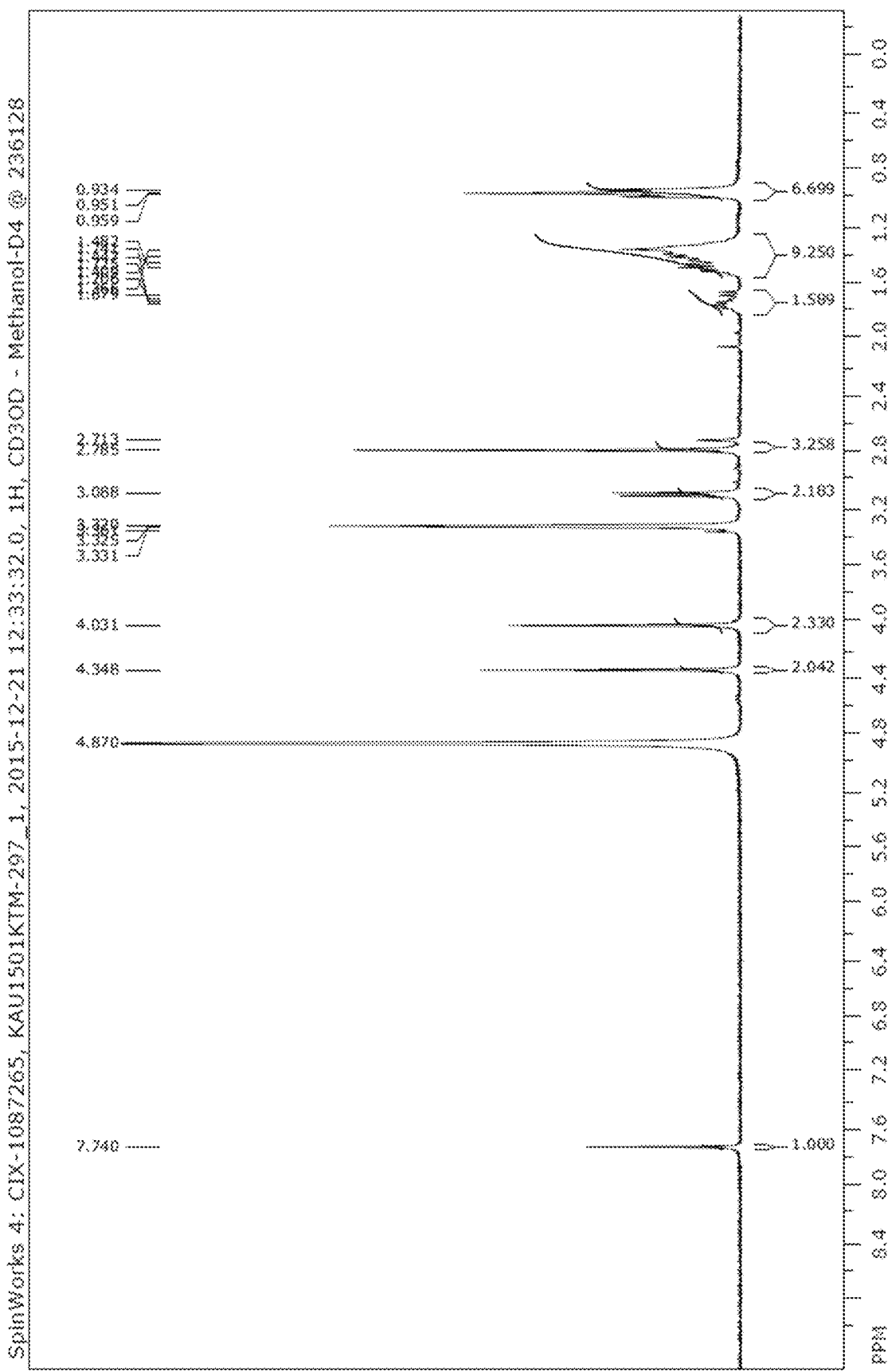
FIG. 7B, FIG. 7C, FIG. 7D and FIG. 7E. $^1$H NMR, $^{13}$C NMR and LC-MS Spectra of Comp 6.
Figure 7C:
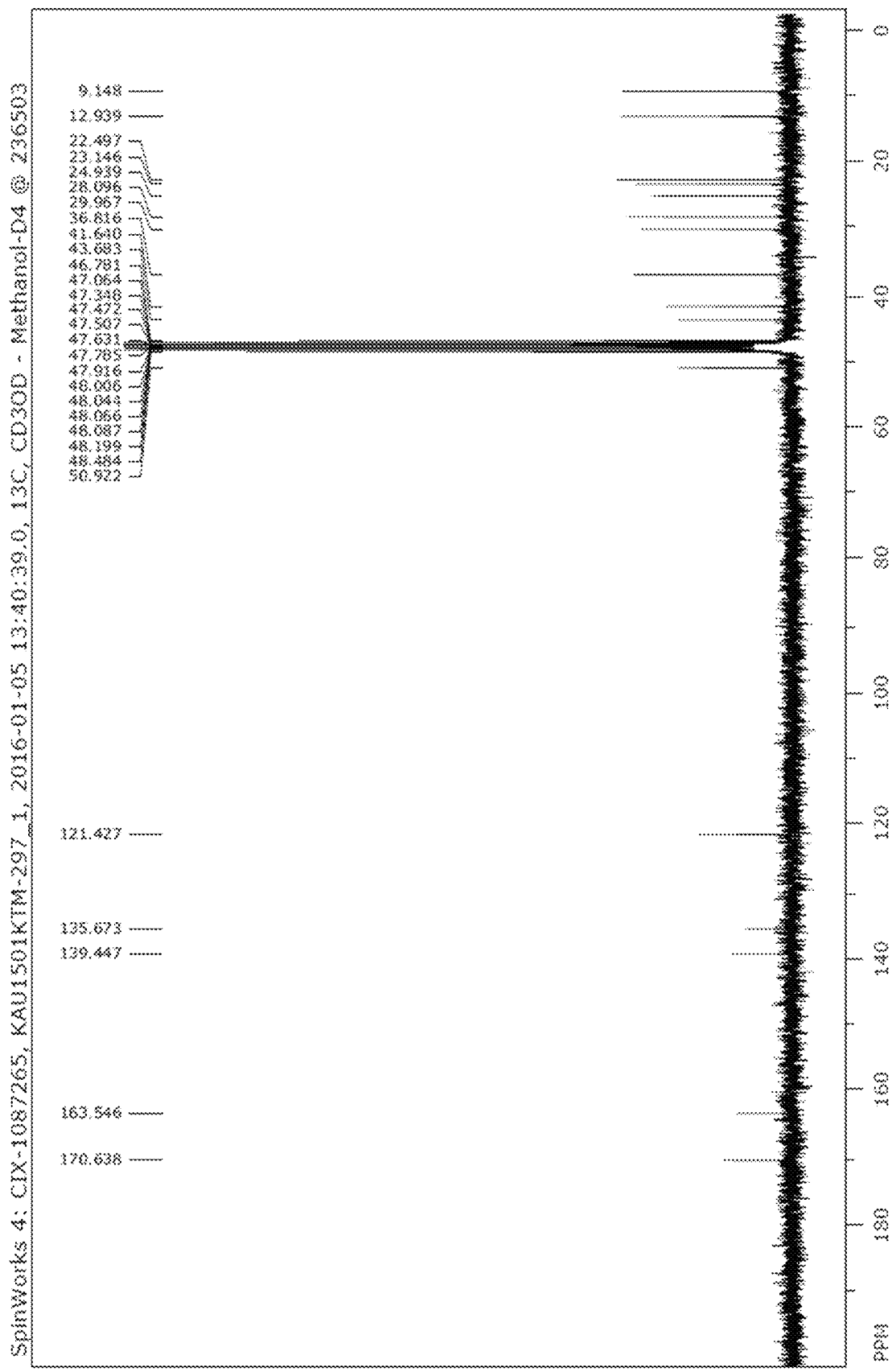
Figure 7D:
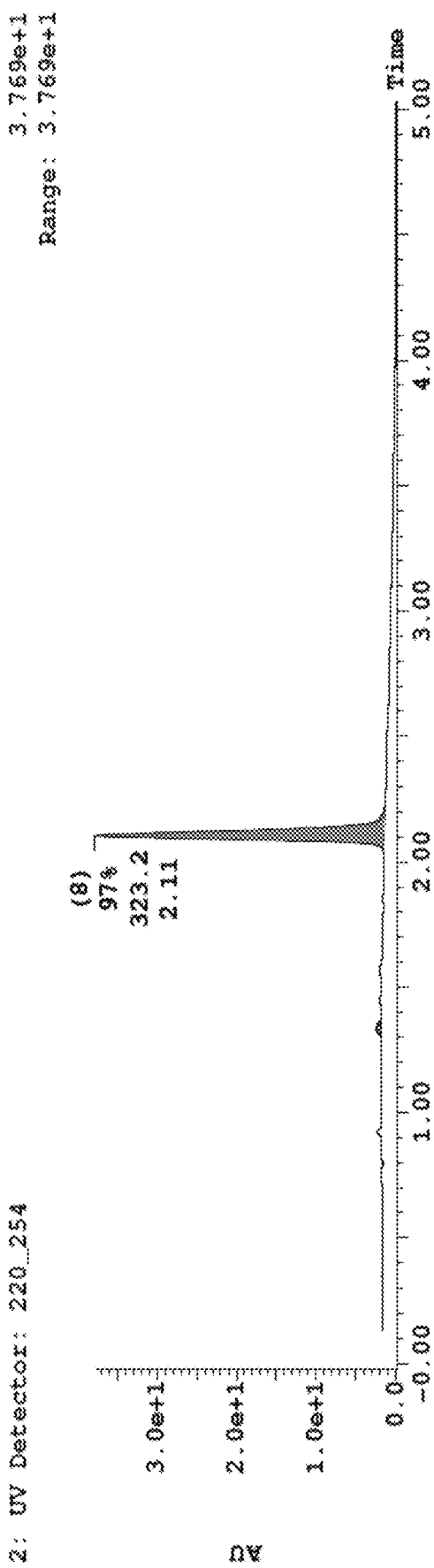
Figure 7E:
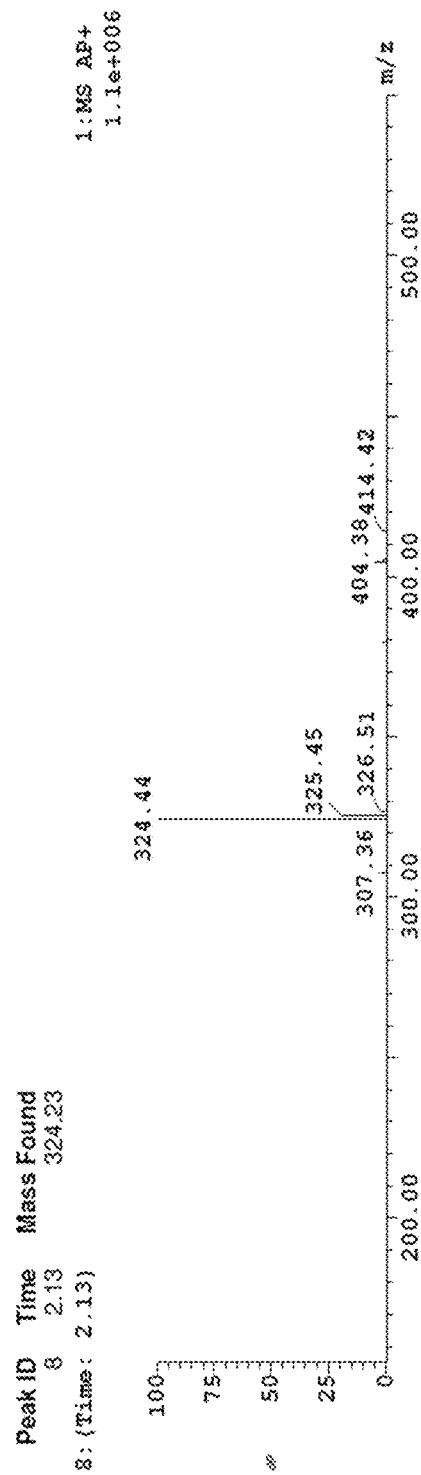
Figure 8A:
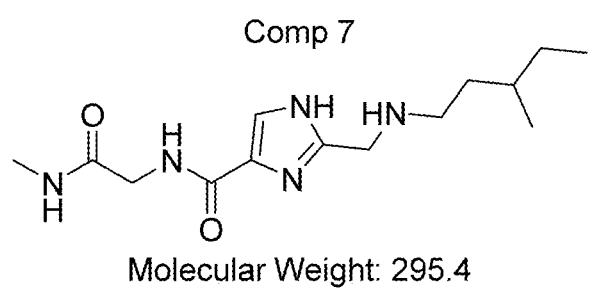
FIG. 8A. chemical structure of Comp. 7.
Figure 8B:
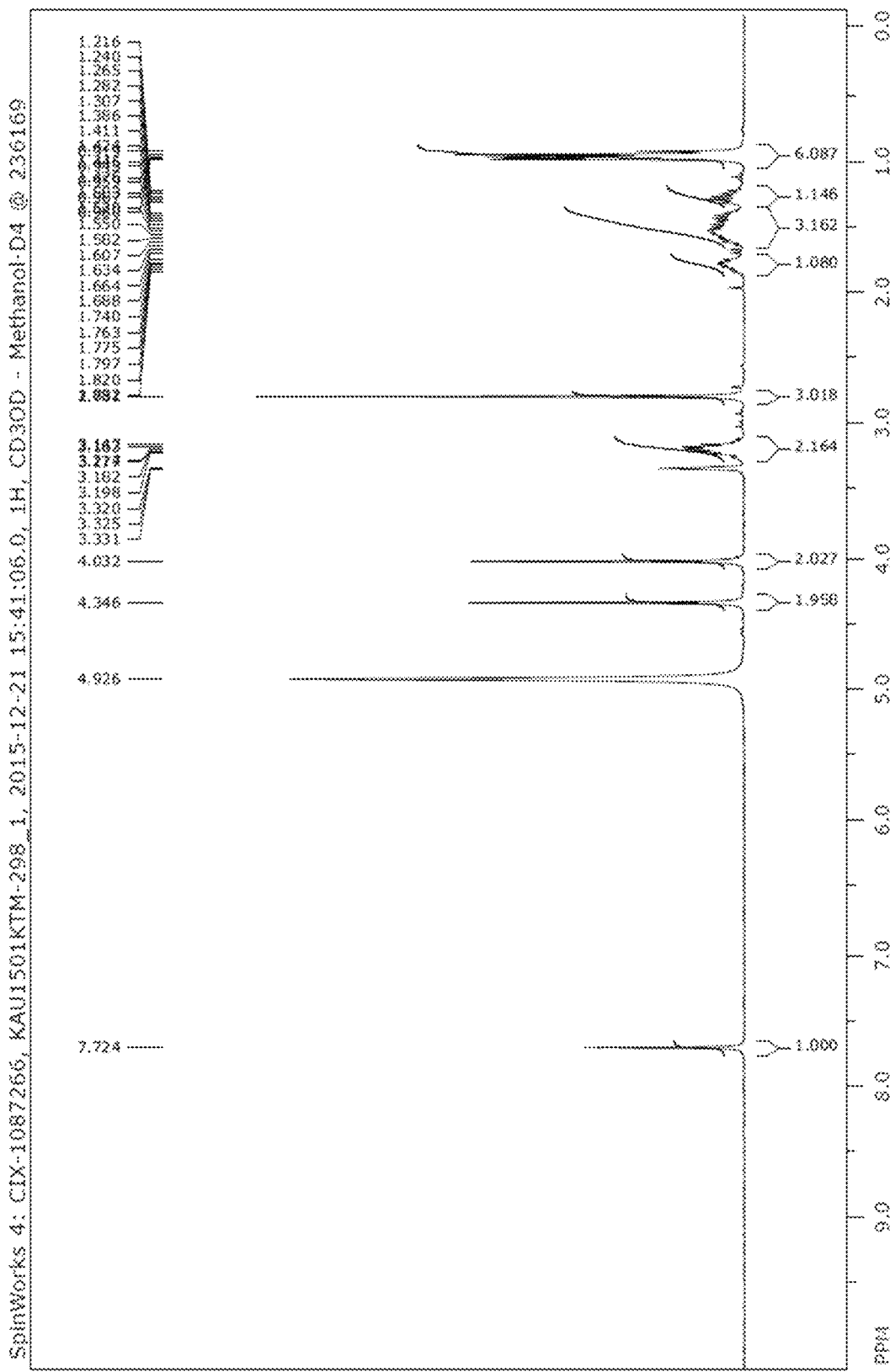
FIG. 8B, FIG. 8C, FIG. 8D, and FIG. 8E. $^1$H NMR, $^{13}$C NMR and LC-MS Spectra of Comp 7.
Figure 8C:
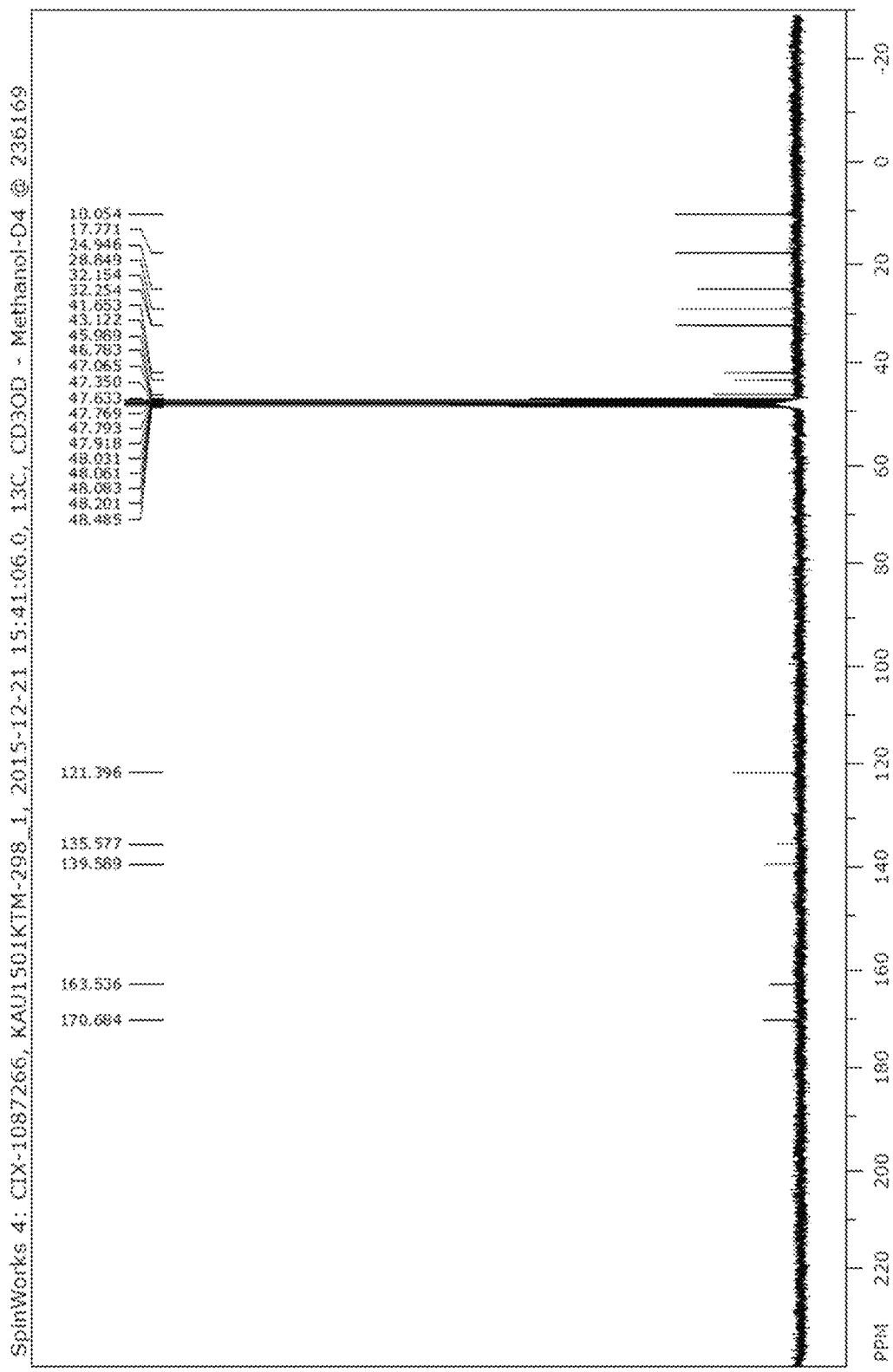
Figure 8D:
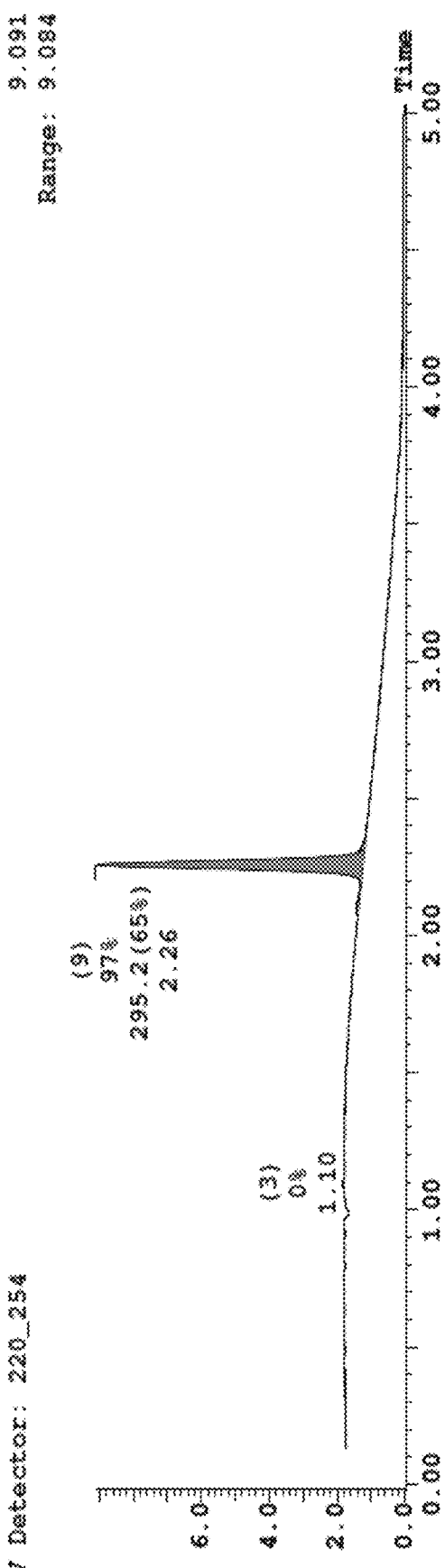
Figure 8E:
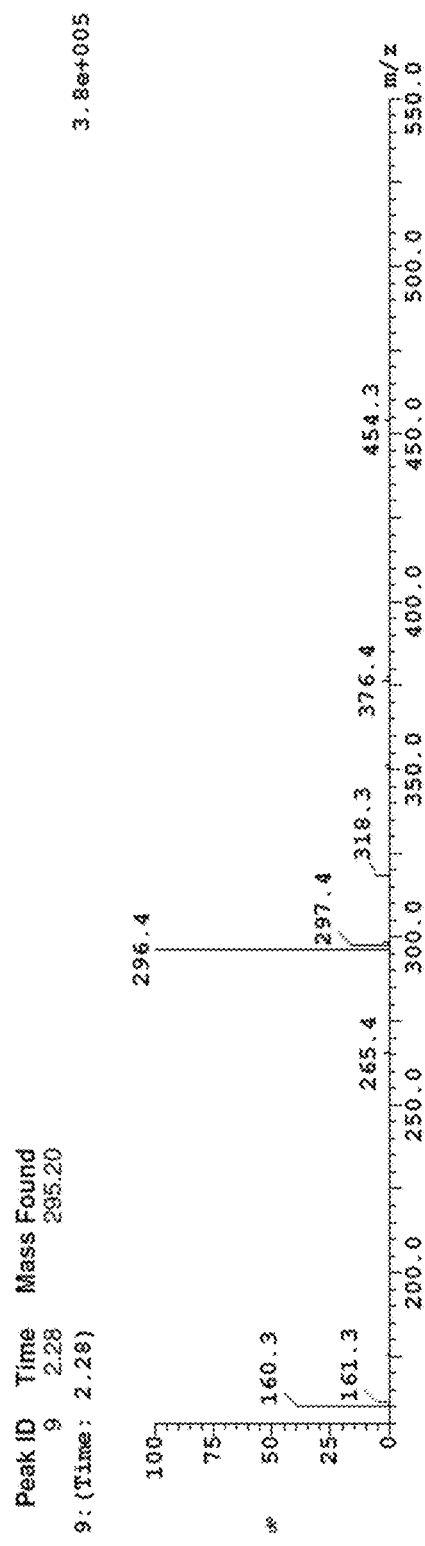
Figure 9A:
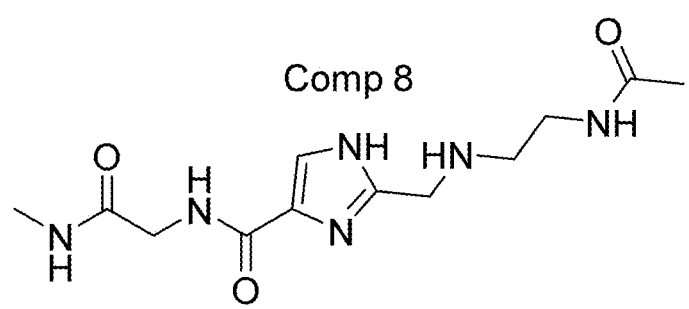
FIG. 9A. chemical structure of Comp. 8.
Figure 9B:
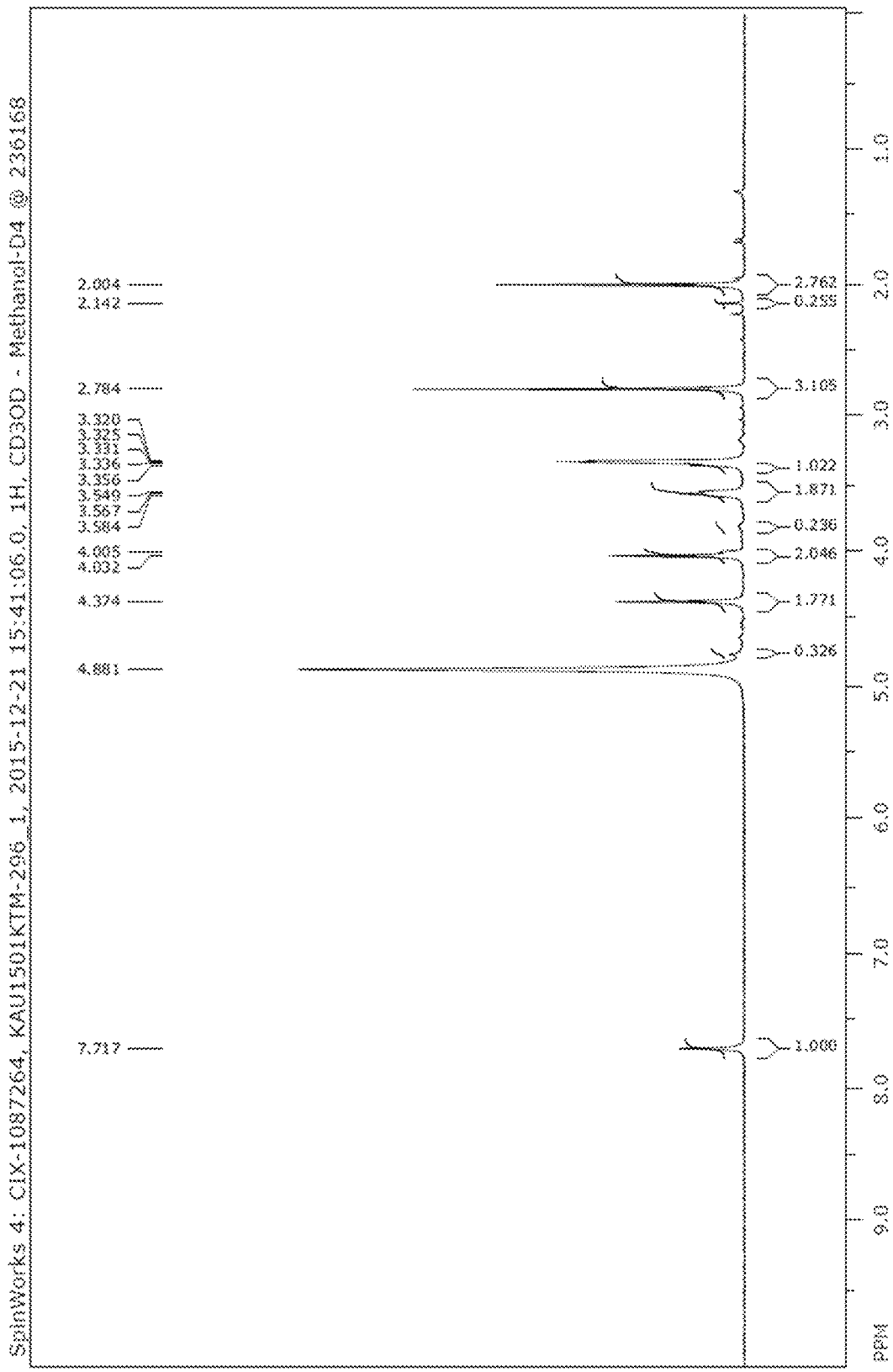
FIG. 9B, FIG. 9C, FIG. 9D, and FIG. 9E. $^1$H NMR, $^{13}$C NMR and LC-MS Spectra of Comp 8.
Figure 9C:
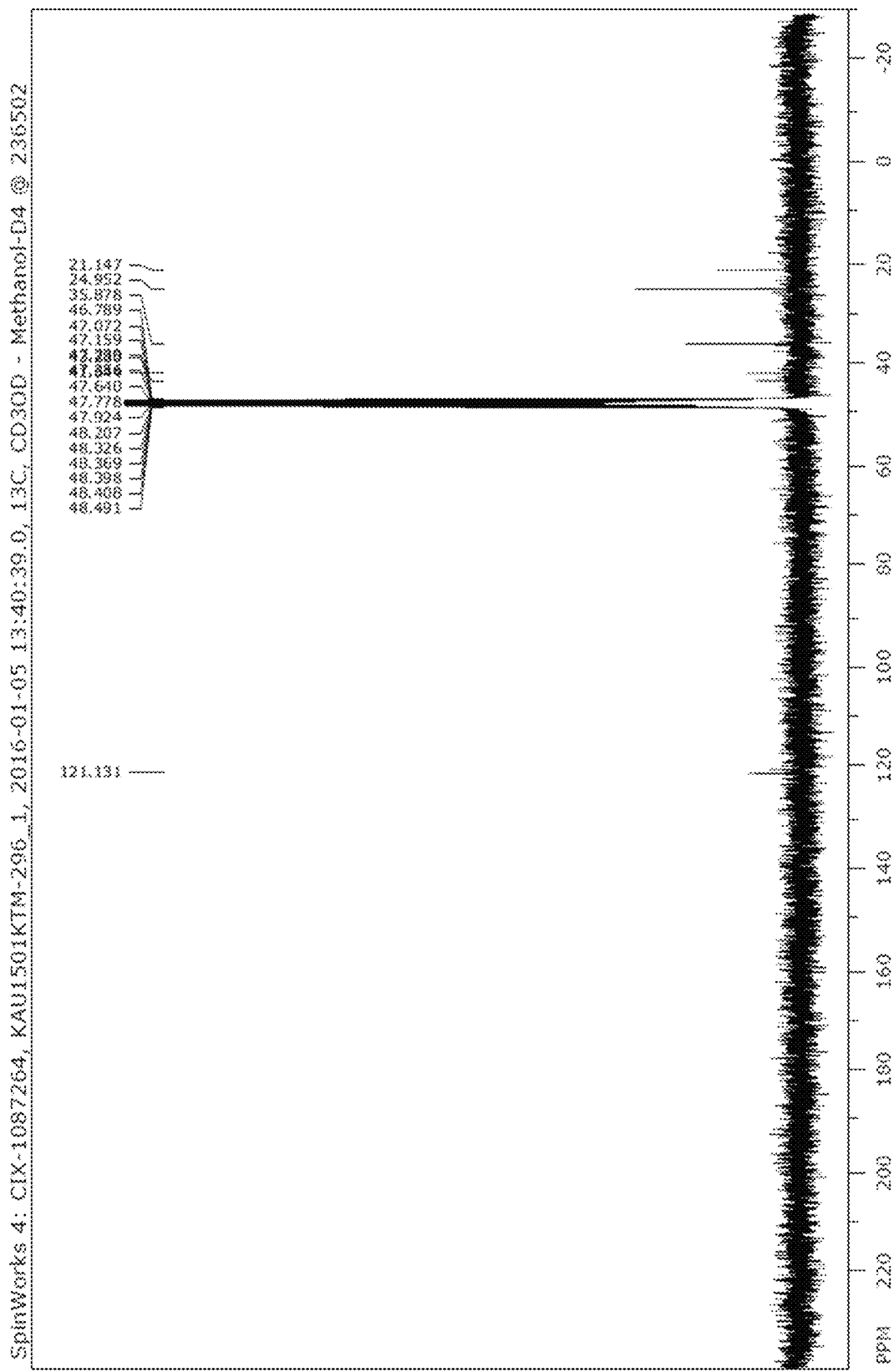
Figure 9D:
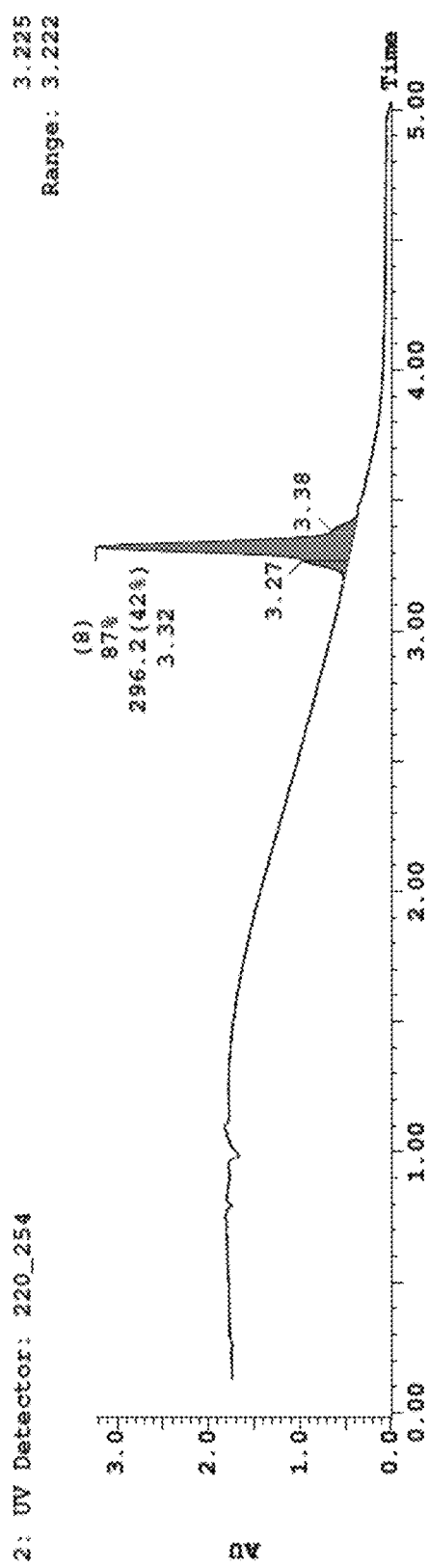
Figure 9E:
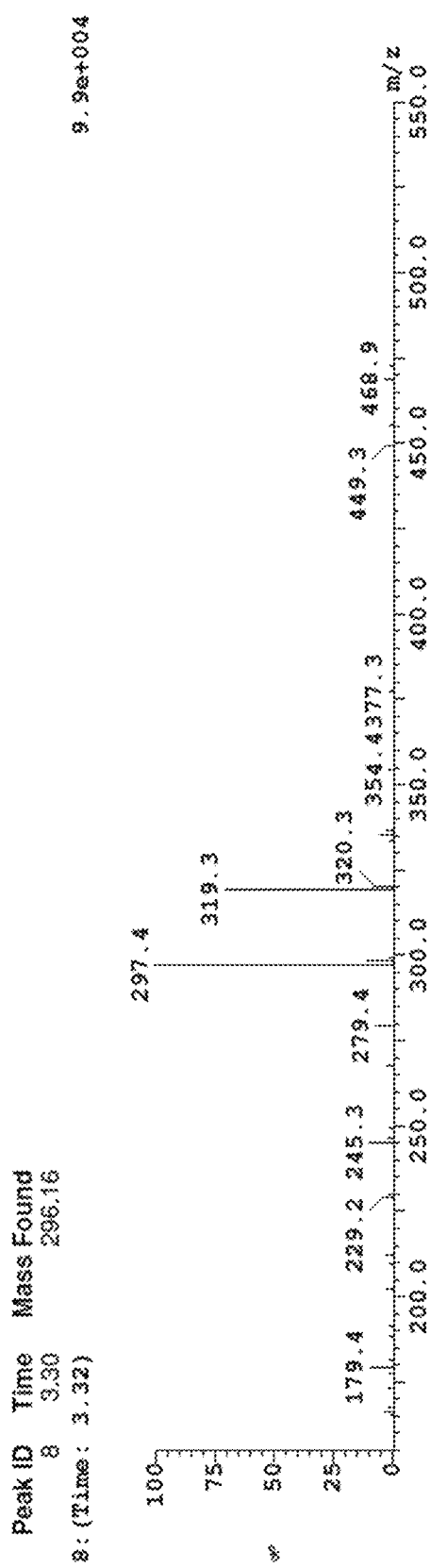
Figure 10A:
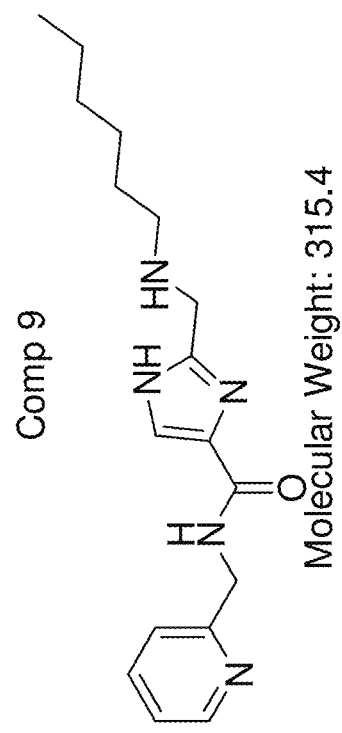
FIG. 10A. chemical structure of Comp. 9.
Figure 10B:
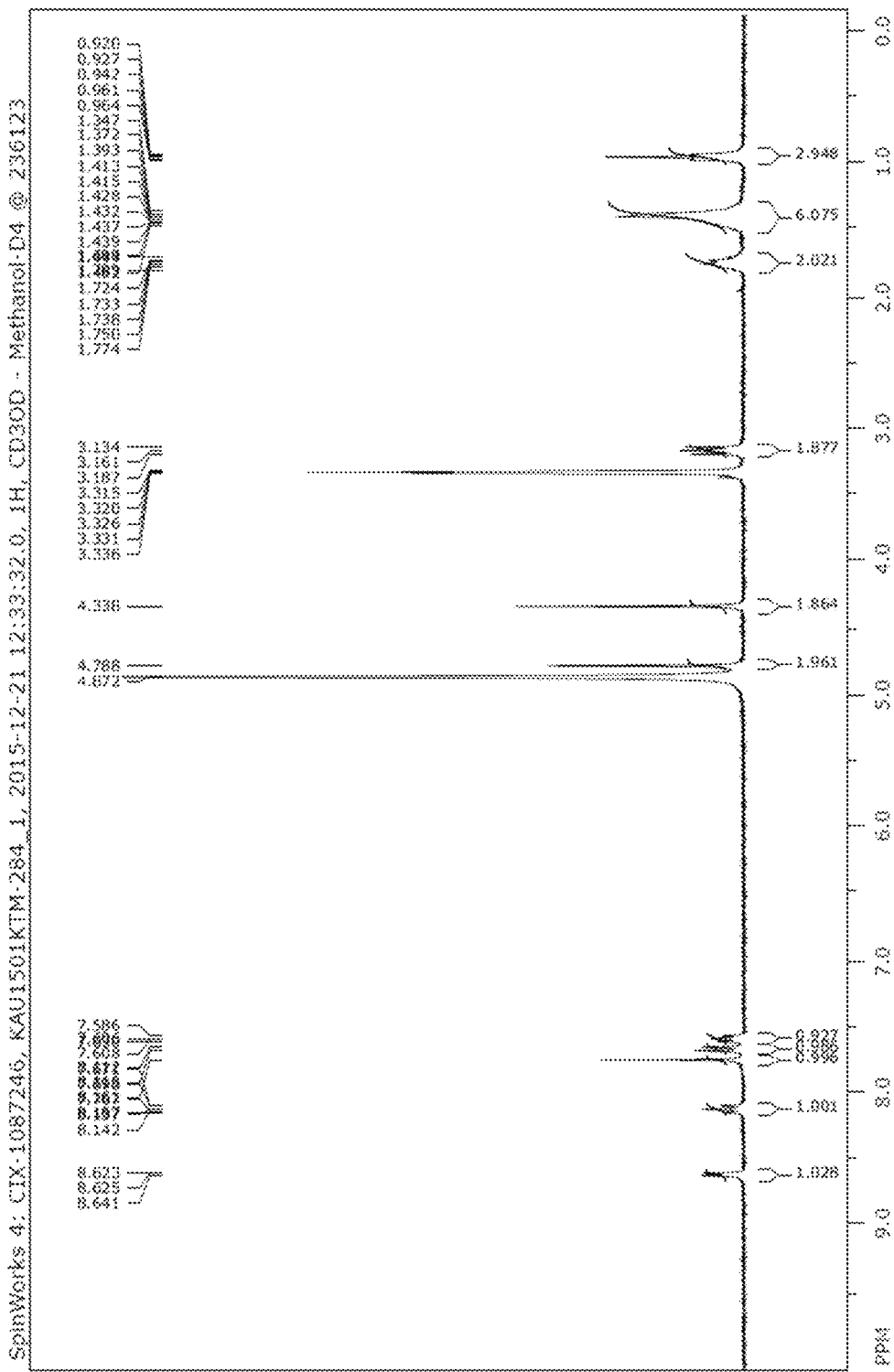
FIG. 10B, FIG. 10C, FIG. 10D, and FIG. 10E. $^1$H NMR, $^{13}$C NMR and LC-MS Spectra of Comp 9.
Figure 10C:
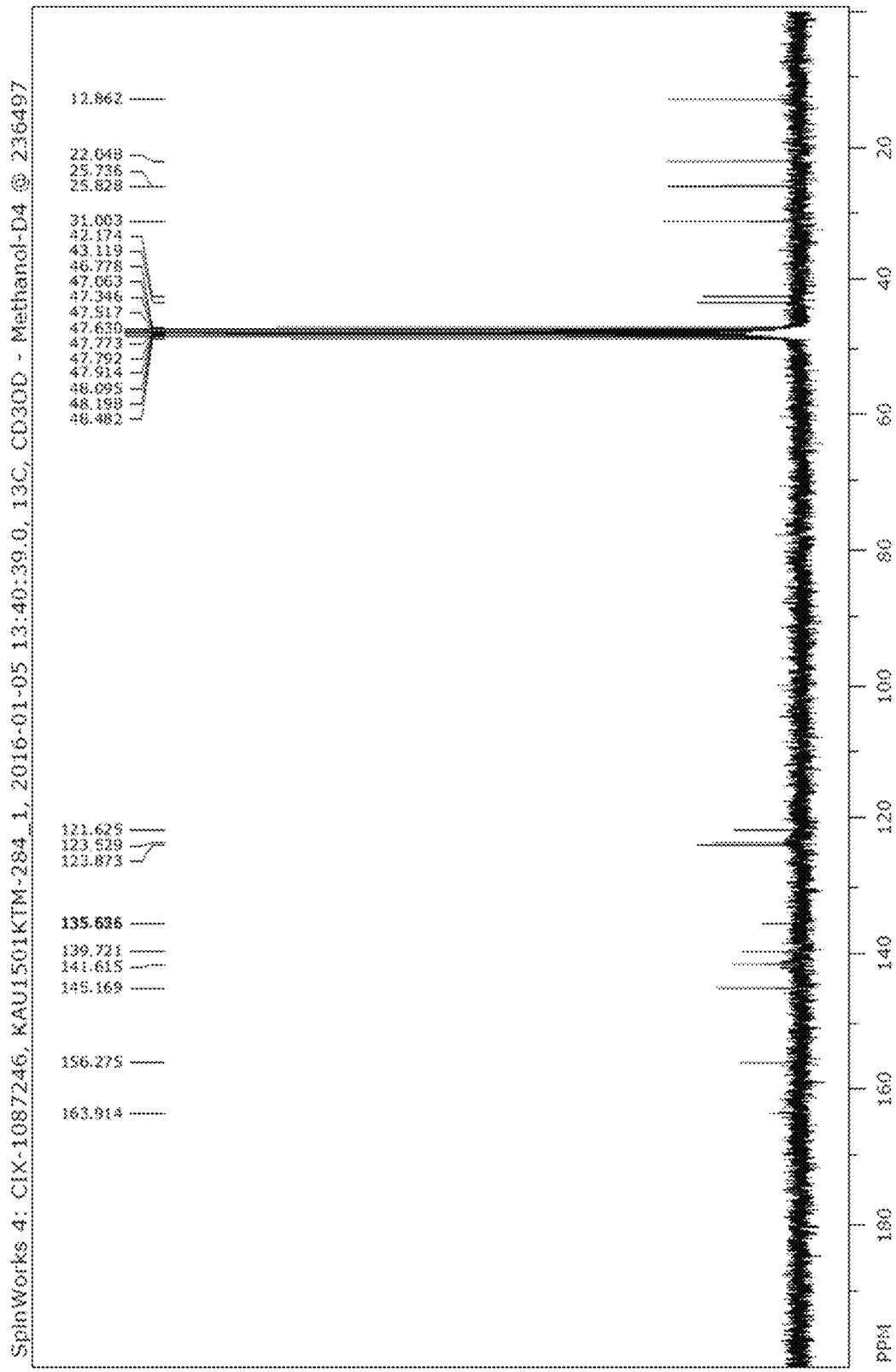
Figure 10D:
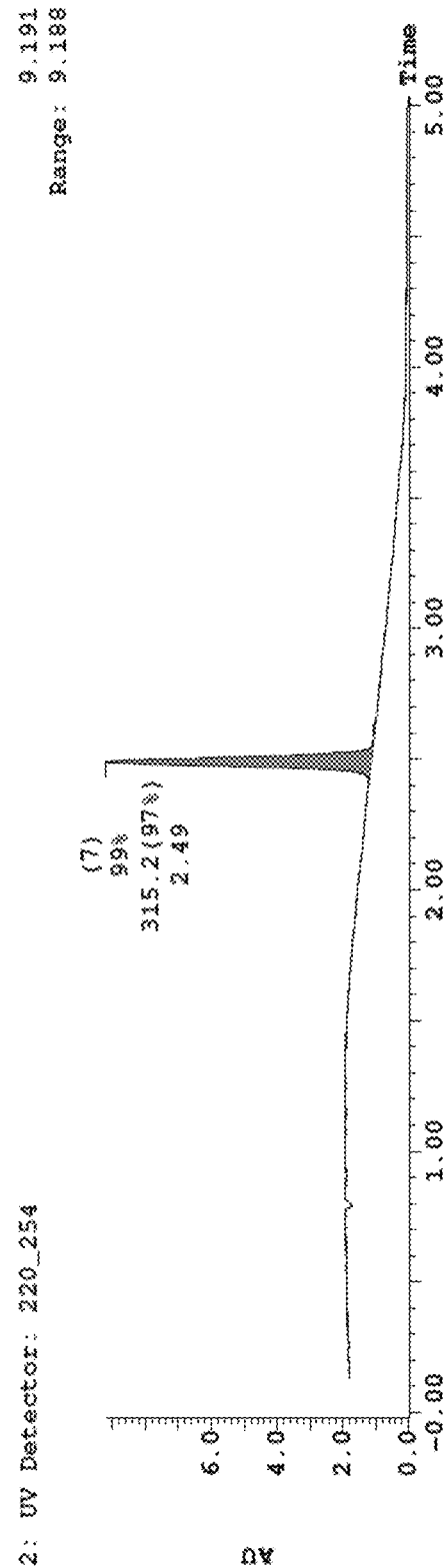
Figure 10E:
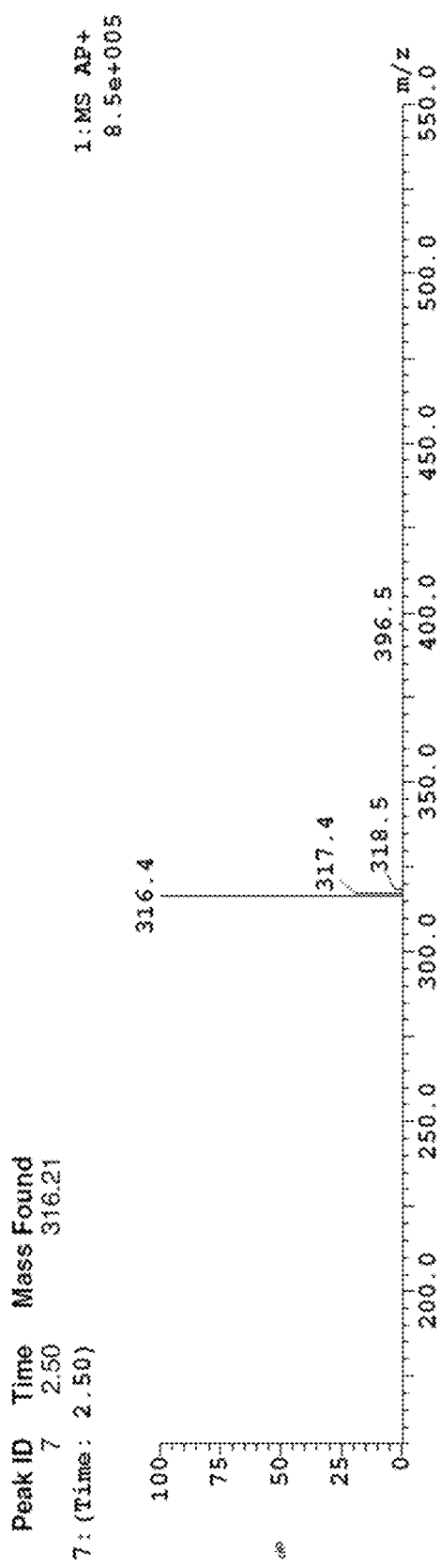
Figure 11A:
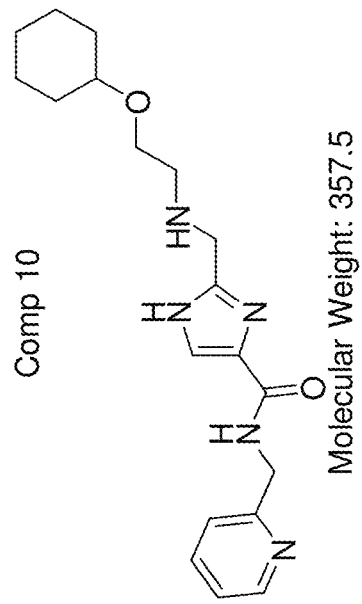
FIG. 11A. chemical structure of Comp. 10.
Figure 11B:
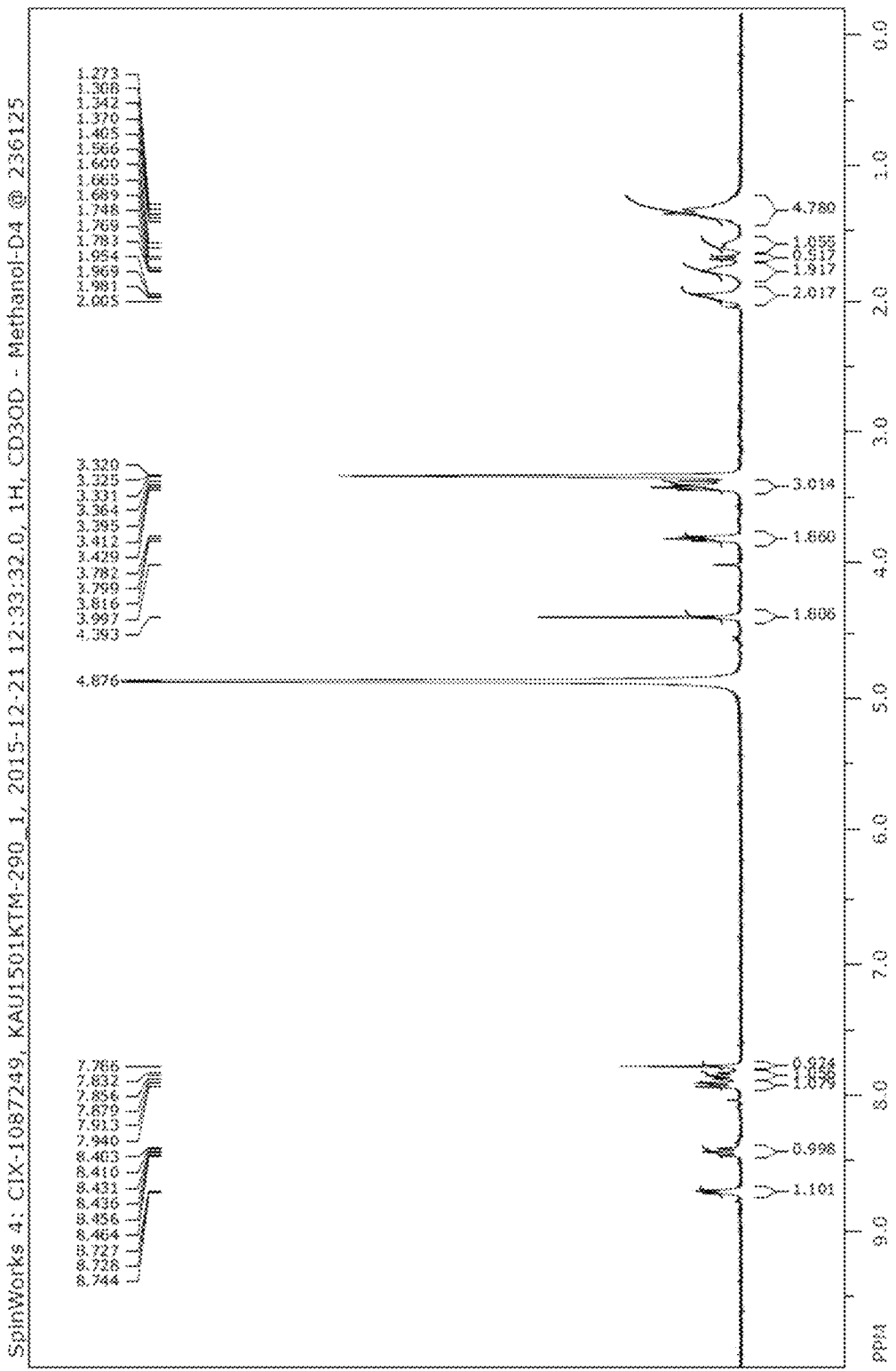
FIG. 11B, FIG. 11C, FIG. 11D, and FIG. 11E. $^1$H NMR, $^{13}$C NMR and LC-MS Spectra of Comp 10.
Figure 11C:
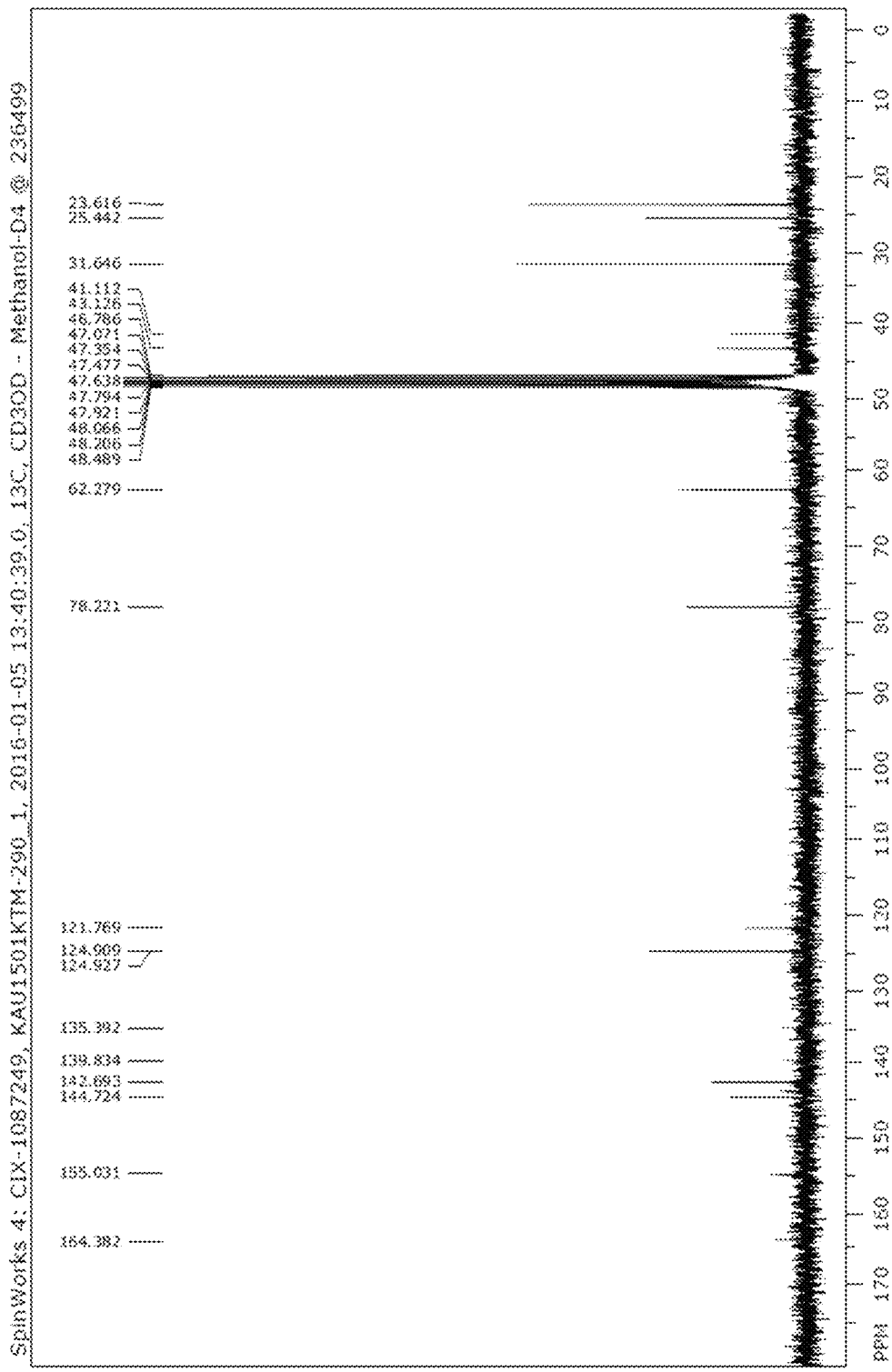
Figure 11D:
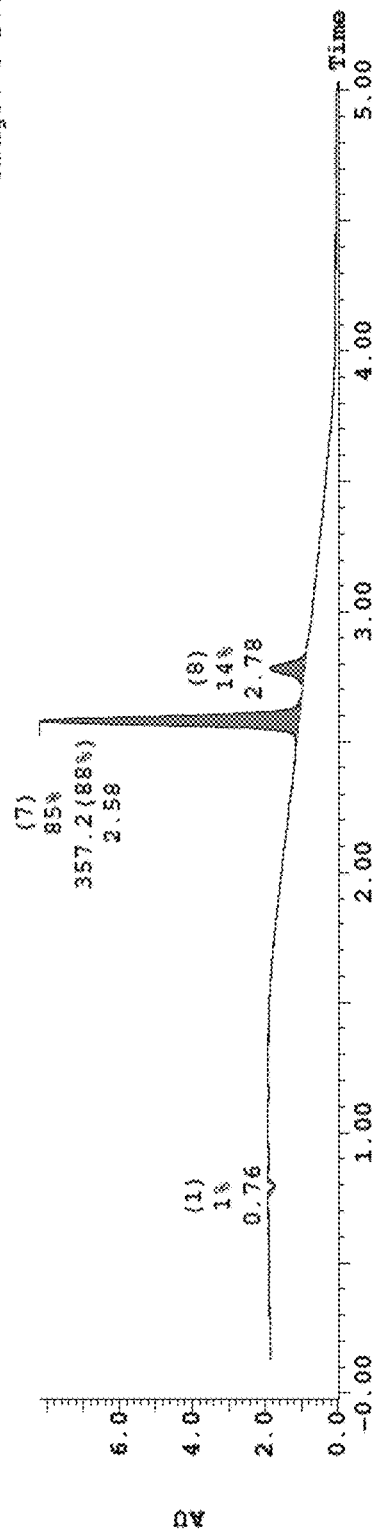
Figure 11E:
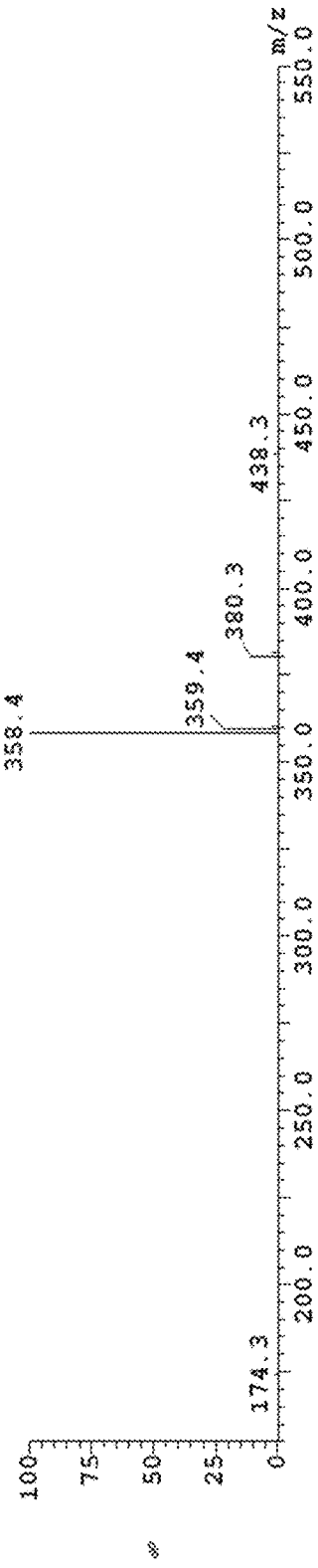
Figure 12A:
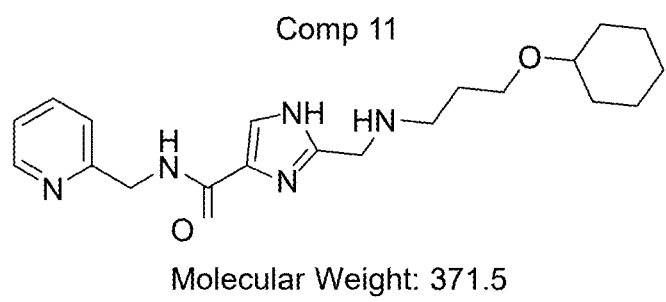
FIG. 12A. chemical structure of Comp. 11.
Figure 12B:
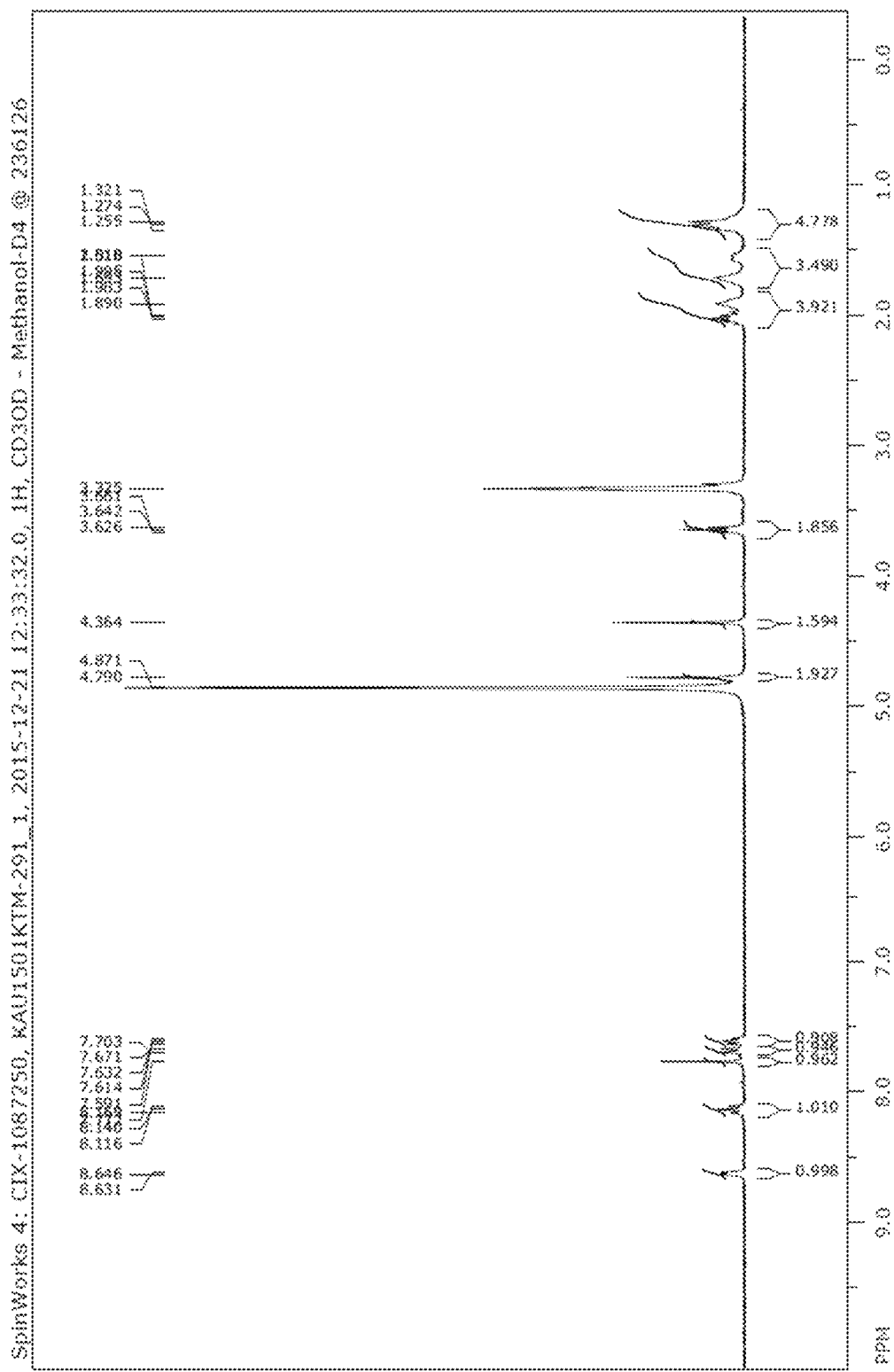
FIG. 12B, FIG. 12C, FIG. 12D, and FIG. 12E. $^1$H NMR, $^{13}$C NMR and LC-MS Spectra of Comp 11.
Figure 12C:
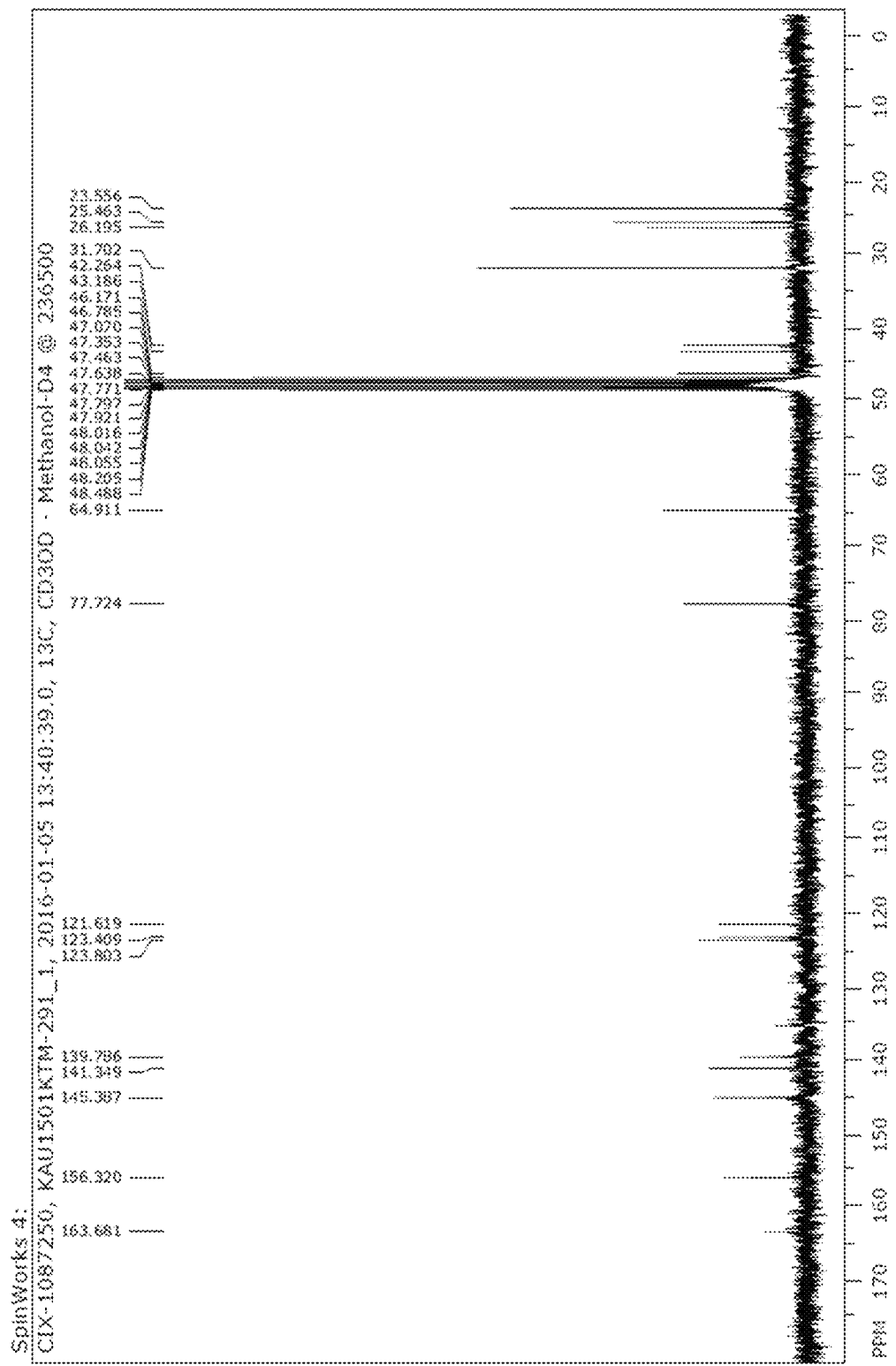
Figure 12D:
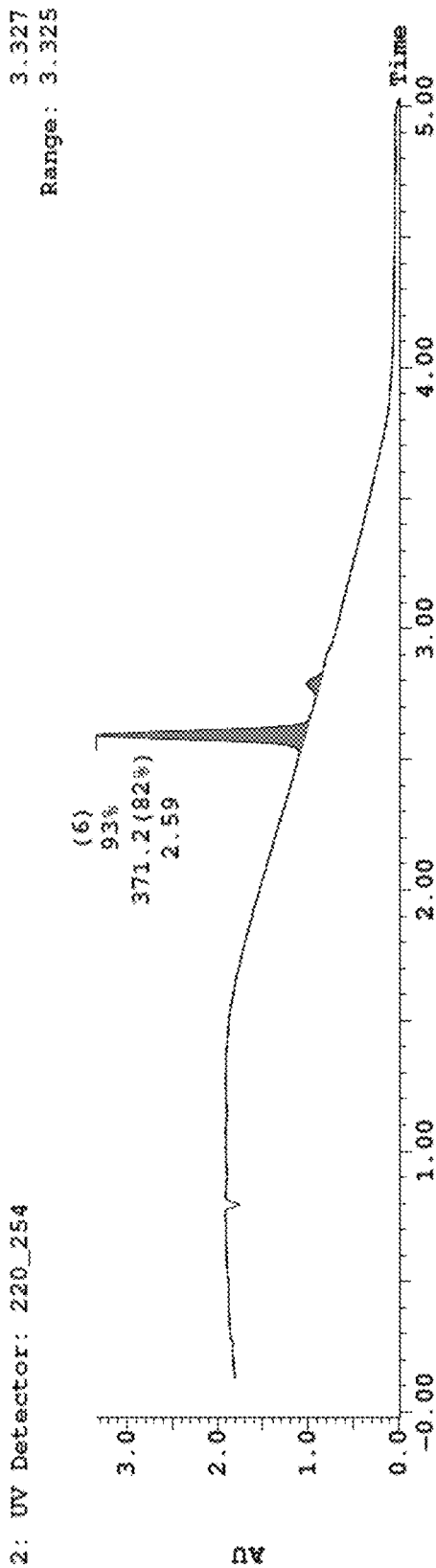
Figure 12E:
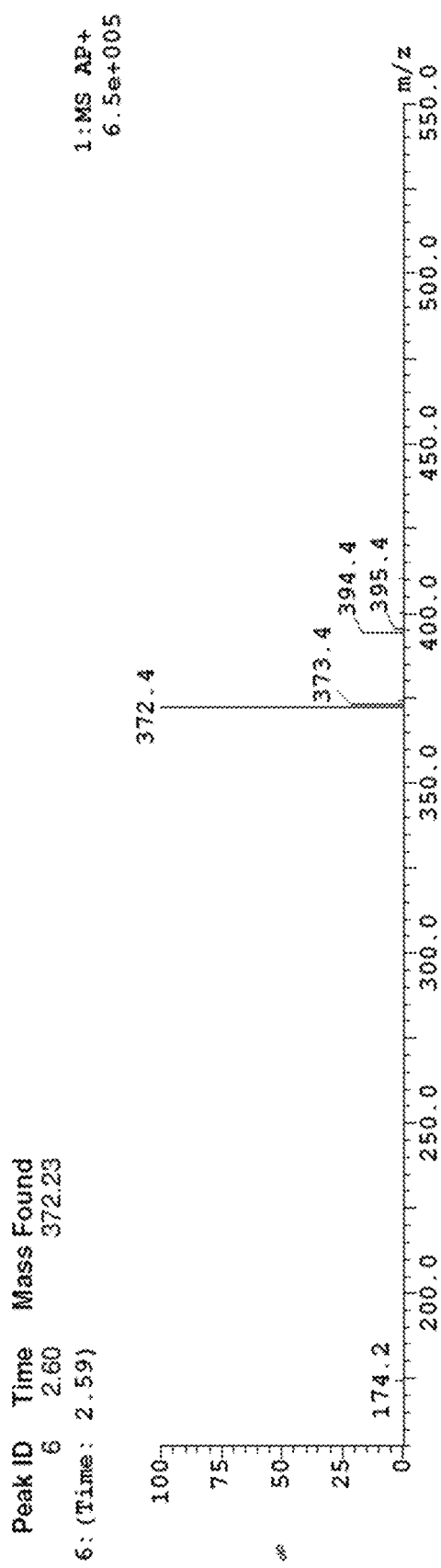
Figure 13A:
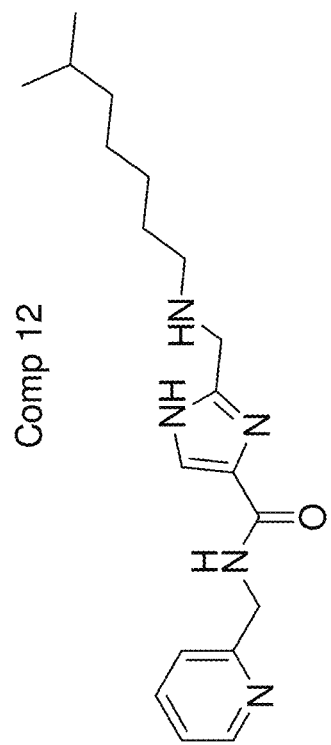
FIG. 13A. chemical structure of Comp. 12.
Figure 13B:
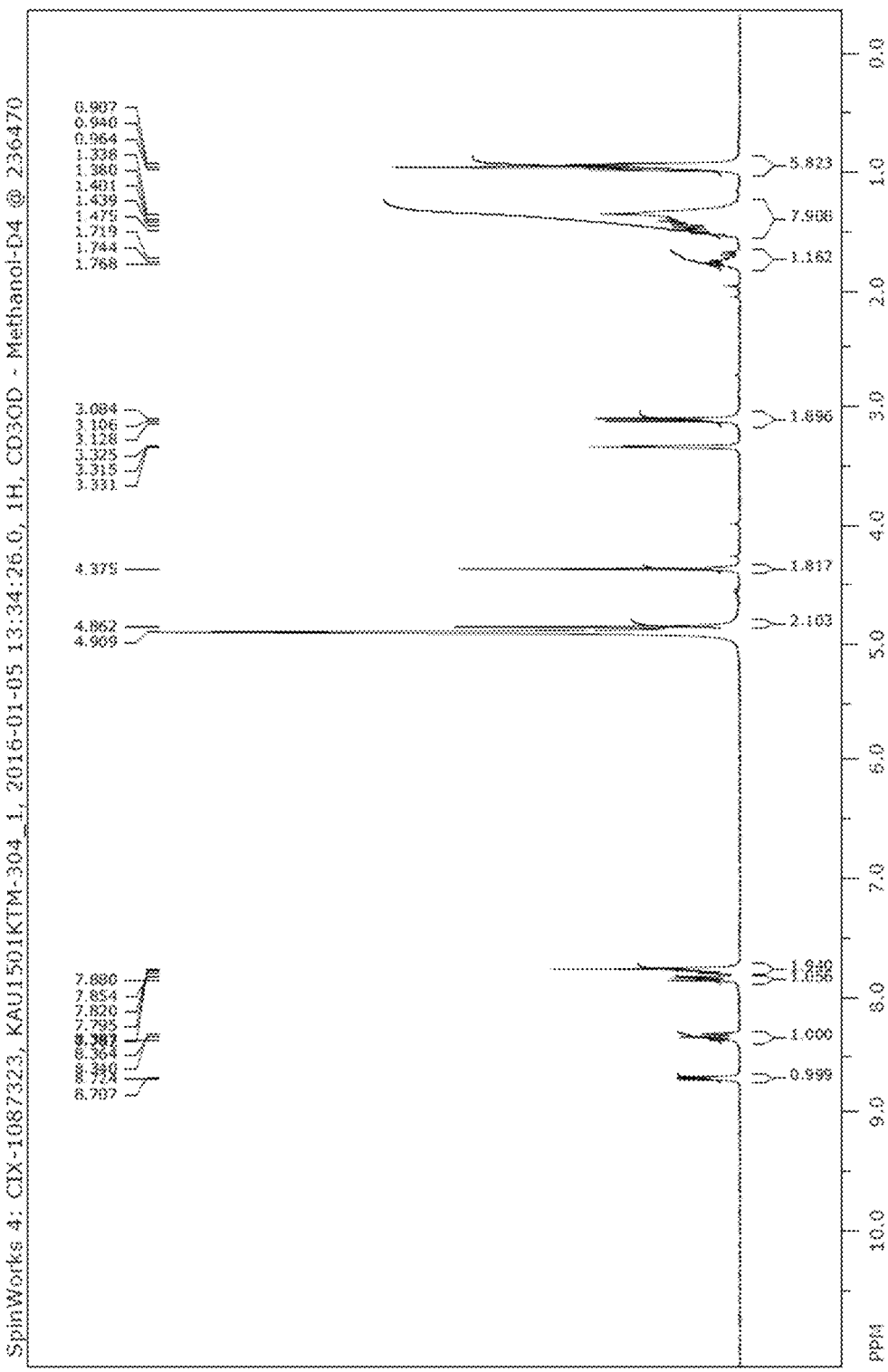
FIG. 13B, FIG. 13C, FIG. 13D, and FIG. 13E. $^1$H NMR, $^{13}$C NMR and LC-MS Spectra of Comp 12.
Figure 13C:
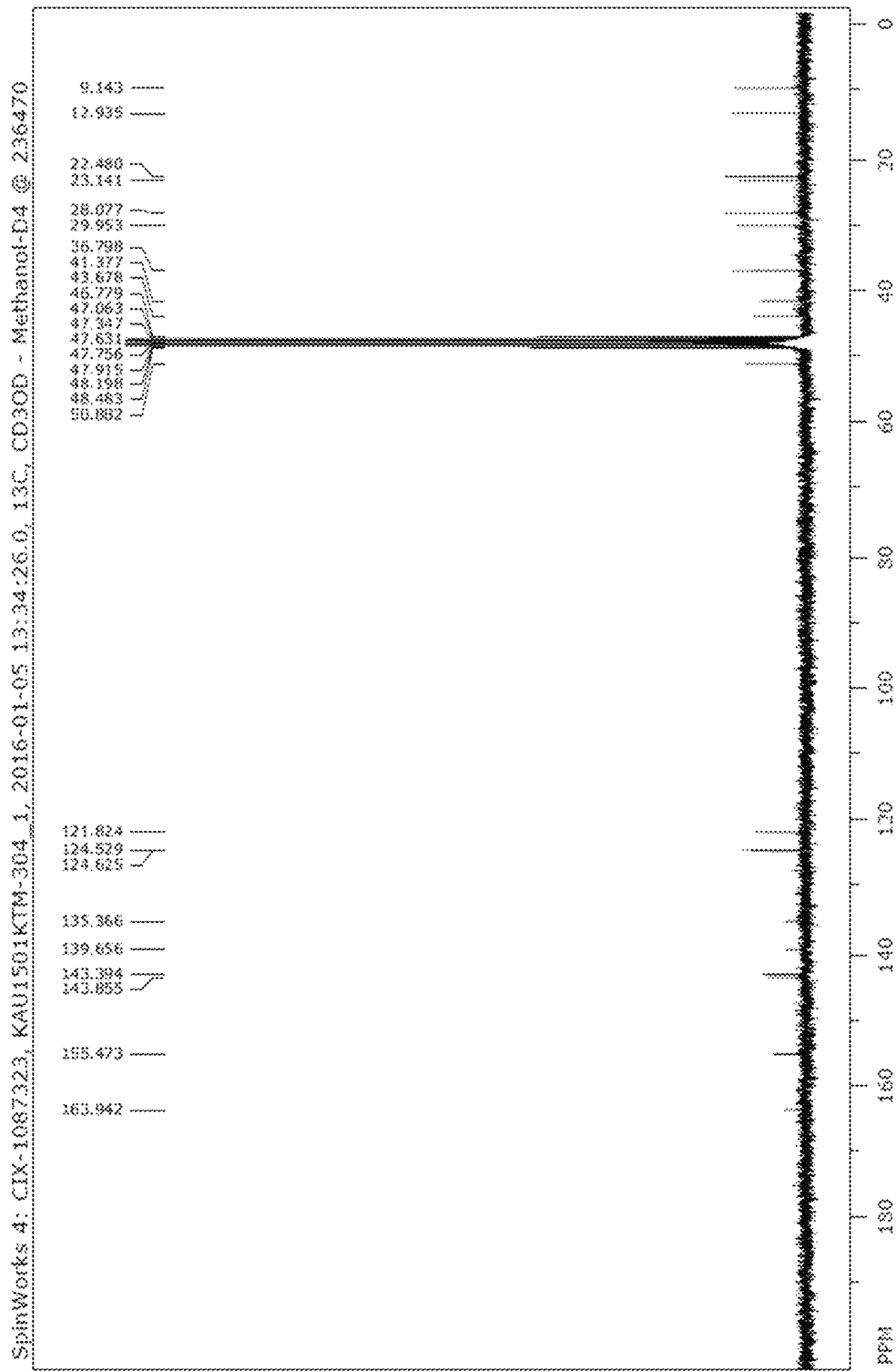
Figure 13D:
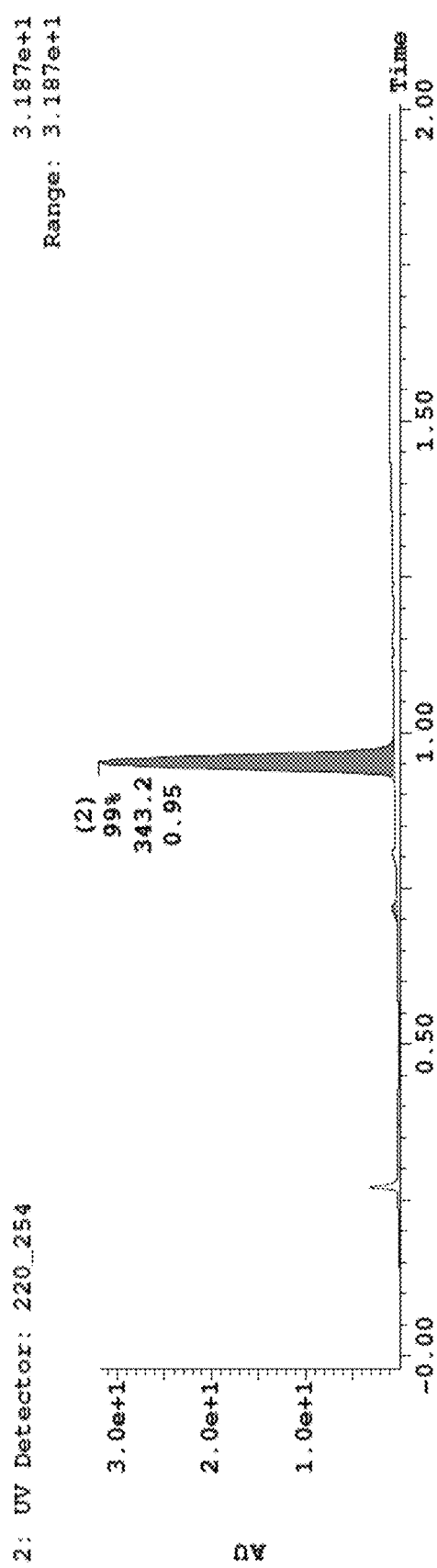
Figure 13E:
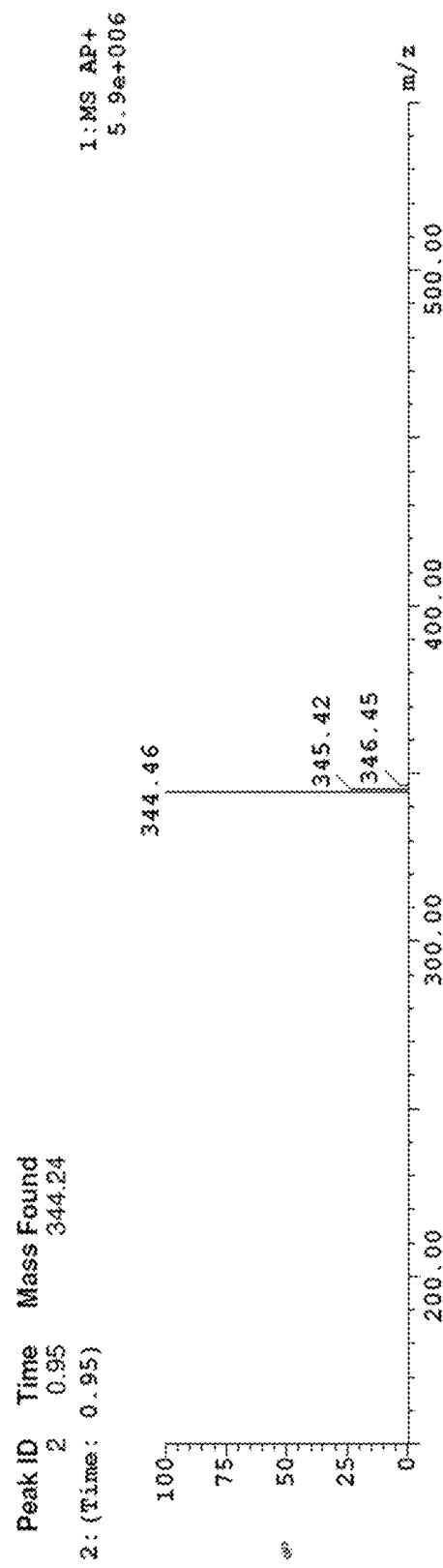
Figure 14A:
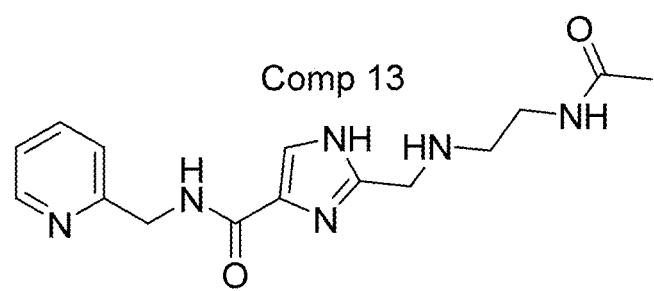
FIG. 14A chemical structure of Comp. 13.
Figure 14B:
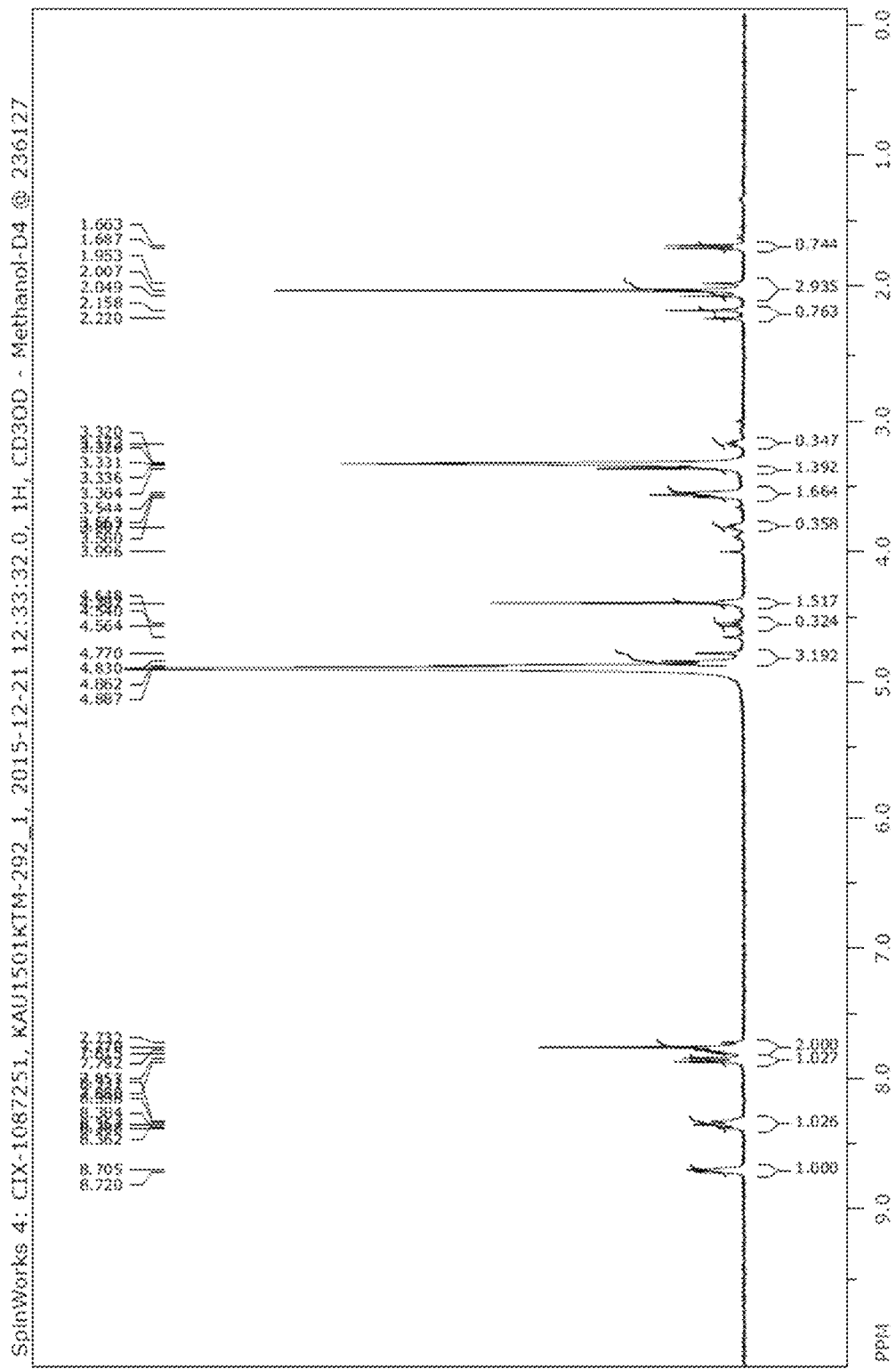
FIG. 14B, FIG. 14C, FIG. 14D and FIG. 14E. $^1$H NMR, $^{13}$C NMR and LC-MS Spectra of Comp 13.
Figure 14C:
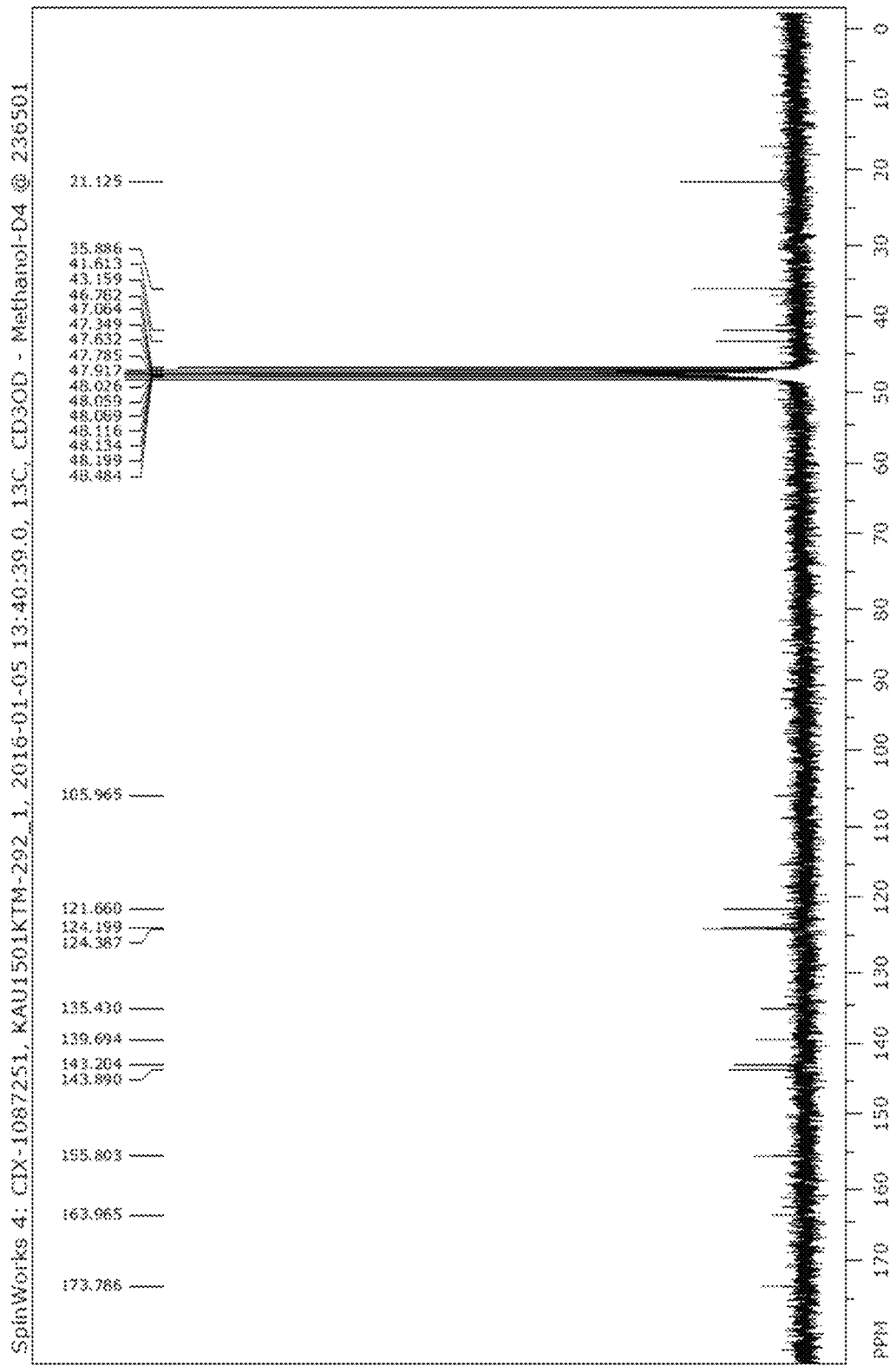
Figure 14D:
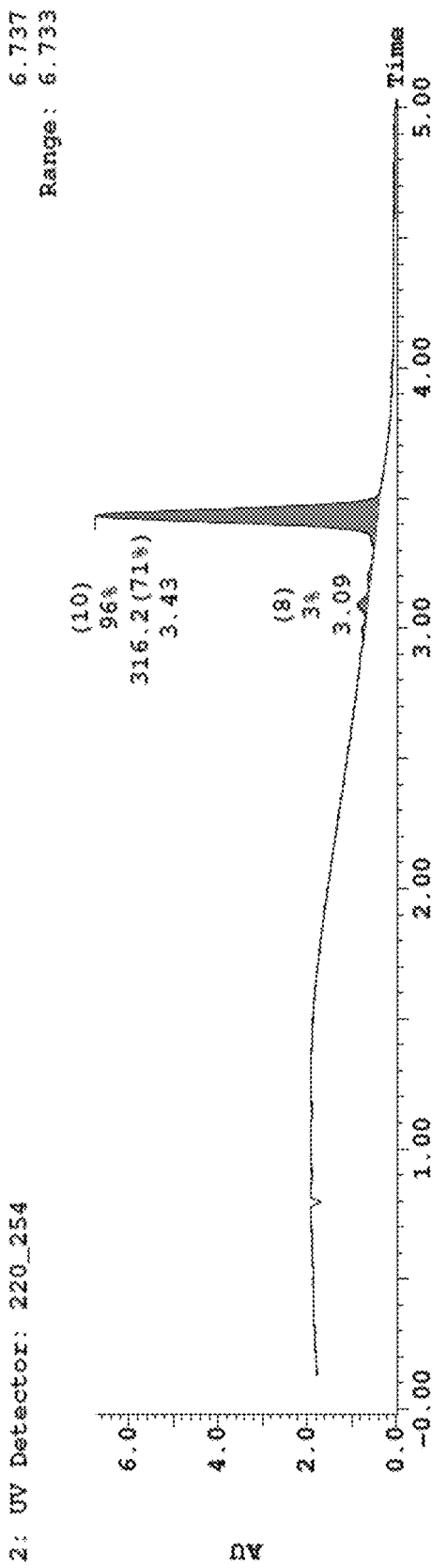
Figure 14E:
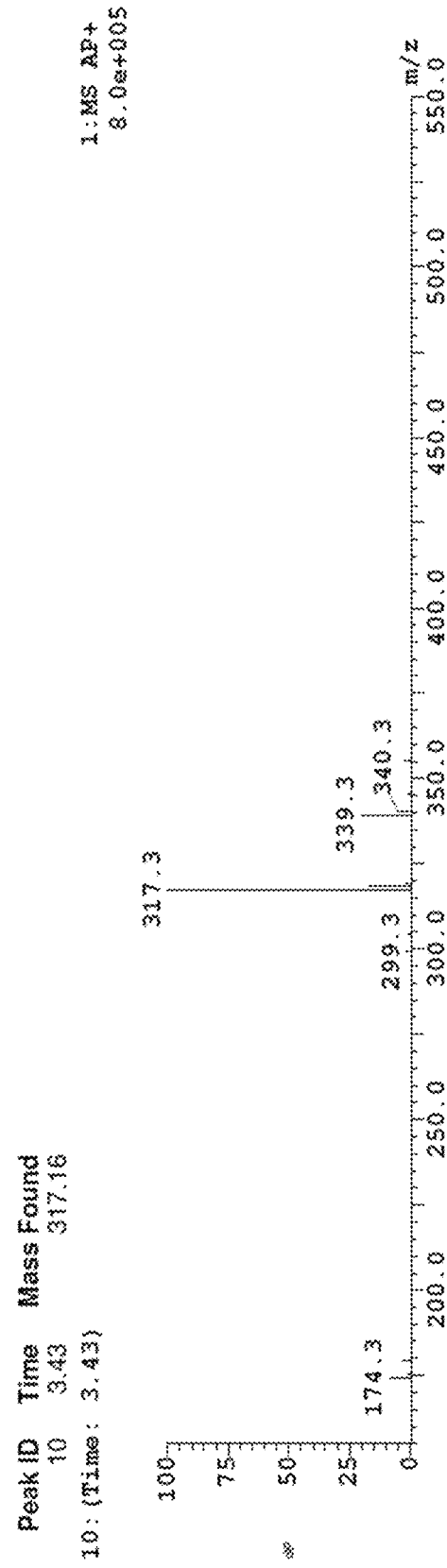
Figure 15:
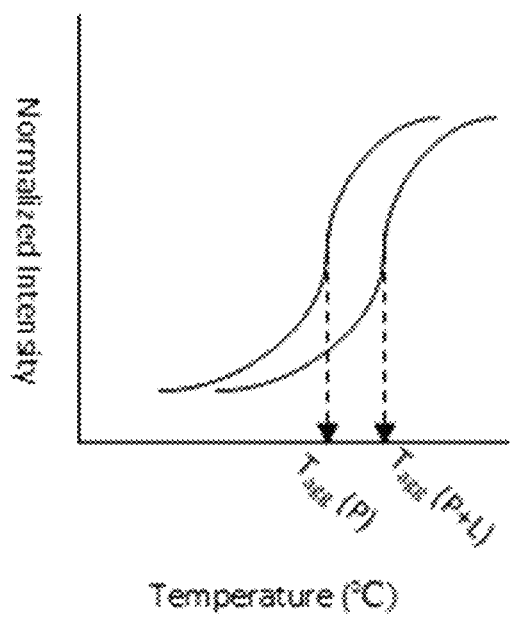
FIG. 15. Sketch representation of the DSLS plots; $T_{agg}$ (P) is the aggregation temperature of a protein, $T_{agg}$ (P+L) is the aggregation temperature of a protein-ligand mixture.
Figure 16:
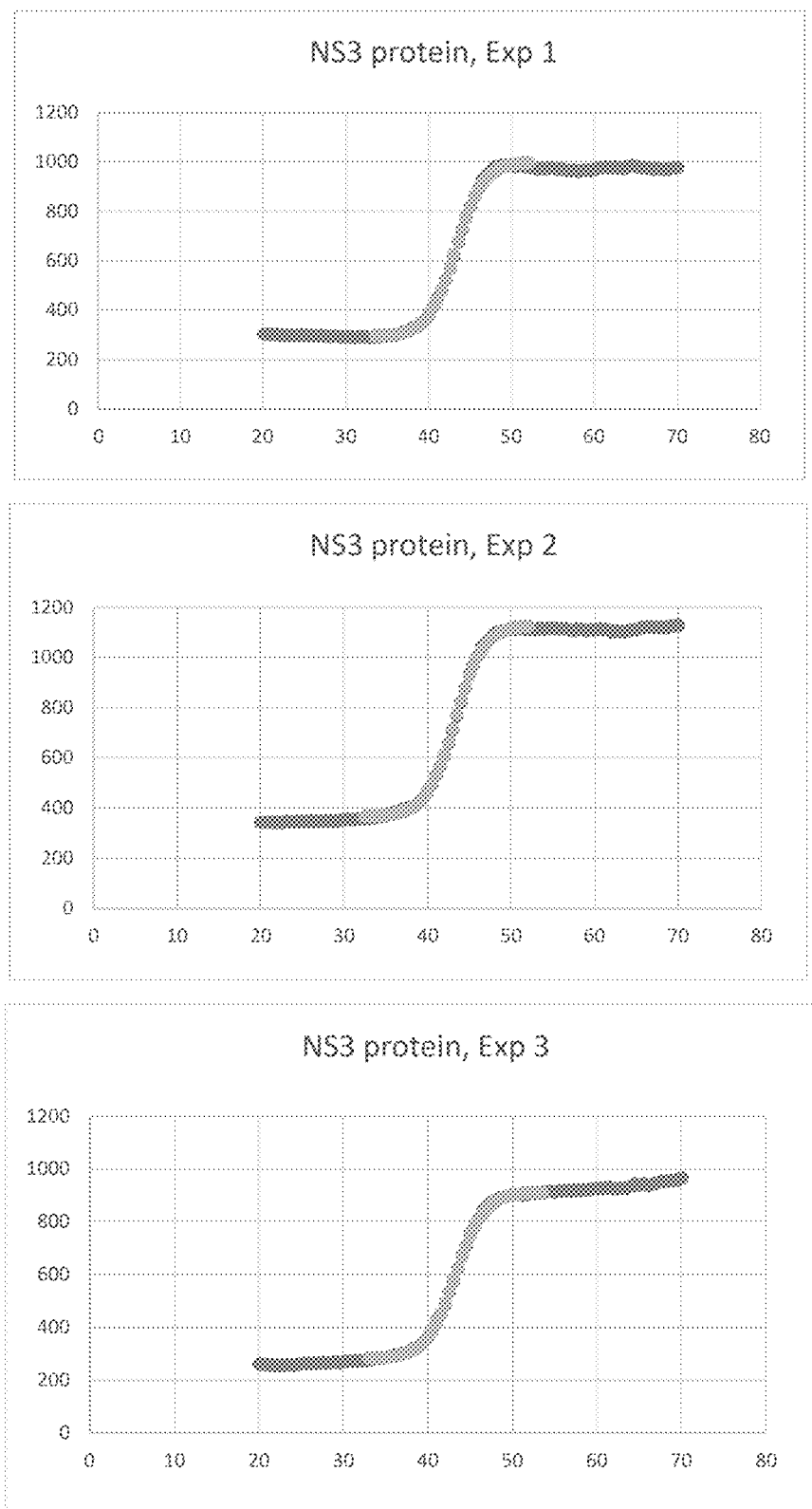
FIG. 16. Plots of three DSLS experiments of NS3: protein X axis is temperature (° C.) and Y axis is the relative light intensity compared to blank.
Figure 17:
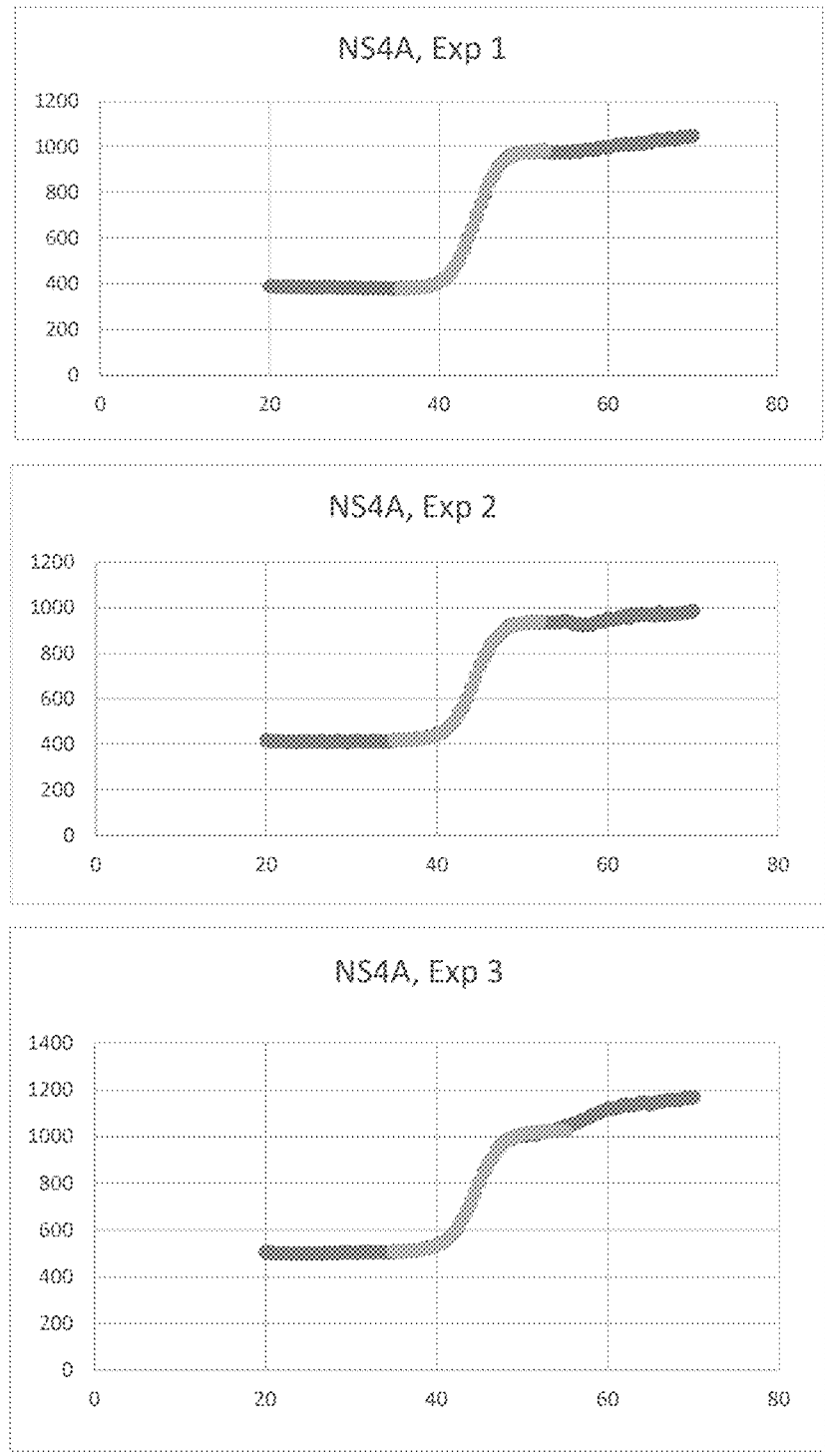
FIG. 17. Plots of three DSLS experiments of NS3+NS4A: X axis is temperature (° C.) and Y axis is the relative light intensity compared to blank.
Figure 18:
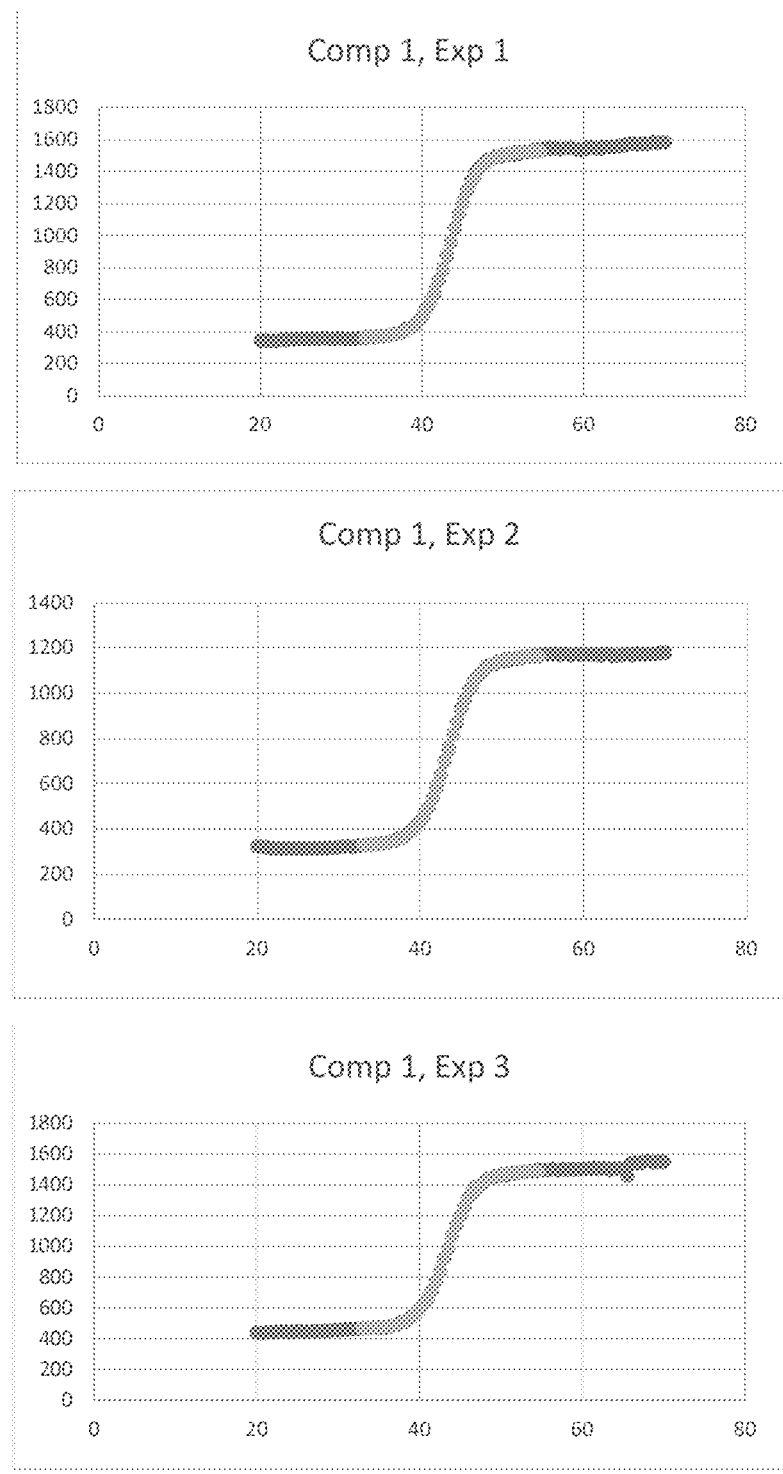
FIG. 18. Plots of three DSLS experiments of NS3+Comp 1: protein X axis is temperature (° C.) and Y axis is the relative light intensity compared to blank.
Figure 19:
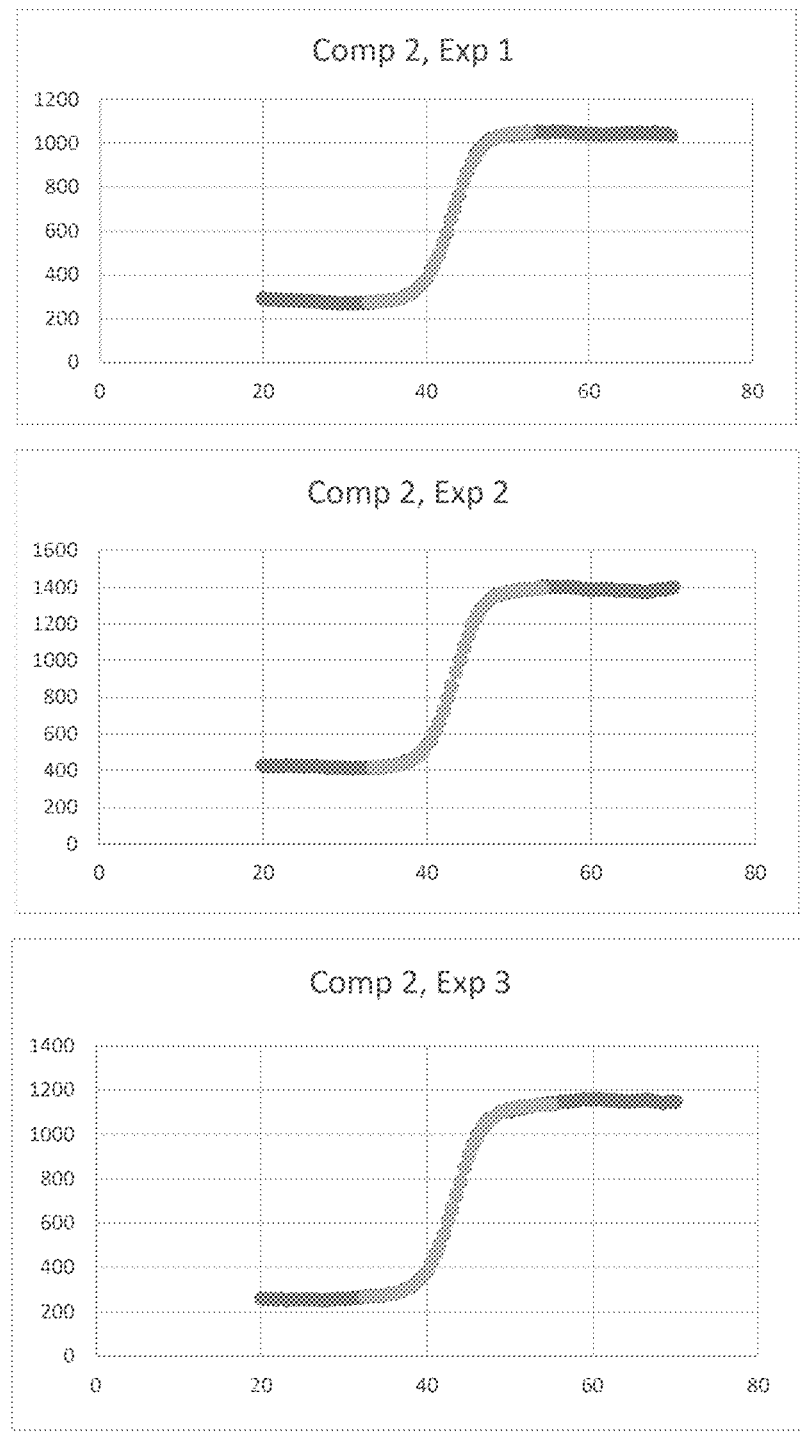
FIG. 19. Plots of three DSLS experiments of NS3+Comp 2: protein X axis is temperature (° C.) and Y axis is the relative light intensity compared to blank.
Figure 20:
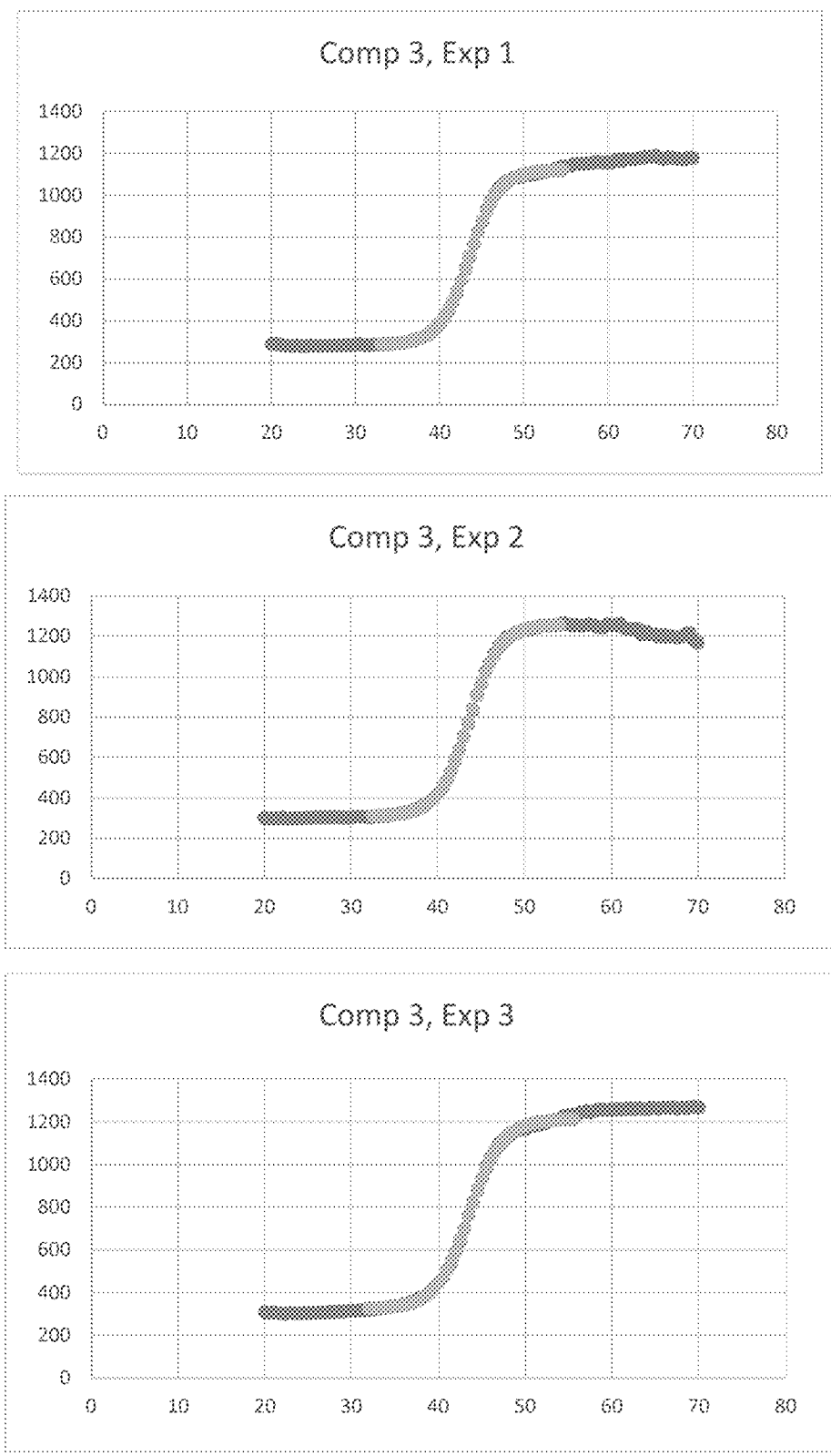
FIG. 20. Plots of three DSLS experiments of NS3+Comp 3: protein X axis is temperature (° C.) and Y axis is the relative light intensity compared to blank.
Figure 21:
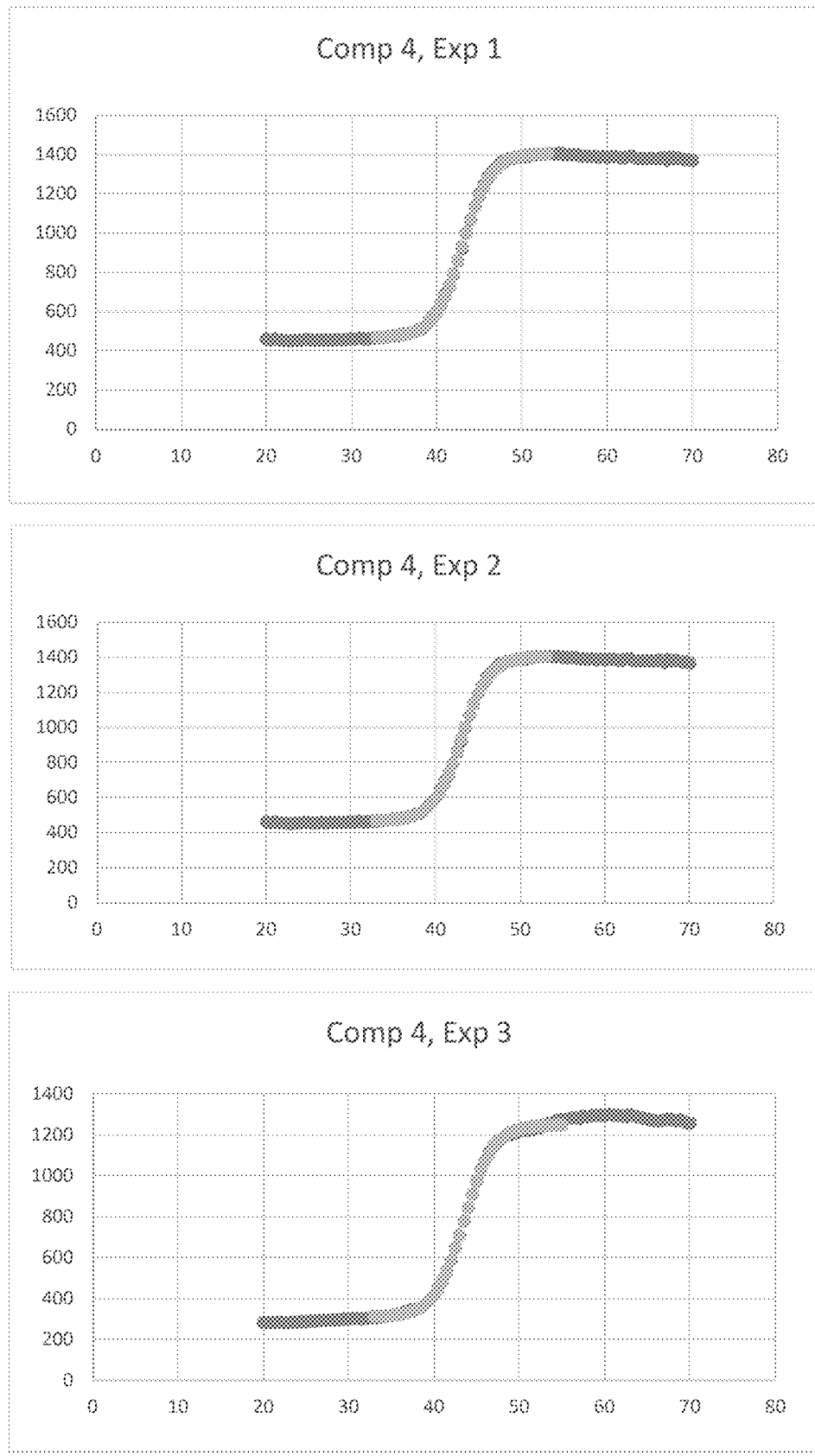
FIG. 21. Plots of three DSLS experiments of NS3+Comp 4: protein X axis is temperature (° C.) and Y axis is the relative light intensity compared to blank.
Figure 22:
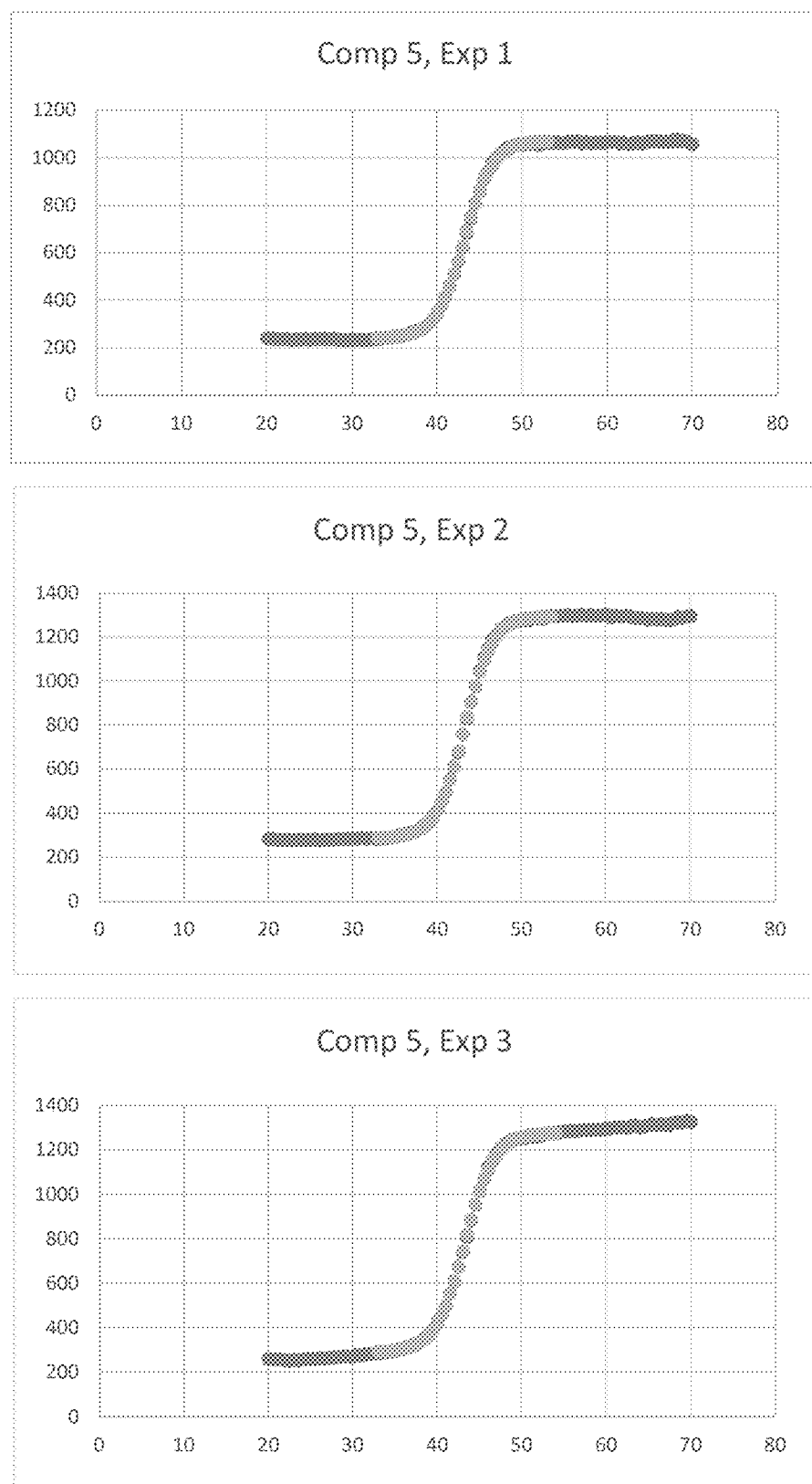
FIG. 22. Plots of three DSLS experiments of NS3+Comp 5: protein X axis is temperature (° C.) and Y axis is the relative light intensity compared to blank.
Figure 23:
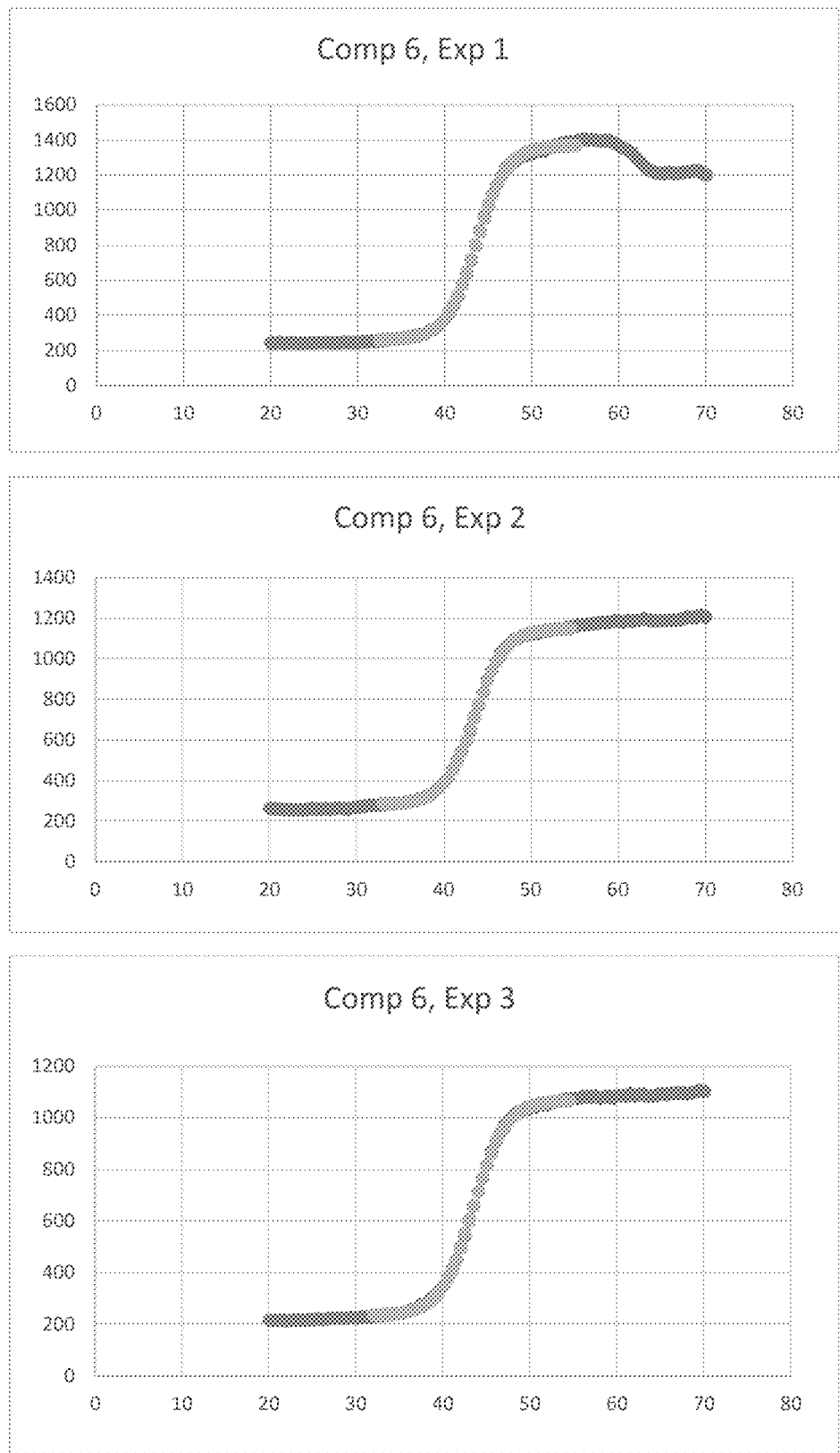
FIG. 23. Plots of three DSLS experiments of NS3+Comp 6: protein X axis is temperature (° C.) and Y axis is the relative light intensity compared to blank.
Figure 24:
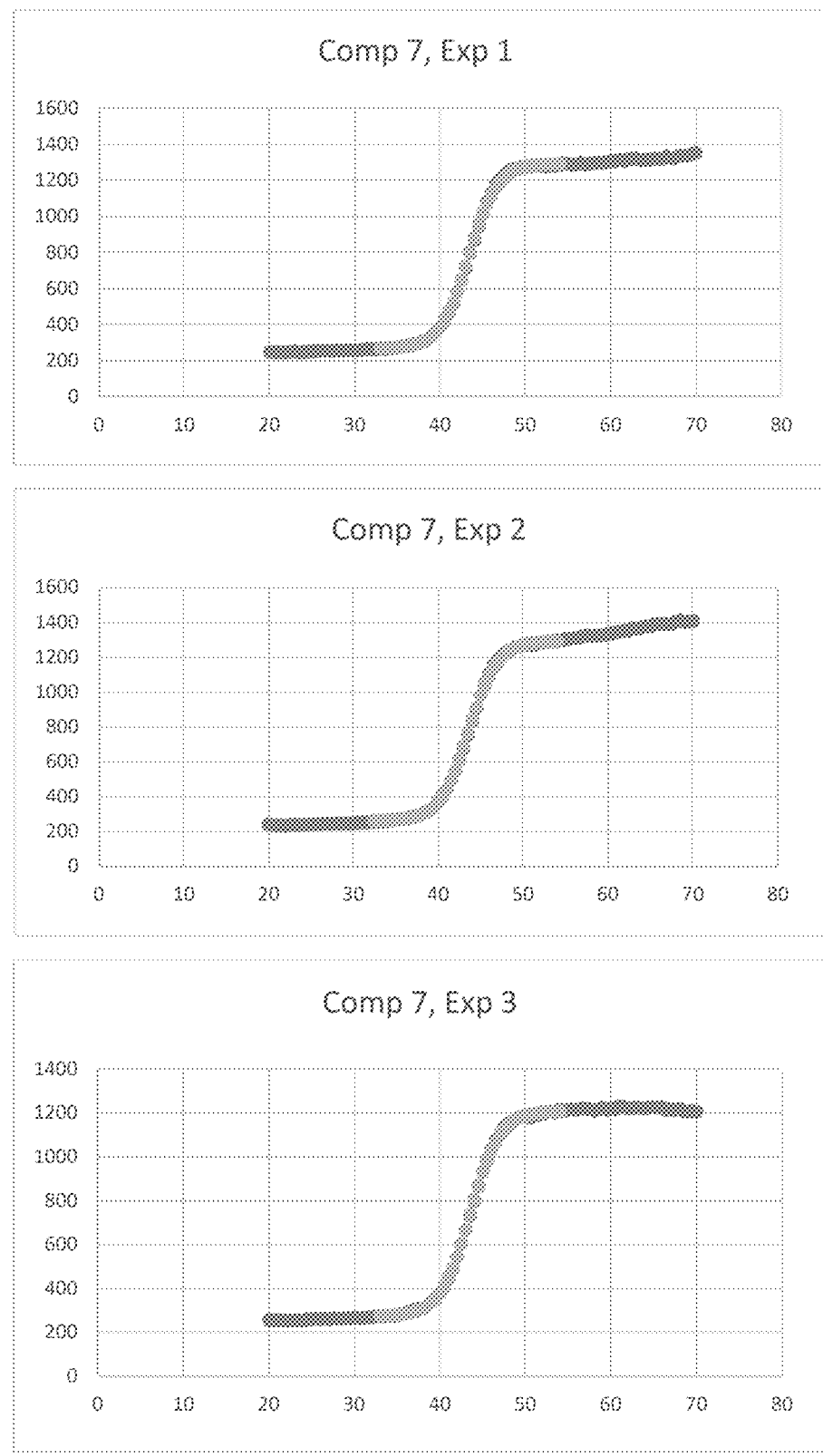
FIG. 24. Plots of three DSLS experiments of NS3+Comp 7: protein X axis is temperature (° C.) and Y axis is the relative light intensity compared to blank.
Figure 25:
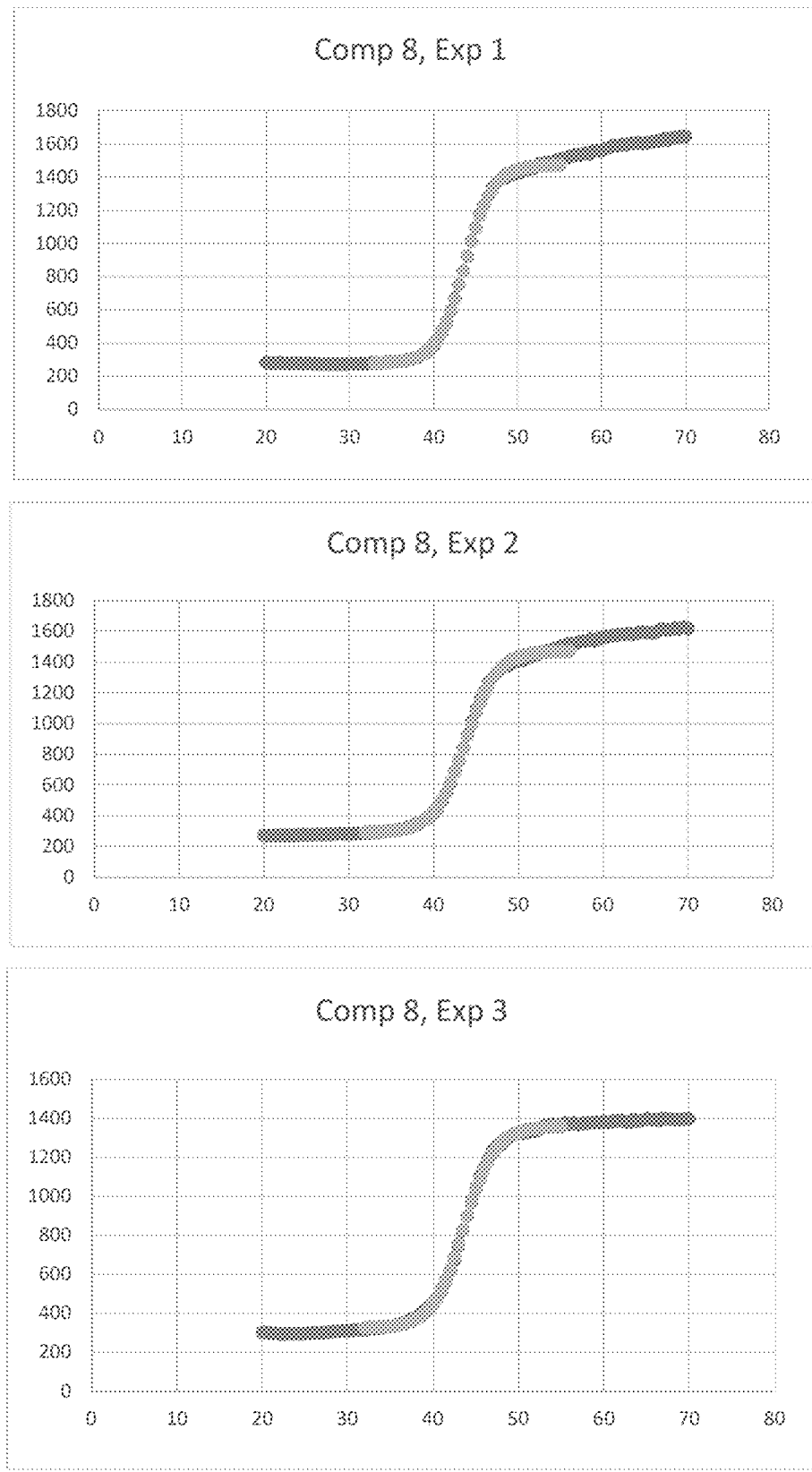
FIG. 25. Plots of three DSLS experiments of NS3+Comp 8: protein X axis is temperature (° C.) and Y axis is the relative light intensity compared to blank.
Figure 26:
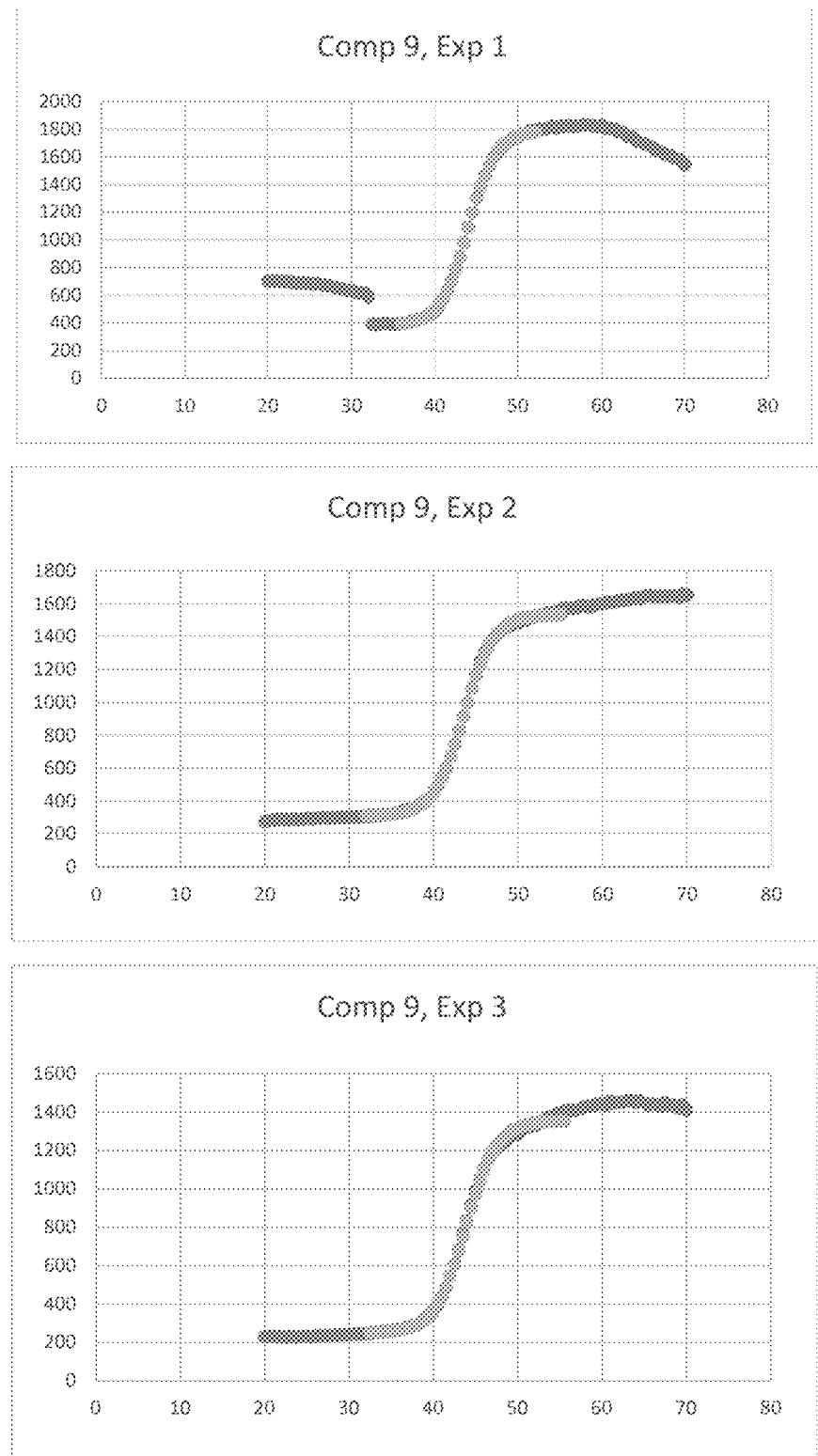
FIG. 26. Plots of three DSLS experiments of NS3+Comp 9: protein X axis is temperature (° C.) and Y axis is the relative light intensity compared to blank.
Figure 27:
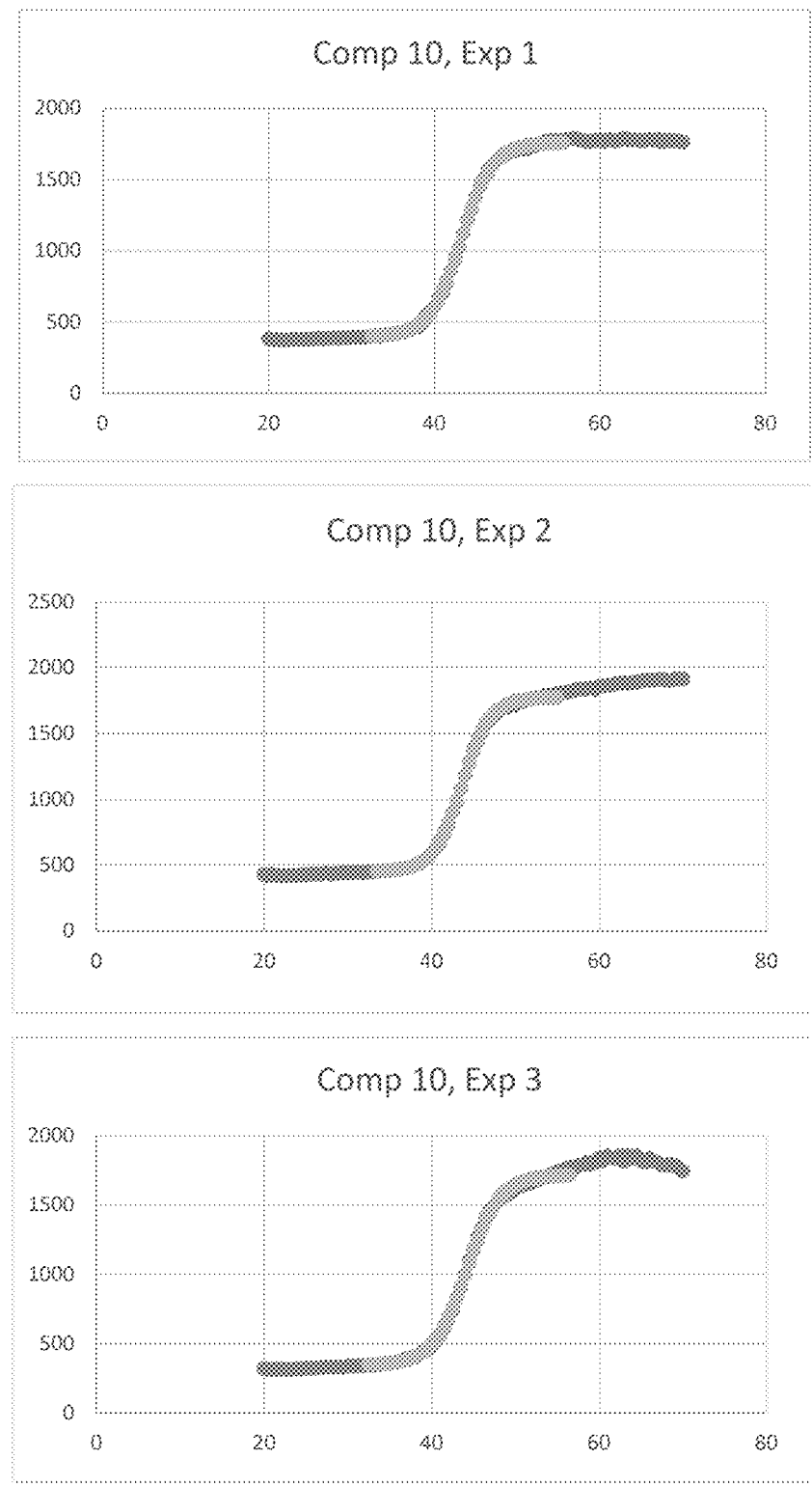
FIG. 27. Plots of three DSLS experiments of NS3+Comp 10: protein X axis is temperature (° C.) and Y axis is the relative light intensity compared to blank.
Figure 28:
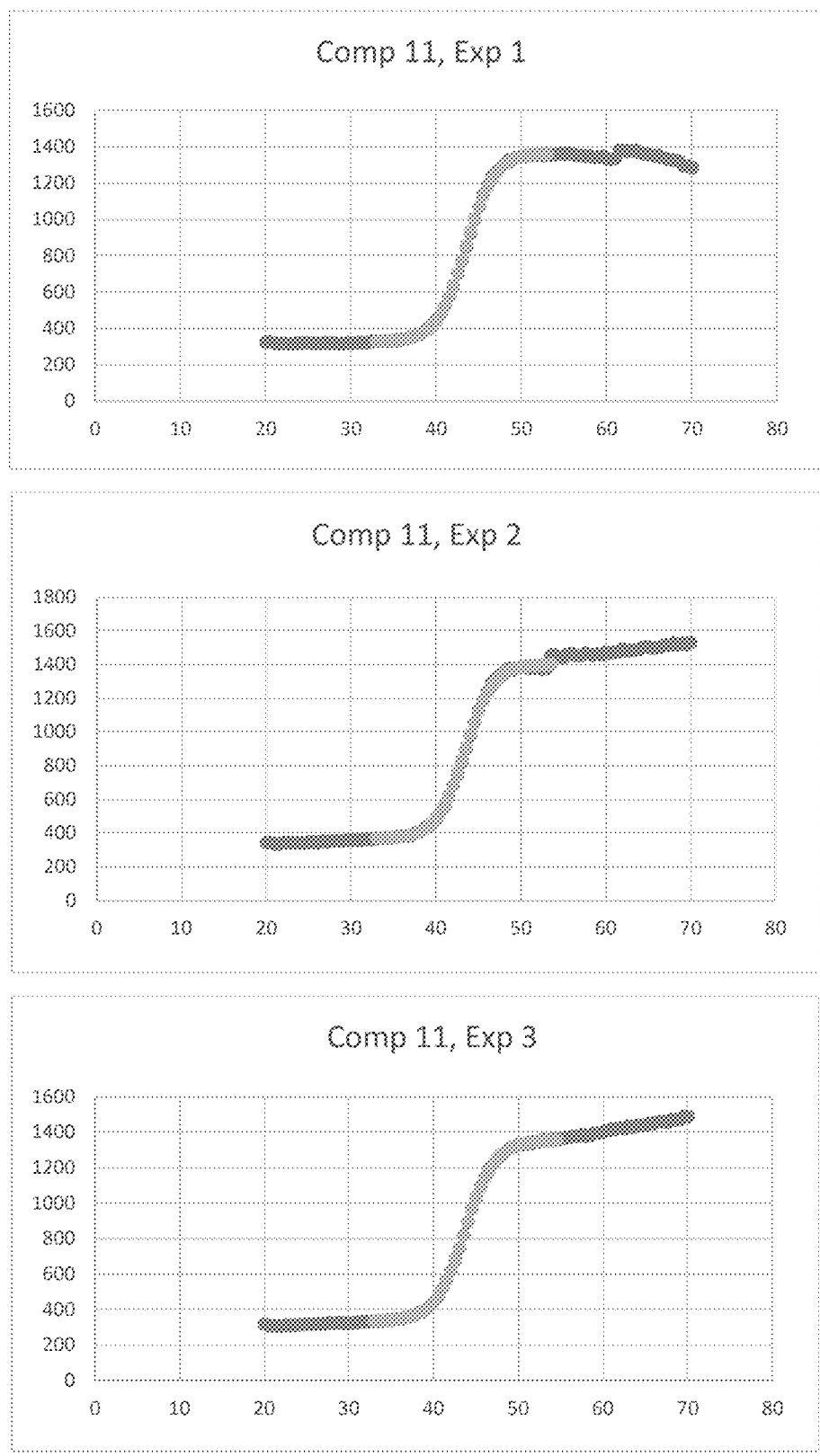
FIG. 28. Plots of three DSLS experiments of NS3+Comp 11: protein X axis is temperature (° C.) and Y axis is the relative light intensity compared to blank.
Figure 29:
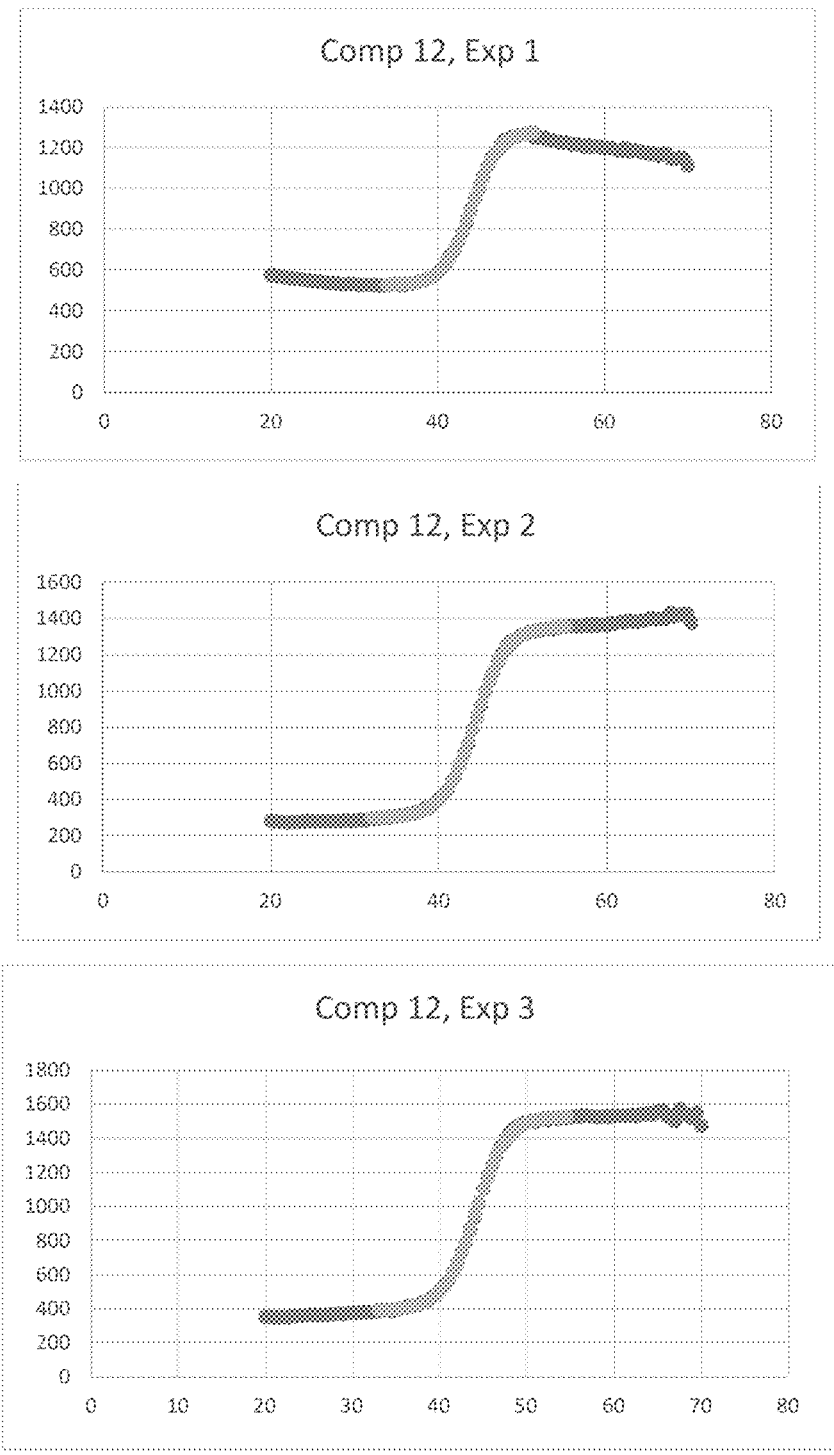
FIG. 29. Plots of three DSLS experiments of NS3+Comp 12: protein X axis is temperature (° C.) and Y axis is the relative light intensity compared to blank.

Embodiments of the present disclosure will now be described more fully hereinafter with reference to the accompanying drawings, in which some, but not all, embodiments of the disclosure are shown by example.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "complex", "compound", and "product" are used interchangeably, and are intended to refer to a chemical entity, whether in the solid, liquid or gaseous phase, and whether in a crude mixture or purified and isolated.

As used herein, the terms NS3, NS3 protein, HCV NS3, or NS3 protease or NS3/4A protease are used interchangeably, and are intended to refer to hepatitis C virus non-structural protein 3.

As used herein, the terms NS4A, NS4A peptide or $NS4A_{21\text{-}33}$ are used interchangeably, and are intended to refer to the hepatitis C virus non-structural protein 4 or a synthetic portion of it thereof, represented by the core part (GSVVI25VGRIVLSG).

As used herein, the term "salt" is intended to an association between a compound of Formula I with a pharmaceutically compatible acid. Examples of such salts include, but are not limited to, salts formed with inorganic acids (for example, hydrochloric acid (HCl), hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O— alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

As used herein, the term "solvate" refers to a molecular complex formed when a compound (such as a drug or therapeutic agent) interacts with solvent molecules which are optionally organic or inorganic solvents. In this complex, the solvent molecules are incorporated into the crystalline structure of the compound. The process of solvation may occur during crystallization, where solvent molecules are retained in the lattice or bound to the compound through weak interactions like hydrogen bonding or van der Waals forces. Solvates, formed in either a stoichiometric or non-stoichiometric amount of the solvent molecules, encompass both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

For the purposes of this disclosure, the term "tautomer" refers to constitutional isomers of organic compounds that readily interconvert through a process known as tautomerization or tautomerism. This interconversion typically involves the formal migration of a hydrogen atom or proton, along with a shift in the positions of a single bond and an adjacent double bond. Tautomerism represents a specific form of structural isomerism, and due to the rapid equilibrium between the isomers, tautomers are generally regarded as the same chemical entity. In the context of this disclosure an example of "tautomer" is the imidazole core in formula I, which might exist in two distinct tautomers:

purposes of this disclosure, stereoisomers may refer to enantiomers, diastereomers, or both.

Conformers or rotamers represent a form of isomerism where molecules have the same structural formula but differ due to rotation around single bonds, resulting in different shapes or conformations. These conformations can vary in energy, typically interconvert, and are rarely isolatable, though some molecules can be isolated in distinct conformations. Atropisomers are a specific type of stereoisomer arising from hindered rotation around single bonds due to steric hindrance, allowing the conformers to be isolated. In this disclosure, stereoisomers may also refer to conformers, atropisomers, or both.

Stereoisomers of double bonds, ring systems, stereogenic centers, and similar structures can exist in the compounds disclosed here, and all stable stereoisomers are included. This includes cis- and trans-(or E- and Z-)isomers, where rotation around a double bond is restricted, resulting in fixed relative positions of substituents. These isomers may be isolated as a mixture or in separated forms. Likewise, S- and R- (or L- and D-)stereoisomers are described and may be isolated as mixtures or as separated isomeric forms. All processes and methods used to prepare the compounds described in this disclosure, including their intermediates, are also included. When stereoisomeric products are formed, they may be separated using conventional methods such as chromatography, fractional crystallization, or the use of chiral agents.

The compounds of the present disclosure may be prepared by methods known to those of ordinary skills in the art. The following methods set forth below are provided for illustrative purposes and are not intended to limit the scope of the disclosure. It will be recognized that it may be preferred or necessary to prepare such a compound in which a functional

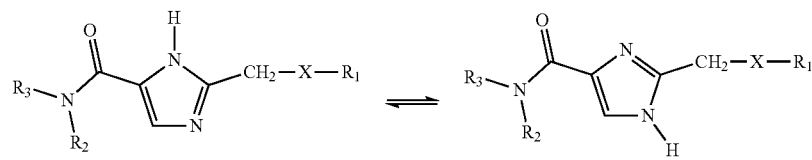

Other examples of common tautomeric pairs include, but are not limited to, ketone and enol, enamine and imine, ketene and ynol, nitroso and oxime, amide and imidic acid, lactam and lactim (an amide and imidic tautomerism in heterocyclic rings).

In this disclosure, the term "stereoisomer" refers to molecules that have the same molecular formula and bonding sequence (i.e., constitution) but differ in the three-dimensional arrangement of their atoms in space. This contrasts with structural isomers, which share the same molecular formula but differ in the connectivity of their atoms. By definition, stereoisomers represent the same structural isomer. Enantiomers are a type of stereoisomer related as non-superimposable mirror images, where each stereogenic center in one enantiomer has the opposite configuration in the other. Enantiomers share identical physical properties except for the direction they rotate polarized light and their interactions with other optically active compounds.

Diastereomers, on the other hand, are stereoisomers that are not related by mirror symmetry and are not enantiomers. These include meso compounds, cis- and trans-(E- and Z-)isomers, and other non-enantiomeric optical isomers, which often exhibit distinct physical properties. For the group is protected using a conventional protecting group then to remove the protecting group to provide a compound of the present disclosure.

In one embodiment, the compound of formulae (I) and (II) bind to an allosteric site of the HCV NS3 protein. Preferably, the allosteric site is the NS4A peptide binding site.

In certain embodiments, the compound of formula (II) is present in addition to, or in lieu of the compound of formula (I) in the pharmaceutical composition.

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the compound represented by formula (I), the compound represented by formula (II), a salt thereof, a solvate thereof, a tautomer thereof, a stereoisomer thereof, or any mixtures thereof. In some embodiments, other active ingredients in addition to the compound of the current disclosure may be incorporated into a pharmaceutical composition.

In one or more embodiments, the pharmaceutical composition disclosed herein further includes an antiviral agent that is structurally distinct from the compounds of formulae (I) and (II). In one embodiment, the antiviral agent used herein does not have anti-HCV activity. Preferably, the antiviral agent has anti-HCV activity. As used herein, the term "anti-HCV activity" means the agent is effective to inhibit the function of at least one target selected from the group consisting of HCV metalloprotease, HCV serine protease (substrate site inhibitors), HCV polymerase, HCV helicase, HCV NS4B protein, HCV entry, HCV assembly, HCV egress, HCV NS5A protein, IMPDH and a nucleoside analog for the treatment of an HCV infection.

Exemplary antiviral agents with anti-HCV activity include, but are not limited to, Imiqimod, ribavirin, amantadine, rimantadine, interferon such as interferon alpha 2B, pegylated interferon alpha, consensus interferon, interferon alpha 2A, and lymphoblastiod interferon tau, interleukins such as interleukin 2, interleukin 6, and interleukin 12, other inhibitors of HCV NS3 protease, inhibitors of other targets in the HCV life cycle such as direct antiviral agents (DAA's) such as protease, helicase, polymerase or internal ribosome entry site; or combinations thereof, and the like. Alternatively, the antiviral agent may act as an additional therapy, and the compounds of formula (I) and/or (II) may be administered with the antiviral agent in combination therapy, either jointly or separately.

In one or more embodiments, the pharmaceutical composition comprises up to 10% by weight of the pharmaceutically acceptable carrier and/or excipient relative to a total weight of the pharmaceutical composition. In one or more embodiments, the pharmaceutical composition comprises a range from 0.01 wt % up to 99.9 wt % of the compound of formula (I) relative to a total weight of the pharmaceutical composition.

In some embodiments, the composition comprises up to 10 wt % of a pharmaceutically acceptable salt of the compound of formula (I). In some embodiments, the composition comprises up to 10 wt % of a pharmaceutically acceptable solvate of the compound of formula (I). Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, PA, 1975; and Liberman, H. A.; Lachman, L., Eds. Pharmaceutical dosage forms, Marcel Decker, New York, NY, 1980, which are incorporated herein by reference in their entirety.

In other embodiments, the pharmaceutical composition having the compound of formula (I), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration.

In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to another aspect, the present disclosure relates to a method of preventing or treating hepatitis C virus (HCV) infection. The method involves administering the pharmaceutical composition of the third aspect to a subject in need of therapy.

As used herein, the term "preventing" in the context of the administration of a therapy to a subject in need thereof refers to preventing a disease, disorder or condition from occurring in a subject which may be predisposed to the disease, disorder and/or condition but has not yet been diagnosed as having it. The term "treating" refers to (i) inhibiting the disease, disorder or condition, i.e., arresting its development; (ii) relieving the disease, disorder or condition, i.e., causing regression of the disease, disorder and/or condition, and (iii) alleviating and/or ameliorating symptoms of the disease, disorder, or condition. Treatment is preferably commenced at the time of infection or post infection with HCV. It is recommended that the treatment continues until the virus is no longer present or active. For protecting a non-infected subject from future infection, the treatment continues for as long as there is a potential exposure to the virus.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In a preferred embodiment, the active ingredient and/or the pharmaceutical composition described herein are administered orally.

In one or more embodiments, the pharmaceutical composition administered comprises the compound of formula (I), or a salt thereof, a solvate thereof, a tautomer thereof, a stereoisomer thereof, or a mixture thereof. In a preferred embodiment, the pharmaceutical composition administered comprises a compound which is

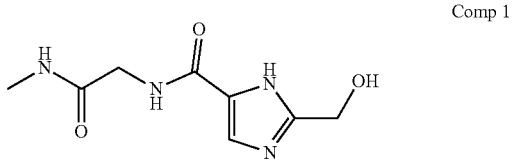

Comp 1

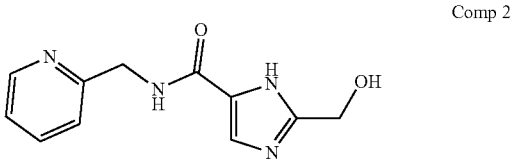

Comp 2

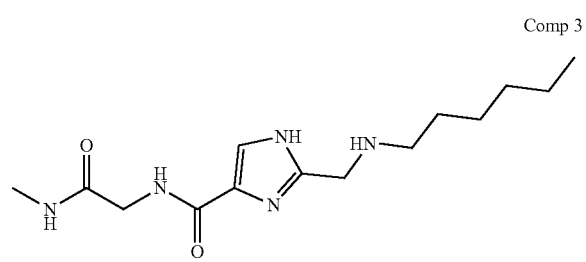

Comp 3

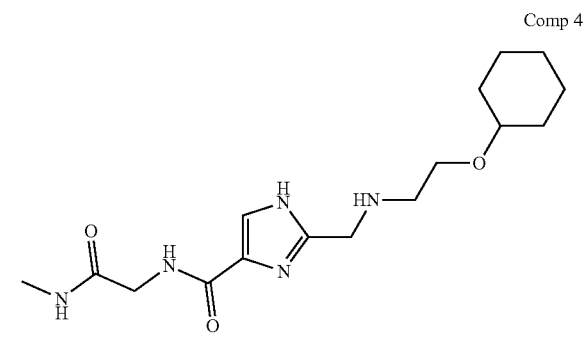

Comp 4

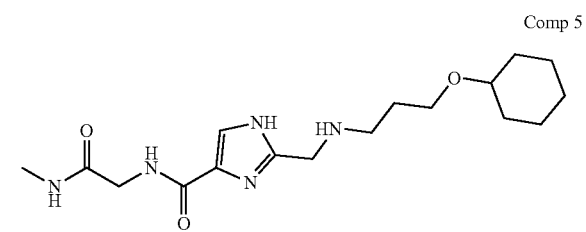

Comp 5

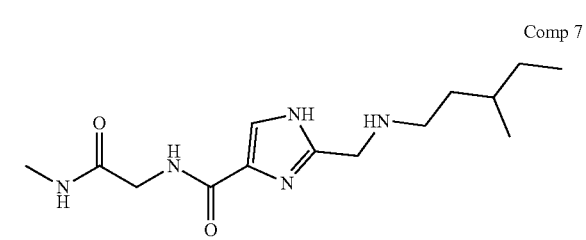

Comp 7

-continued

Comp 8
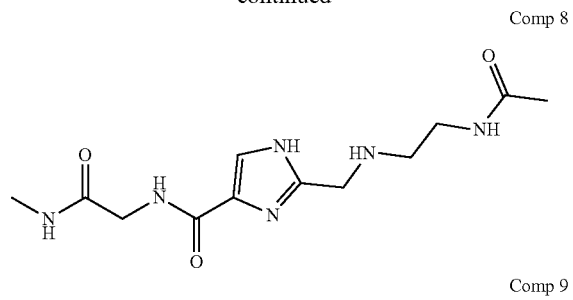

Comp 9
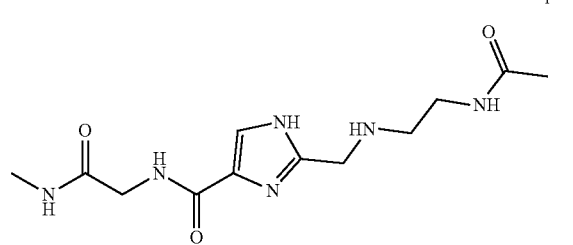

Comp 10
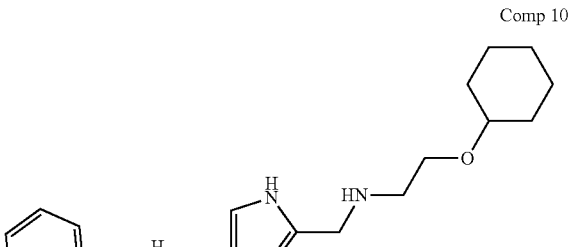

Comp 11
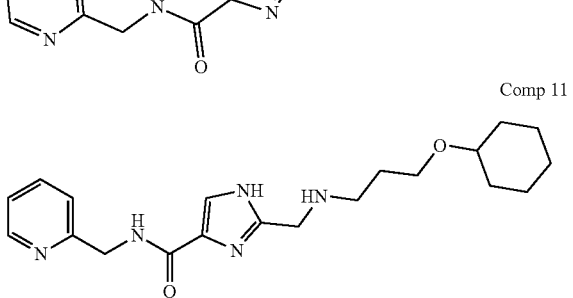

Comp 12
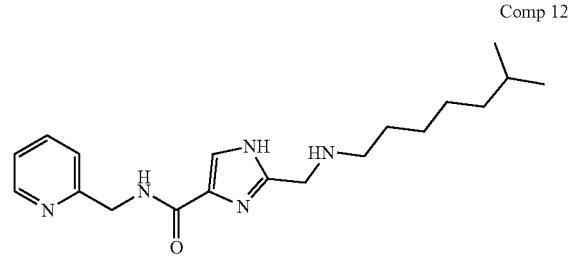

Comp 13
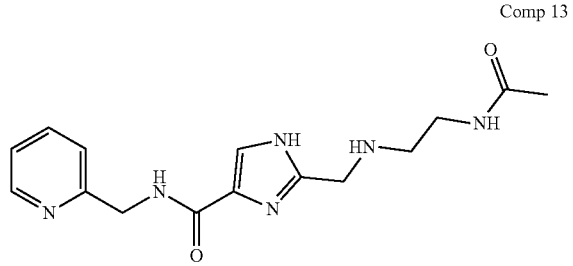

(Int-1) (Omar, Elfaky et al. 2020) was reacted with either 2-amino-N-methylglycinamide or 2-aminopyridine in the presence of a suitable coupling reagents such as, but not limited to, EDCI/HOBt. The resulting Int-2 had two functional groups attached to the imidazole nucleus, an ester and an amide. The ester was selectively reduced into the alcohol analogues by treatment with lithium aluminum hydride (LAH) in THF at 0° C. for suitable time. The produced alcohols belonged to Formula I and were confirmed using spectral analyses to have the following structures Comp 1

Comp 2

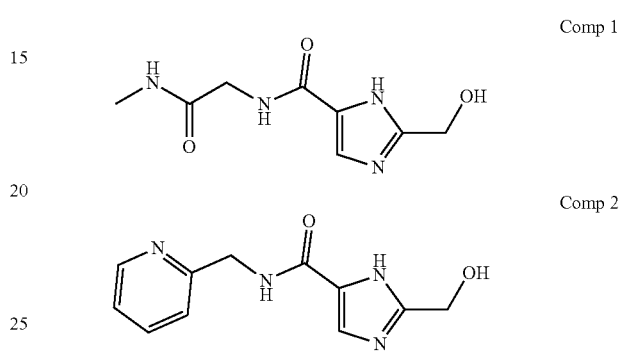

The alcohols Comp 1 and Comp 2 were used as precursors for the synthesis of further Examples of Formulae I and II described in this disclosure. The alcohols (Comp 1 and Comp 2) were first oxidized under controlled conditions that prevent further oxidation of the aldehydes. Example of these conditions is heating the alcohol to 80° C. after dissolving in dry N,N-dimethylformamide (DMF) containing an amount of 10 molar equivalent of manganese dioxide ($MnO_2$). The produced aldehydes were used directly to prepare the Examples belonging to Formula II:

Comp 3
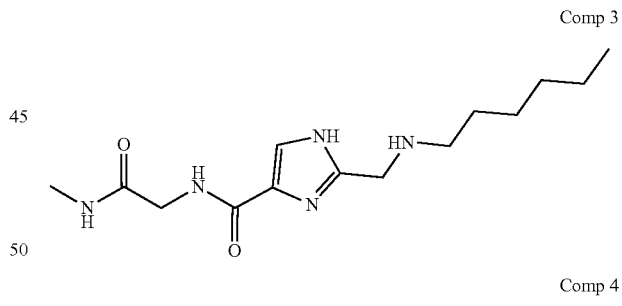

Comp 4
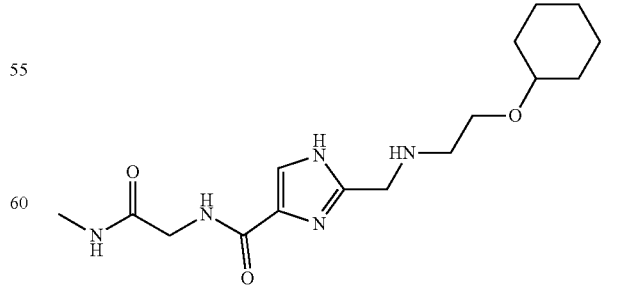

The compounds of formulae (I) and (II) may, for example, be synthesized according to a process illustrated in FIG. 3. Briefly, 2-(ethoxycarbonyl)-1H-imidazole-4-carboxylic acid Comp 5
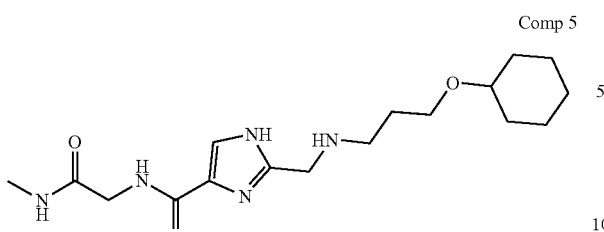

Comp 7
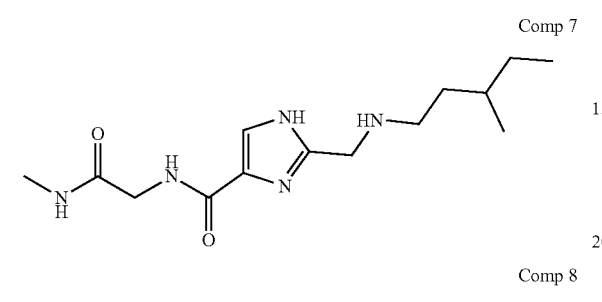

Comp 8
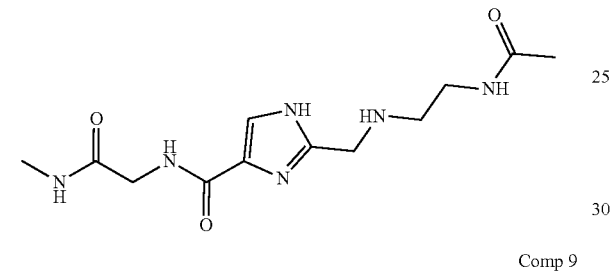

Comp 9
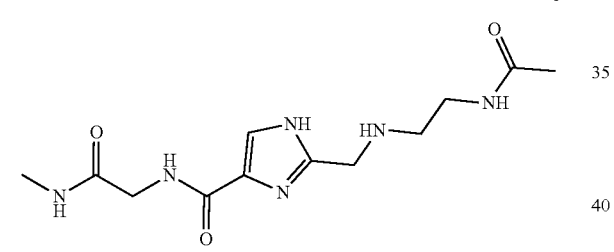

Comp 10
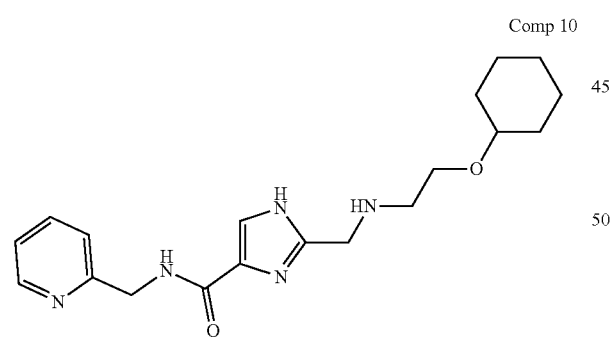

Comp 11
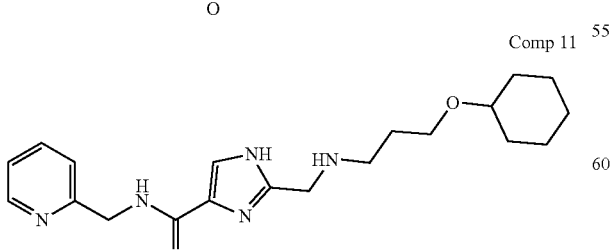

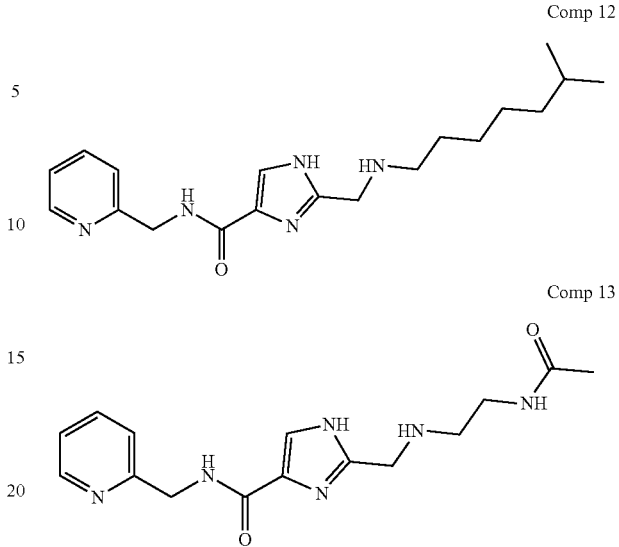

Comp 12

Comp 13

The method used to prepare Examples in this disclosure can be used for preparation of further compounds, not described in the Examples, of this disclosure, belonging to Formulae I and II. The compound of formulae (I) and (II) may be isolated and purified by methods known to those of ordinary skill in the art, such as crystallization, filtration through a celite containing cartridge, evaporating the reaction mixture to dryness, aqueous work-up, extraction with organic solvents, distillation, column chromatography, and high-pressure liquid chromatography (HPLC) on normal phase or reversed phase. Preferred methods include column chromatography and recrystallization.

An important aspect of the invention that the structure of compounds described as Examples in this disclosure are confirmed by several spectral analysis techniques such as proton nuclear magnetic resonance spectroscopy ($^1$H NMR), carbon-13 nuclear magnetic resonance spectroscopy ($^{13}$C NMR), mass spectrometry and ultraviolet-coupled high pressure liquid chromatography (LC-MS) (FIG. 2-FIG. 14).

In one embodiment, this disclosure relates compounds targeting NS4A site of binding to the HCV NS3 protein. The drug research and development efforts made by global research institutions and pharmaceutical industries that have been focused on other HCV targets rather than NS4A. Until our invention, NS4A binding pocket remained an underexplored target for discovering new antiviral agents, which may possibly overcome emerging resistance against available drugs.

Structurally, NS4A is a small peptide with 54 amino acids, which are inclined of forming proper assembly with other viral proteins. For instance, the hydrophobic N-terminal initiates a sandwich-filling binding that brings the N-terminal ($A_0$ and $A_1$ sheets) of the NS3 to rearrange and conform properly. This process is critical for the enzyme's catalytic site to attain a suitable shape that accommodates the peptide substrate (Failla, Tomei et al. 1994, Ishido, Fujita et al. 1998, De Francesco, Tomei et al. 2003, Hamad, Thurston et al. 2016, Tabata, Neufeldt et al. 2020, Iman, Mirza et al. 2024). It was found that the central part of NS4A (Gly21-Leu34) with only 14 amino acids is required for the activation of NS3 protease (Shimizu, Yamaji et al. 1996). El-Araby and Co-Workers identified that peptide mutants of NS4A$_{21-33}$, containing amino acid residues bulkier than the native peptide can bind to the NS3 protease in a higher potency. Further, they proved that these mutants prevented the viral NS4A$_{21-33}$ from binding to the viral NS3 protease. The NS3 protease, under the effect of bulky mutant was inhibited and unable to split a peptide substrate (El-Araby, Omar et al. 2020). In another direction the same research group designed imidazole-2,5-dicarboxamide as a first reported non-peptidic NS4A peptidomimetics. The compound N5-(4-guanidinobutyl)-N2-n-hexyl-1H-imidazole-2,5-dicarboxamide was able to prevent the viral NS4A$_{21-33}$ from binding to the HCV NS3 protease at competition potency expressed as a half maximal inhibitory concentration (IC$_{50}$) of 1.9 µM. This compound was also able to inhibit the HCV NS3 from functioning as a protease when mixed with a substrate peptide.

An aspect of this invention relates the distinction between the compounds of Formula I from the previously disclosed compounds because they feature only one carboxamide group and a novel substituted-aminomethyl group. This group is markedly more flexible and basic, contrary to the bis-amides disclosed previously by Omar et al (Omar, Elfaky et al. 2020). The bis-amides are non-basic, semi-rigid and more prone to metabolic hydrolysis (Kumari, Carmona et al. 2020). Reducing the bis-amid into a monoamide as depicted in Formula I is known to enhance the pharmacokinetic properties.

In another embodiment, 2-aminomethyl group of formula II is basic and, therefore, it acquires a positive charge in the physiological pH as follows:

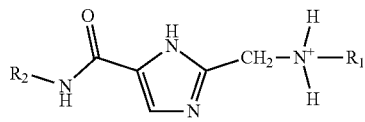

In a related aspect, formula (II) that has markedly different pharmacodynamic and binding properties with the protein's residues than other non-basic groups such as carboxamides, sulfonamides, ureas and carbamic acids. The disclosure explains surprising increases in the binding affinity over previously the bis-carboxamides.

In one embodiment of this disclosure, a suitable assay is used to characterize the ability of the active ingredient (e.g. compound of formulae I and II) in binding to the NS4A allosteric site. This may involve directly testing the active ingredient's ability to bind, and/or determining whether the active ingredient has an influence on the binding of the NS4A to HCV NS3 protease or variants thereof. To evaluate binding properties of binding compounds, assays may be used. Exemplary assay methods include, but not limited to, Differential Static Light Scattering (DSLS), calorimetric techniques, surface plasmon resonance (SPR), and spectroscopic methods such as NMR, fluorescence, and UV-vis spectroscopies.

In an embodiment, DSLS (Senisterra, Markin et al. 2006) is a preferred method to compare the relative binding potency for binding of a compound of Formula I with HCV NS3. DSLS measure the proteins aggregation temperature ($T_{agg}$) as an indicator of its stability (Davis, Walker et al. 2010). It is known that the binding of small molecules to proteins causes shifts of the aggregation temperature ($\Delta T_{agg}$) to higher temperature (Shahul Hameed, Haider et al. 2018). One aspect of this invention is using $\Delta T_{agg}$ determination as a method to determine the potency of binding of compounds belonging to formula I to the HCV NS3 protease, in comparison to the native NS4A.

Figure 30:
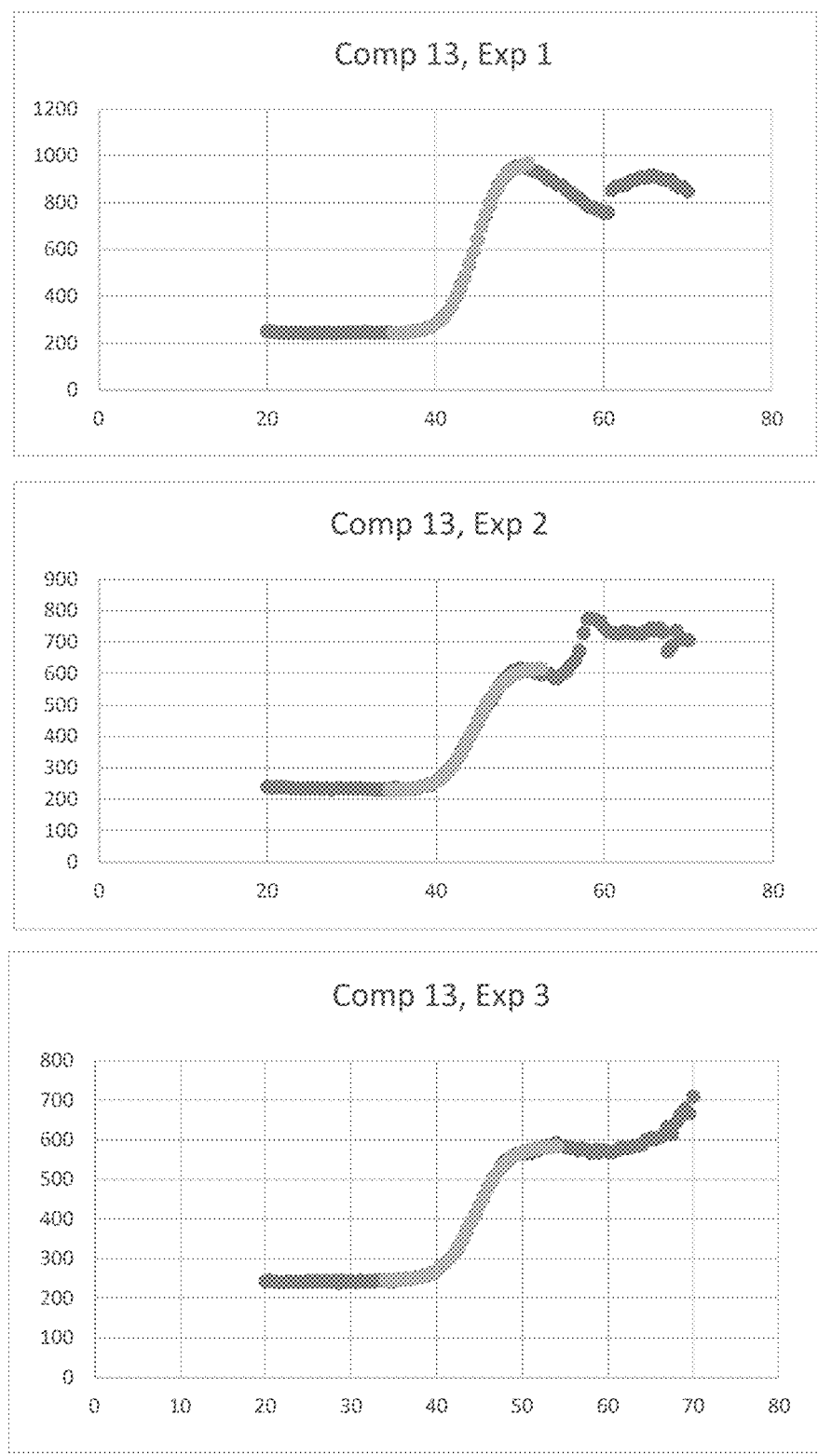
FIG. 30. Plots of three DSLS experiments of NS3+Comp 13: protein X axis is temperature (° C.) and Y axis is the relative light intensity compared to blank.
Figure 32:
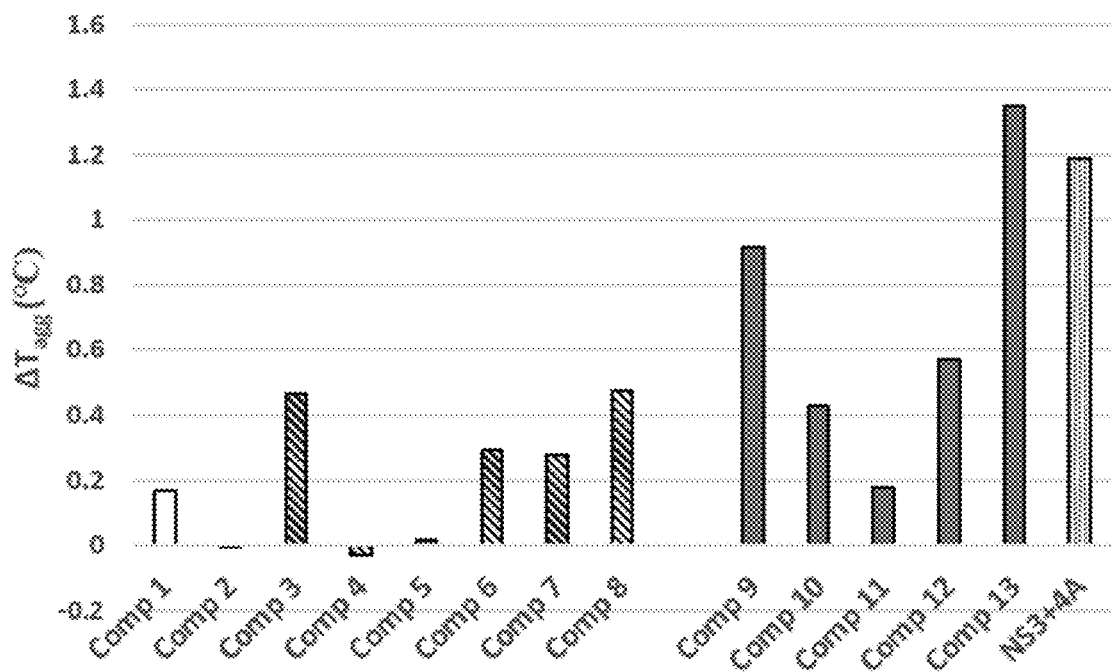
FIG. 32. Figures of three experiments of DSLS measuring the $T_{agg}$ values and calculation of the average

In one embodiment, Comp 13, belonging to formulae I and II demonstrated equal or higher affinity towards the HCV NS3 protein when compared to the native viral peptide cofactor NS4A (FIG. 30, FIG. 31 and FIG. 32).

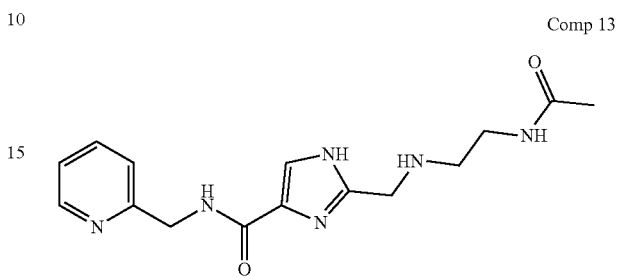

Comp 13

An important aspect of the present disclosure is securing the intellectual property rights associated with Formulae I, II exemplified by the novel compounds Comp 1 to Comp 13 as candidates for new therapeutics either alone or combined with other drugs for treatment of hepatitis C infection due to their significant binding affinities towards HCV NS3 protein.

The examples below are intended to further illustrate protocols for preparing, characterizing the compound of formulae (I) and (II), and uses thereof, and are not intended to limit the scope of the claims.

Example 1

Synthesis of Screened Compounds

The compounds were synthesized using straightforward chemistry (Duguay, Guémas et al. 1980, Zam, Barrett et al. 2001, Vuilhorgne, Malpart et al. 2003) each incorporated herein by reference in their entirety] as illustrated in the synthesis scheme (FIG. 1). All final compounds are new and their structures were confirmed by spectral analyses (e.g. $^1$H NMR, $^{13}$C NMR, and LC/MS).

Example 2

Chemical Synthesis: General

Solvents and reagents were purchased from Sigma-Aldrich (USA), Avantor (USA) or Fisher Scientific (UK). When needed, solvents were dried according procedures described in literature. Unless stated otherwise, reactions were performed under inert atmosphere of nitrogen. Melting points (m.p.) were determined in open capillary tubes using Electrothermal apparatus (Stuart, UK) and were uncorrected. NMR spectra were recorded on Bruker DPX-300 MHz (Bruker, Switzerland). HPLC-Mass Spectrometry was performed on Agilent 1100/ZQ MSD including diod-array UV detector.

Example 3

General Method for the Synthesis of Int-2a and Int-2b (FIG. 1)

Under inert atmosphere, Int-1 (1 equiv.) was dissolved in dry THF (5 mL/mmol) then 1-Ethyl-3-(3-dimethylaminopropyl)carbodiimide (EDCI, 1.0 equiv.), 1-hydroxybenzotriazole (HOBt, 1.0 equiv.), Diisopropyl ethyl amine (DIPEA, 1.5 equiv.) and the proper amine (1.2 equiv) were added. The mixture was stirred at rt for 1 h then heated to 60° C. After completion, the mixture was purified by column chromatography using 50-100% EtOAc in cyclohexane.

Int 2a: Ethyl 4-((2-(methylamino)-2-oxoethyl)carbamoyl)-1H-imidazole-2-carboxylate The final product was purified via column chromatography using 0-15% MeOH in CHCl₃ (3.7 g, 76%).

Int 2b: Ethyl 5-((pyridin-2-ylmethyl)carbamoyl)-1H-imidazole-2-carboxylate

The final product was purified via column chromatography using 0-10% MeOH in CHCl₃ (560 mg, 94%).

Example 4

Synthesis of 2-(hydroxymethyl)-N-(2-(methylamino)-2-oxoethyl)-1H-imidazole-5-carboxamide (Comp 1)

Imidazole-2-carboxylic acid derivative (Int. 2a, 1.0 equiv) was dissolved in THF (3 mL/mmol) then lithium aluminum hydride (LAH) (4.0 equiv) was added. The mixture was stirred at 0° C. for 60 min After completion of the reaction the mixture was quenched by the addition of MeOH (5 mL/mmol) then evaporated and the product was purified via column chromatography using 0-30% MeOH in DCM (307 mg, 76%), Mp: 189-91° C. 1H NMR (300 MHz, DMSO-$d_6$) δ ppm 2.60 (d, J=4.33 Hz, 3H) 3.84 (d, J=5.65 Hz, 2H) 4.44-4.80 (m, 2H) 7.72-8.02 (m, 2H) 8.57 (br. s., 1H); LCMS: m/z 213.2 (M+H)$^+$, RT 2.46 min, 93%.

Example 5

Synthesis of 2-(hydroxymethyl)-N-(pyridin-2-ylmethyl)-1H-imidazole-4-carboxamide (Comp 2)

Imidazole-2-carboxylic acid derivative Int-2b (1.0 g, 3.6 mmol, 1.0 equiv) was dissolved in THF (3 mL/mmol) then LAH (4.0 equiv.) was added. The mixture was stirred at 0° C. for 20 min. After completion of the reaction the mixture was quenched by the addition of H₂O (0.25 mL/mmol) then evaporated and the product was purified via column chromatography using 0-30% MeOH in DCM (580 mg, 69%), Mp: 174-5° C. ¹H NMR 1H NMR (300 MHz, METHANOL-$d_4$) δ ppm 4.68 (d, J=9.98 Hz, 5H) 7.26-7.39 (m, 1H) 7.45 (d, J=7.72 Hz, 1H) 7.67 (s, 1H) 7.83 (t, J=7.16 Hz, 1H) 8.51 (d, J=4.33 Hz, 1H); LCMS: m/z 233.3 (M+H)$^+$, RT 2.77 min.

Example 6 General Method for Synthesis of Comp 3 to Comp 13

The starting alcohol (Comp 2 or Comp 3) was dissolved in dry N,N-dimethylformamide (DMF) (15 mL/mmol) and MnO₂ (10.0 equiv.) was added to the mixture. The reaction was stirred at 80° C. for 2 h. After completion the mixture was filtered, evaporated and triturated with small amount of DCM and n-heptane. The precipitated aldehyde product was collected by filtration and purified by column chromatography using 0-20% MeOH in CHCl₃. An appropriate amount of the aldehyde (1 equiv.), dissolved in EtOH (4 mL/mmol) and amine was added (1.1 equiv.) followed by acetic acid (0.1 equiv) to the mixture and stirred at room temp for 30 min. NaBH(OAc)₃ (2.0 equiv) was added to the reaction and stirred at Room temp for sufficient time. After completion, the mixture was diluted with MeOH and purified using preparative HPLC.

Comp 3: 2-((hexylamino)methyl)-N-(pyridin-2-ylmethyl)-1H-imidazole-5-carboxamide This compound was produced in a yield 48 mg (62.5%) as a transparent oily substance. ¹H NMR (300 MHz, METHANOL-$d_4$) δ ppm 0.87-1.02 (m, 4H), 1.40 (br. s., 6H) 1.74 (d, J=7.35 Hz, 2 H) 3.09-3.22 (m, 2H) 4.03 (s, 2H) 4.33 (s, 32H) 7.73 (s, 1H). ¹³C NMR (75 MHz, METHANOL-$d_4$) ☐ 48.5, 48.2, 47.9, 47.6, 47.5, 47.4, 47.1, 46.8, 31.0, 25.8, 25.8, 24.9, 22.1, 12.9; LC-MS (ESI), RT=2.27 min, m/z 296.4 [M+H]$^+$.

Comp 4: 2-(((2-(cyclohexyloxy)ethyl)amino)methyl)-N-(2-(methylamino)-2-oxoethyl)-1H-imidazole-5-carboxamide This compound was produced in a yield 115 mg, 50.9% as an oil. ¹H NMR (300 MHz, METHANOL-$d_4$) δ 7.72 (s, 1H), 4.36 (s, 2H), 4.03 (s, 2H), 3.79 (t, J=4.99 Hz, 2H), 2.78 (s, 3H), 1.96 (br. s., 2H), 1.70-1.88 (m, 2H), 1.58 (d, J=7.35 Hz, 1H), 1.08-1.48 (m, 5H); ¹³C NMR (75 MHz, METHANOL-$d_4$) δ 78.2, 62.5, 48.5, 48.2, 47.9, 47.6, 47.5, 47.4, 47.1, 46.8, 43.3, 41.7, 31.7, 25.5, 25.0, 23.6; LC-MS (ESI), RT=2.36 min, m/z 338.4 [M+H]$^+$ Comp 5: 2-(((3-(cyclohexyloxy)propyl)amino)methyl)-N-(2-(methylamino)-2-oxoethyl)-1H-imidazole-5-carboxamide This compound was produced in a yield 130 mg, 46.7% as an oil. ¹H NMR (300 MHz, METHANOL-$d_4$) δ 7.55-7.90 (m, 1H), 4.36 (s, 2H), 4.03 (s, 2H), 3.65 (t, J=5.56 Hz, 2H), 3.20-3.46 (m, 4H), 1.81-2.13 (m, 4H), 1.72 (br. s., 2H), 1.45-1.60 (m, 1H), 1.29 (d, J=7.35 Hz, 5H); ¹³C NMR (75 MHz, METHANOL-$d_4$) δ 77.8, 64.9, 48.5, 48.2, 47.9, 47.6, 47.4, 47.1, 46.8, 46.2, 43.2, 41.6, 31.7, 26.2, 25.5, 24.9, 23.6; LC-MS (ESI), RT=2.36 min, m/z 352.4 [M+H]$^+$.

Comp 6: N-(2-(methylamino)-2-oxoethyl)-2-(((6-methylheptyl)amino)methyl)-1H-imidazole-4-carboxamide This compound was produced in a yield 129 mg, 59.53% as an oil. ¹H NMR (300 MHz, METHANOL-$d_4$) δ 7.74 (s, 1H), 4.35 (s, 2H), 3.88-4.20 (m, 2H), 3.10 (d, J=6.78 Hz, 2H), 2.79 (s, 3H), 1.64-1.87 (m, 1H), 1.20-1.59 (m, 9H), 0.96 (t, J=7.35 Hz, 7H); ¹³C NMR (75 MHz, METHANOL-$d_4$) δ 121.4, 50.9, 48.5, 48.2, 47.9, 47.6, 47.4, 47.1, 46.8, 43.7, 41.6, 36.8, 30.0, 28.1, 24.9, 23.2, 22.5, 12.9, 9.2; LC-MS (ESI), RT=2.13 min, m/z 324.44 [M+H]$^+$ Comp 7: N-(2-(methylamino)-2-oxoethyl)-2-(((3-methylpentyl)amino)methyl)-1H-imidazole-5-carboxamide This compound was produced in a yield 129 mg, 59.5% as an oil. ¹H NMR (300 MHz, METHANOL-$d_4$) δ 7.72 (s, 1H), 4.35 (s, 2H), 4.03 (s, 2H), 3.04-3.28 (m, 2H), 2.78 (s, 3H), 1.66-1.91 (m, 1H), 1.36-1.63 (m, 3H), 1.13-1.35 (m, 1H), 0.78-1.11 (m, 7H); ¹³C NMR (75 MHz, METHANOL-$d_4$) δ 121.4, 48.5, 48.2, 47.9, 47.6, 47.4, 47.1, 46.8, 46.0, 43.1, 41.7, 32.3, 32.2, 28.9, 25.0, 17.8, 10.1; LC-MS (ESI), RT=2.46 min, m/z 213.2 [M+H]$^+$ Comp 8: 2-(((2-acetamidoethyl)amino)methyl)-N-(2-(methylamino)-2-oxoethyl)-1H-imidazole-5-carboxamide This compound was produced in a yield 79 mg, 39.79% as a solid, Mp 133-4° C. $^1$H NMR (300 MHz, METHANOL-d$_4$) δ 7.72 (s, 1H), 4.37 (s, 2H), 3.94-4.16 (m, 2H), 3.56 (d, J=5.09 Hz, 2H), 2.78 (s, 4H), 1.85-2.07 (m, 3H); $^{13}$C NMR (75 MHz, METHANOL-d$_4$) δ 48.5, 48.2, 47.9, 47.6, 47.4, 47.1, 46.8, 35.9, 25.0, 21.2; LC-MS (ESI), RT=3.34 min, m/z 297.4 [M+H]$^+$ Comp 9: 2-((hexylamino)methyl)-N-(pyridin-2-ylmethyl)-1H-imidazole-4-carboxamide This compound was produced in a yield 103 mg, 62.0% as an oily material. $^1$H NMR (300 MHz, METHANOL-d$_4$) δ 8.63 (d, J=4.90 Hz, 1H), 8.14 (t, J=7.16 Hz, 1H), 7.77 (s, 1H), 7.68 (d, J=7.91 Hz, 1H), 7.61 (t, J=6.31 Hz, 1H), 4.79 (s, 2H), 4.34 (s, 2H), 3.07-3.24 (m, 2H), 1.59-1.87 (m, 2H), 1.39 (br. s., 6H), 0.85-1.04 (m, 3H); $^{13}$C NMR (75 MHz, METHANOL-d$_4$) δ 123.9, 123.5, 48.5, 48.2, 47.9, 47.6, 47.5, 47.3, 47.1, 46.8, 43.1, 42.2, 31.0, 25.8, 25.7, 22.1, 12.9; LC-MS (ESI), RT=2.50 min, m/z 316.4 [M+H]$^+$.

Comp 10: 2-(((2-(cyclohexyloxy)ethyl)amino)methyl)-N-(pyridin-2-ylmethyl)-1H-imidazole-5-carboxamide This compound was produced in a yield 53 mg, 56.9% as an oil. $^1$H NMR (300 MHz, METHANOL-d$_4$) δ 8.74 (d, J=5.27 Hz, 1H), 8.30-8.54 (m, 1H), 7.67-7.99 (m, 4H), 4.39 (s, 2H), 3.80 (t, J=4.99 Hz, 2H), 3.35-3.52 (m, 4H), 1.96 (br. s., 2H), 1.78 (br. s., 2H), 1.68 (d, J=6.97 Hz, 1H), 1.59 (d, J=8.29 Hz, 1H), 1.16-1.50 (m, 5H); $^{13}$C NMR (75 MHz, METHANOL-d$_4$) δ 142.7, 124.9, 78.2, 62.3, 48.5, 48.2, 47.9, 47.6, 47.4, 47.1, 46.8, 31.6, 25.4, 23.6; LC-MS (ESI), RT=2.59 min, m/z 358.4 [M+H]$^+$.

Comp 11: 2-(((3-(cyclohexyloxy)propyl)amino)methyl)-N-(pyridin-2-ylmethyl)-1H-imidazole-5-carboxamide This compound was produced in a yield 25 mg, 25.9% as an oily substance. $^1$H NMR (300 MHz, METHANOL-d$_4$) δ 8.64 (d, J=4.90 Hz, 1H), 8.14 (t, J=7.82 Hz, 1H), 7.77 (s, 1H), 7.69 (d, J=8.10 Hz, 1H), 7.54-7.65 (m, 1H), 4.79 (s, 2H), 4.36 (s, 2H), 3.64 (t, J=5.65 Hz, 2H), 1.94-2.10 (m, 2H), 1.89 (br. s., 2H), 1.69 (br. s., 2H), 1.46-1.60 (m, 1H), 1.27 (d, J=8.67 Hz, 5H); $^{13}$C NMR (75 MHz, METHANOL-d$_4$) δ 123.8, 77.7, 64.9, 48.5, 48.2, 47.9, 47.6, 47.4, 47.1, 46.8, 46.2, 43.2, 42.3, 31.7, 26.2, 25.5, 23.6; LC-MS (ESI), RT=2.70 min, m/z 372.4 [M+H]$^+$ Comp 12: Synthesis of 2-(((6-methylheptyl)amino)methyl)-N-(pyridin-2-ylmethyl)-1H-imidazole-5-carboxamide This compound was produced in a yield 129 mg, 73.3% as an oily residue. 1H NMR (300 MHz, METHANOL-d$_4$) δ ppm 0.94 (t, J=7.35 Hz, 6H) 1.22-1.57 (m, 9H) 1.61-1.84 (m, 1H) 3.10 (d, J=6.59 Hz, 2H) 4.37 (s, 2H) 7.71-7.93 (m, 3H) 8.36 (t, J=7.35 Hz, 1H) 8.72 (d, J=5.09 Hz, 1H); 13C NMR (75 MHz, METHANOL-d$_4$) δ ppm 9.14, 12.94, 22.48, 23.14, 28.08, 29.08, 29.96, 36.80, 41.38, 43.68, 46.78, 47.07, 47.35, 47.63, 47.92, 48.20, 48.49, 50.88, 121.82, 124.53, 124.62, 124.68, 135.36, 139.66, 143.40, 143.86, 155.48, 163.93; LC-MS (ESI), RT=0.95 min, m/z 344.4 [M+H]$^+$.

Comp 13: Synthesis of 2-(((2-acetamidoethyl)amino)methyl)-N-(pyridin-2-ylmethyl)-1H-imidazole-5-carboxamide This compound was produced in a yield of 70 mg, 85.1% as a solid Mp. 166-8° C. $^1$H NMR (300 MHz, METHANOL-d$_4$) δ ppm 2.01 (s, 3H) 3.36 (s., 2H) 3.51-3.63 (m, 2H) 4.39 (s, 2H) 4.83 (s., 2H) 7.71-7.83 (m, 2H) 7.87 (d, J=8.10 Hz, 1H) 8.29-8.42 (m, 1H) 8.71 (d, J=4.71 Hz, 1H); $^{13}$C NMR (75 MHz, METHANOL-d$_4$) δ 48.5, 48.2, 47.9, 47.8, 47.6, 47.4, 47.1, 46.8, 35.9, 21.1; LC-MS (ESI), RT=3.43 min, m/z 317.3 [M+H]$^+$ Example 6

Biological Screening: General

All reagents used in the biological screenings were purchased from Millipore-Sigma (UK) of molecular biology grade unless stated otherwise.

Example 7

NS3 Protein
(i) NS3 Constructs
A synthetic gene coding for the HCV NS3 domain of genotype 4a, the most abundant HCV in Saudi Arabia and Egypt (Massariol, Zhao et al. 2010), was synthesized by GenScript (Hong Kong), the nucleotide sequence was optimized for E. coli codon usage. The synthetic gene was cloned as NdeI-BamHI fragment into the expression vector pET-3a Novagen®. The obtained construct was sequenced to confirm that we had the right clone and the gene was in the correct frame.
(ii) NS3 Protein Information
  Accession GU085486.1
  HCV genotype 4a (The most common genotype in Saudi Arabia) (Bawazir, AlGusheri et al. 2017)
  NS3 from 4 to 182 aa (L/E, F/E, I/Q, V/E, L/Q, C/S)
  NS4A 632 to 685 aa (i/n)
  G svvivgrvnl sgdtayaqqt rgeestqets qtgrdtnenc gevqvlstat qsflgtavng vmwtvyhgag sktisgpkgp vnqmytnvdq dlvgwpsppg vksltpctcg asdlylvtrh advvpvrrrg dtrgallspr pistlkgssg gpllcpmgha aglfraavst rgvakavdfv pveslett mrsp (SEQ ID NO. 1)
  NS4A/NS3 Fusion protein expression in pET-28a
  NS3 protease domain 1-181 aa+N-terminal T7 tag and C-terminal His tag
  M ASMTGGQQMG apitayaqqt rglfstivts ltgrdtnenc gevqvlstat qsflgtavng vmwtvyhgag sktisgpkgp vnqmytnvdq dlvgwpsppg vksltpctcg asdlylvtrh advvpvrrrg dtrgallspr pistlkgssg gpllcpmgha aglfraavct rgvakavdfv pveslettmr sGSHHHHHH (SEQ ID NO. 2)
  Expression in pET-3a
(iii) Protein eNS4Axpression
The sequence of NS3 domain for genotype 4a, was expressed in E. coli Rosette (DE3) pLysS according to standard protocol (Kim, Morgenstern et al. 1996). Therefore, a synthetic gene for NS3 domain was subcloned in the expression vector pET-3a. In the process, a 100 mL of bacterial culture in Luria Broth medium was grown overnight at 37° C. and used for inoculation of 10 L LB in a 14-liter fermenter flask (New Brunswick Scientific Co., CT, USA). The media was supplemented with 50 µg/mL ampicillin. The culture grew until the $OD_{600}$ reached 0.5-0.6, then it was cooled to 25° C. and 1 mM IPTG was added. Expression was followed overnight, and then cells were harvested.

(iv) Protein Purification

The produced protein was purified using equilibrated Ni-NTA beads and the poly-histidine tag was not removed. In the process, cells were re-suspended (1 g/5 mL) in buffer (50 mM HEPES, 0.3 M NaCl, 10% glycerol, 2 mM β-mercaptoethanol, pH 8). Lysozymes were added (1 mg/mL) followed by protease inhibitor cocktail tablet and the suspension was sonicated. Cell lysate was centrifuged to collect the clear supernatant that contained the desired NS3 protein. The protein was purified using pre-equilibrated Ni-NTA beads (Qiagen, USA). Beads were washed with buffer (50 mM HEPES, 0.3 M NaCl, 10% glycerol, 2 mM β-mercaptoethanol, 20 mM imidazole, pH 8) and eluted with another buffer (50 mM HEPES, 0.3 M NaCl, 10% glycerol, 2 mM β-mercaptoethanol, 350 mM imidazole, pH 8). Fractions were collected and concentrated using Amicon Ultra-4 3000 MWCO centrifugal device (Millipore, Germany). Protein purity after Ni-affinity purification step was not less than 70%. The purity, as estimated by SDS-PAGE, was sufficient to perform all investigations of this study and the protein was stable for several hours at test conditions (Massariol, Zhao et al. 2010, El-Araby, Omar et al. 2020). The concentration of NS3 in the final concentrate was measured using Nanodrop™ nanoscale spectrophotometer.

When needed, further purification of the protein was accomplished on Superdex 75 16/90 column (GE Healthcare, USA) equilibrated in 20 mM HEPES, 10 mM DDT, 200 mM NaCl, pH 7.6 run at rate of 1 mL/min followed by SDS-PAGE for purity estimation.

Example 8

NS4A

The cofactor NS4A and the fluorescent fluorescein isothiocyanate NS4A (FITC-NS4A) were purchased from GenScript (Hong Kong). NS4A structure was identical to that of HCV genotype 4a with two lysine residues added at both the N- and C-termini. Thus the structure of NS4A used in this study was LL-$G_{21}$SVVIVGRIVLS$G_{33}$-LL.

Example 9

Binding Assay

The NS3 domain (15.0 µM), alone or mixed with an equimolar equivalent of tested compound or the NS4A, was added to a binding buffer (20.0 mM HEPES, 10.0 mM DTT, 200 mM NaCl, pH 7.60) to a final volume 100 µL. The mixture was incubated at room temperature with gentle shaking for 2 h. Afterwards, 10 µL of the mixture was transferred into a clear bottomed Nunc 384-well plate and covered by 10 µL paraffin oil to minimize evaporation. Protein aggregation was monitored by tracking the change in scattered light that was detected by a charged coupled device (CCD) camera. Snapshot images of the plate were taken every 0.5° C. The pixel intensities in a preselected region of each well were integrated using image analysis software to generate a value representative of the total amount of scattered light in that region. These intensities were then plotted against temperature for each sample well and fitted to obtain the aggregation temperature ($T_{agg}$). Aggregation was monitored and analyzed to assess the effect of NS4A and its synthetic analogues on the stability of the NS3 as an indicator of binding. Each experiment was repeated three times (Triplicate). Statistical analysis was performed using GraphPad Prism v. 8.0® and Instat® v. 3.10 software. The $T_{agg}$ for the compound was only considered if its SD >25% of the calculated $T_{agg}$ value.

Example 10

Biological Screening Results

Under this assay conditions, the NS3 protein alone or mixed with equimolar amounts of test compound exhibited ideal aggregation sigmoid curve (light-grey portion, FIG. 15 to FIG. 29). Each experiment was run as triplicate (Experiment 1, 2 and 3) and the standard deviations (ST.DEV.) were calculated. (results table FIG. 31).

As illustrated in FIG. 32 the NS3 protein alone had Comp 13 had a $T_{agg}$ at 43.22° C. Mixing the NS3 with equimolar amount of the NS4 resulted in $T_{agg}$=44.40° C. This increase is comparable to our previous findings (El-Araby, Omar et al. 2020). Mixing test compounds (Comp 1 to Comp 13) with an equimolar amount of NS3 protein resulted in valid $T_{agg}$ within the required ST.DEV limits. Compound 13 caused the highest stabilization of the protein among the tested compounds ($T_{agg}$=44.40° C.). As shown in FIG. 32, The $\Delta T_{agg}$ which is considered a good indicator of the relative binding potency was 1.35° C., a higher shift than that of the HCV NS4A by 14%. One aspect of this disclosure is the ability of the described compounds of Formula (I) to bind to the NS3 to be administered for treatment of hepatitis C infections. Compound 13 strongly binds to the NS3 followed by Comp 9 ($\Delta T_{agg}$=0.91° C.), Comp 12 ($\Delta T_{agg}$=0.57° C.), Comp 8 ($\Delta T_{agg}$=0.48° C.), Comp 3 ($\Delta T_{agg}$=0.47° C.) and Comp 10 ($\Delta T_{agg}$=0.43° C.).

Acknowledgment of Sponsored Research

This invention was made with funds provided by the Deanship of Scientific Research (DSR) at King Abdulaziz University, Jeddah, under grant no GCV19-20-1441. The authors, therefore, acknowledge with thanks DSR for technical support.

REFERENCES

Bawazir, A., F. AlGusheri, H. Jradi, M. AlBalwi and A. G. Abdel-Gader (2017). "Hepatitis C virus genotypes in Saudi Arabia: a future prediction and laboratory profile." *Virol J* 14(1): 208.

Chhatwal, J., Q. Chen and R. Aggarwal (2018). "Estimation of hepatitis C disease burden and budget impact of treatment using health economic modeling." *Infectious Disease Clinics* 32(2): 461-480.

Ci, Y. and L. Shi (2021). "Compartmentalized replication organelle of flavivirus at the ER and the factors involved." *Cell Mol Life Sci* 78(11): 4939-4954.

Cui, F., S. Blach, C. M. Mingiedi, M. A. Gonzalez, A. S. Alaama, A. Mozalevskis, N. Séguy, B. B. Rewari, P.-L. Chan and L.-v. Le (2023). "Global reporting of progress towards elimination of hepatitis B and hepatitis C." *The lancet Gastroenterology & hepatology* 8(4): 332-342.

Davis, T. L., J. R. Walker, V. Campagna-Slater, P. J. Finerty Jr, R. Paramanathan, G. Bernstein, F. MacKenzie, W. Tempel, H. Ouyang and W. H. Lee (2010). "Structural and biochemical characterization of the human cyclophilin family of peptidyl-prolyl isomerases." *PLoS biology* 8(7): e1000439.

De Francesco, R., L. Tomei, S. Altamura, V. Summa and G. Migliaccio (2003). "Approaching a new era for hepatitis C virus therapy: inhibitors of the NS3-4A serine protease and the NS5B RNA-dependent RNA polymerase." *Antiviral research* 58(1): 1-16.

Dietz, J., B. Müllhaupt, P. Buggisch, C. Graf, K. H. Peiffer, K. Matschenz, J. M. Schattenberg, C. Antoni, S. Mauss, C. Niederau, T. Discher, J. Trauth, G. Dultz, J. Schulze Zur Wiesch, F. Piecha, H. Klinker, T. Müller, T. Berg, C. Neumann-Haefelin, C. P. Berg, S. Zeuzem and C. Sarrazin (2023). "Long-term persistence of HCV resistance-associated substitutions after DAA treatment failure." *J Hepatol* 78(1): 57-66.

Duguay, G., J. P. Guémas, J. C. Meslin, J. P. Pradere, F. Reliquet, A. Reliquet, C. Tea-Gokou, H. Quiniou and C. Rabiller (1980). "Heteroatomic chains and their products of cyclisation. IV. t-butyl-2-phthalimido-2-(3, 6-dihydro-1, 3-2H-thiazine-2-yliden)-acetates substituted in position 5 by a functional group." *Journal of Heterocyclic Chemistry* 17(4): 767-770.

El-Araby, M. E., A. M. Omar, S. H. Soror, S. T. Arold, M. T. Khayat, H. Z. Asfour, F. Bamane and M. A. Elfaky (2020). "Synthetic bulky NS4A peptide variants bind to and inhibit HCV NS3 protease." *Journal of Advanced Research* 24: 251-259.

Failla, C., L. Tomei and R. De Francesco (1994). "Both NS3 and NS4A are required for proteolytic processing of hepatitis C virus nonstructural proteins." *Journal of virology* 68(6): 3753-3760.

Gould, E. and T. Solomon (2008). "Pathogenic flaviviruses." *The Lancet* 371(9611): 500-509.

Haber, P. S., M. M. Young, L. Dorrington, A. Jones, J. Kaldor, S. De Kanzow and W. D. Rawlinson (2007). "Transmission of hepatitis C virus by needle-stick injury in community settings." *Journal of gastroenterology and hepatology* 22(11): 1882-1885.

Hamad, H. A., J. Thurston, T. Teague, E. Ackad and M. S. Yousef (2016). "The NS4A cofactor dependent enhancement of HCV NS3 protease activity correlates with a 4D geometrical measure of the catalytic triad region." *PLoS One* 11(12): e0168002.

Hellard, M. E., R. Chou and P. Easterbrook (2017). *WHO guidelines on testing for hepatitis B and C-meeting targets for testing, Springer.* 17: 1-7.

Hill, A. M., S. Nath and B. Simmons (2017). "The road to elimination of hepatitis C: analysis of cures versus new infections in 91 countries." *Journal of virus eradication* 3(3): 117-123.

Iman, K., M. U. Mirza, F. Sadia, M. Froeyen, J. F. Trant and S. U. Chaudhary (2024). "Pharmacophore-Assisted Covalent Docking Identifies a Potential Covalent Inhibitor for Drug-Resistant Genotype 3 Variants of Hepatitis C Viral NS3/4A Serine Protease." *Viruses* 16(8): 1250.

Indolfi, G. and M. Resti (2009). "Perinatal transmission of hepatitis C virus infection." *Journal of medical virology* 81(5): 836-843.

Ishido, S., T. Fujita and H. Hotta (1998). "Complex formation of NS5B with NS3 and NS4A proteins of hepatitis C virus." *Biochemical and biophysical research communications* 244(1): 35-40.

Izhari, M. A. (2023). "Molecular Mechanisms of Resistance to Direct-Acting Antiviral (DAA) Drugs for the Treatment of Hepatitis C Virus Infections." *Diagnostics* 13(19): 3102.

Khayat, M. T., A. M. Omar, M. A. Elfaky, Y. A. Muhammad, E. A. Felemban, K. M. El-Say and M. E. El-Araby (2022). "Reexamining Povarov Reaction's Scope and Limitation in the Generation of HCV-NS4A Peptidomimetics." *Heteroatom Chemistry* 2022(1): 8181543.

Kim, J. L., K. A. Morgenstern, C. Lin, T. Fox, M. D. Dwyer, J. A. Landro, S. P. Chambers, W. Markland, C. A. Lepre, E. T. O'Malley, S. L. Harbeson, C. M. Rice, M. A. Murcko, P. R. Caron and J. A. Thomson (1996). "Crystal structure of the hepatitis C virus NS3 protease domain complexed with a synthetic NS4A cofactor peptide." *Cell* 87(2): 343-355.

Kumari, S., A. V. Carmona, A. K. Tiwari and P. C. Trippier (2020). "Amide Bond Bioisosteres: Strategies, Synthesis, and Successes." *J Med Chem* 63(21): 12290-12358.

Lauer, G. M. and B. D. Walker (2001). "Hepatitis C virus infection." *New England journal of medicine* 345(1): 41-52.

Lewis, K. C., L. K. Barker, R. B. Jiles and N. Gupta (2023). "*Estimated Prevalence and Awareness of Hepatitis C Virus Infection Among US Adults: National Health and Nutrition Examination Survey*, January 2017-March 2020." Clinical Infectious Diseases 77(10): 1413-1415.

Lynch, E. N. and F. P. Russo (2023). "Outcomes and Follow-Up after Hepatitis C Eradication with Direct-Acting Antivirals." *Journal of Clinical Medicine* 12(6): 2195.

MacDonald, M., N. Crofts and J. Kaldor (1996). "Transmission of hepatitis C virus: rates, routes, and cofactors." *Epidemiologic reviews* 18(2): 137-148.

Manns, M. P., M. Buti, E. Gane, J.-M. Pawlotsky, H. Razavi, N. Terrault and Z. Younossi (2017). "Hepatitis C virus infection." *Nature reviews Disease primers* 3(1): 1-19.

Massariol, M. J., S. Zhao, M. Marquis, D. Thibeault and P. W. White (2010). "Protease and helicase activities of hepatitis C virus genotype 4, 5, and 6 NS3-NS4A proteins." *Biochem Biophys Res Commun* 391(1): 692-697.

Mushtaq, S., A. H. Hashmi, A. Khan, S. M. Asad Raza Kazmi and S. Manzoor (2022). "Emergence and Persistence of Resistance-Associated Substitutions in HCV GT3 Patients Failing Direct-Acting Antivirals." *Front Pharmacol* 13: 894460.

Nguyen, V. H., D. Q. Huang, M. H. Le, M. Jin, E. Y. Lee, L. Henry, S. N. Nerurkar, E. Ogawa, K. N. Thin and M. L. Teng (2023). "Global treatment rate and barriers to direct-acting antiviral therapy: a systematic review and meta-analysis of 146 studies and 1 760 352 hepatitis C virus patients." *Liver International* 43(6): 1195-1203.

Omar, A. M., M. A. Elfaky, S. T. Arold, S. H. Soror, M. T. Khayat, H. Z. Asfour, F. H. Bamane and M. E. El-Araby (2020). "1 H-imidazole-2, 5-dicarboxamides as NS4A peptidomimetics: identification of a new approach to inhibit HCV-NS3 protease." *Biomolecules* 10(3): 479.

Pereira, B. J., E. L. Milford, R. L. Kirkman and A. S. Levey (1991). "Transmission of hepatitis C virus by organ transplantation." *New England Journal of Medicine* 325 (7): 454-460.

Poynard, T., V. Leroy, M. Cohard, T. Thevenot, P. Mathurin, P. Opolon and J. P. Zarski (1996). "Meta-Analysis of Interferon Randomized Trials in the Treatment of Viral Hepatitis C: Effects of Dose and Duration." *Hepatology* 24(4): 778-789.

Roder, A. E., C. Vazquez and S. M. Homer (2019). "The acidic domain of the hepatitis C virus NS4A protein is required for viral assembly and envelopment through interactions with the viral El glycoprotein." *PLoS pathogens* 15(2): e1007163.

Rooney, G. and R. Gilson (1998). "Sexual transmission of hepatitis C virus infection." *Sexually transmitted infections* 74(6): 399-404.

Senisterra, G. A., E. Markin, K. Yamazaki, R. Hui, M. Vedadi and D. E. Awrey (2006). "Screening for Ligands Using a Generic and High-Throughput Light-Scattering-Based Assay." *SLAS Discovery* 11(8): 940-948.

Shahul Hameed, U., I. Haider, M. Jamil, B. A. Kountche, X. Guo, R. A. Zarban, D. Kim, S. Al-Babili and S. T. Arold (2018). "Structural basis for specific inhibition of the highly sensitive Sh HTL 7 receptor." *EMBO reports* 19(9): e45619.

Shimizu, Y., K. Yamaji, Y. Masuho, T. Yokota, H. Inoue, K. Sudo, S. Satoh and K. Shimotohno (1996). "Identification of the sequence on NS4A required for enhanced cleavage of the NS5A/5B site by hepatitis C virus NS3 protease." *Journal of Virology* 70(1): 127-132.

Stroffolini, T. and G. Stroffolini (2024). "Prevalence and Modes of Transmission of Hepatitis C Virus Infection: A Historical Worldwide Review." *Viruses* 16(7): 1115.

Tabata, K., C. J. Neufeldt and R. Bartenschlager (2020). "Hepatitis C virus replication." *Cold Spring Harbor perspectives in medicine* 10(3): a037093.

Vuilhorgne, M., J. Malpart, S. Mutti and S. Mignani (2003). "Preparative route to 2-ethoxycarbonylimidazole-4-phosphonate and diethylimidazole-2,4-dicarboxylate." *Journal of Heterocyclic Chemistry* 40(1): 159-162.

Yang, J., J.-L. Qi, X.-X. Wang, X.-H. Li, R. Jin, B.-Y. Liu, H.-X. Liu and H.-Y. Rao (2023). "The burden of hepatitis C virus in the world, China, India, and the United States from 1990 to 2019." *Frontiers in Public Health* 11: 1041201.

Younai, F. S. (2010). "Health care-Associated transmission of hepatitis B & C viruses in dental care (dentistry)." *Clinics in liver disease* 14(1): 93-104.

Zam, H. A., D. Barrett, A. Tanaka, H. Sasaki, K. Matsuda, M. Sakurai, T. Terasawa, F. Shirai, T. Chiba, Y. Matsumoto and S. Tawara (2001). "Synthesis and antibacterial activity of novel 4-pyrrolidinylthio carbapenems Part IV. 2-Alkyl substituents containing cationic heteroaromatics linked via a C—C bond." *Bioorg Med Chem* 9(4): 961-982.

---

---

The invention claimed is:

1. A compound of formula (I)

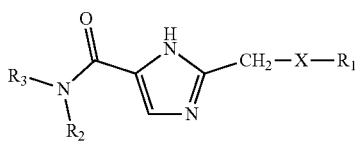

or a salt thereof, a solvate thereof, a tautomer thereof, a stereoisomer thereof, or a mixture thereof;
wherein:
C2-C8 alkyl optionally substituted with at least one substituent selected from the group consisting of an alkyloxy, a cycloalkyloxy, an aryloxy, an amine, and an amide,
X is selected from the group consisting of NH or O R2 is selected from the group consisting of H, alkyl, aralkyl, C1-C10 heteroalkyl, heteroarylalkyl, or heterocyclic, wherein said C1-C10 heteroalkyl comprises up to 10 heteroatoms selected from the group consisting of nitrogen, oxygen or sulfur, and the alkyl moiety of the C1-C10 heteroalkyl group may be in a linear, branched or cyclic arrangement, and $R_3$ is selected is from the group consisting of heteroalkyl, heteroarylalkyl or heterocyclic.

2. The compound of claim 1, wherein $R_1$ is a $C_4$-$C_8$ alkyl substituted with at least one substituent selected from the group consisting of an alkyloxy, a cycloalkyloxy, an aryloxy, an amine, and an amide.

3. The compound of claim 1, wherein R2 is aralkyl, C1-C10 heteroalkyl, heteroarylalkyl, or heterocyclic.

4. The compound of formula (I) of claim 1, which is 2-(((2-acetamidoethyl)amino)methyl)-N-(pyridin-2-ylmethyl)-1H-imidazole-4-carboxamide.

5. A pharmaceutical composition, comprising: the compound of formula (I) of claim 1; and a pharmaceutically acceptable carrier and/or excipient.

6. The pharmaceutical composition of claim 5, further comprising an antiviral agent.

7. The pharmaceutical composition of claim 5, wherein the compound of formula (I) is 2-(((2-acetamidoethyl) amino)methyl)-N-(pyridin-2-ylmethyl)-1H-imidazole-4-carboxamide.

8. A method of treating hepatitis C virus (HCV) infection, the method comprising administering the pharmaceutical composition of claim 5 to a subject in need of therapy.

9. The method of claim 8, wherein 0.1-100 mg/kg of the compound of formula (I) is administered per body weight of the subject.

10. The method of claim 8, wherein the compound of formula (I) binds to an activation site of hepatitis C virus (HCV) serine protease.

\* \* \* \* \*